(12) United States Patent
Lange et al.

(10) Patent No.: US 9,353,363 B2
(45) Date of Patent: May 31, 2016

(54) GLYCOSIDE HYDROLASES FROM THERMOPHILIC FUNGI

(75) Inventors: Lene Lange, Valby (DK); Peter K. Busk, Soeborg (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/884,773

(22) PCT Filed: Jan. 26, 2012

(86) PCT No.: PCT/EP2012/051211
§ 371 (c)(1),
(2), (4) Date: Sep. 30, 2013

(87) PCT Pub. No.: WO2012/101206
PCT Pub. Date: Aug. 2, 2012

(65) Prior Publication Data
US 2014/0065677 A1      Mar. 6, 2014

(30) Foreign Application Priority Data
Jan. 26, 2011   (EP) .................................... 11152252

(51) Int. Cl.
*C12N 9/42*      (2006.01)
*C12P 19/14*    (2006.01)
*C12P 21/00*    (2006.01)

(52) U.S. Cl.
CPC ............... *C12N 9/2437* (2013.01); *C12P 19/14* (2013.01); *C12P 21/00* (2013.01); *C12Y 302/01091* (2013.01)

(58) Field of Classification Search
None
See application file for complete search history.

(56) References Cited

U.S. PATENT DOCUMENTS 7,271,244 B2    9/2007   Dotson et al.
2010/0255542 A1  10/2010   Arnold et al.

FOREIGN PATENT DOCUMENTS

WO  2004/056981 A2   7/2004
WO  2010/060056 A2   5/2010
WO  2010/141325 A1  12/2010

OTHER PUBLICATIONS

Henrissat et al., Biochem. J., vol. 280, No. 2, pp. 309-316 (1991).
Henrissat et al., Biochem. J., vol. 316, pp. 695-696 (1996).
Hong et al., Appl. Microbiol. Biotechnol., vol. 63, No. 1, pp. 42-50 (2003).
Hong et al., Biotechnology Letters, vol. 25, No. 8, pp. 657-661 (2003).
Li et al., Journal of Applied Microbiology, vol. 106, No. 6, pp. 1867-1875 (2009).
Maheshwari et al., Microbiology and Molecular Biology Reviews, vol. 64, No. 3, pp. 461-488 (2000).
Mantyla et al., Appl. Microbiol. Biotechnol., vol. 76, No. 2, pp. 377-386 (2007).
Mouchacca, World J. Microbiol. Biotechnol., vol. 23, No. 12, pp. 1755-1770 (2007).
Paul et al., Biochemistry, vol. 49, No. 15, pp. 3305-3316 (2009).
Ruttersmith et al., Biochem. J., vol. 277, No. 3, pp. 887-890 (1991).

*Primary Examiner* — Suzanne M Noakes
(74) *Attorney, Agent, or Firm* — Robert L. Starnes

(57) ABSTRACT

The present invention relates to isolated polypeptides having cellulolytic activity or hemicellulolytic activity and polynucleotides encoding the polypeptides. The invention also relates to nucleic acid constructs, vectors, and host cells comprising the polynucleotides as well as methods of producing and using the polypeptides.

58 Claims, No Drawings

GLYCOSIDE HYDROLASES FROM THERMOPHILIC FUNGI

CROSS-REFERENCE TO RELATED APPLICATIONS

This application is a 35 U.S.C. 371 national application of PCT/EP2012/051211 filed Jan. 26, 2012, which claims priority or the benefit under 35 U.S.C. 119 of European application no. 11152252.0 filed Jan. 26, 2011, the contents of which are incorporated herein by reference.

REFERENCE TO A SEQUENCE LISTING

This application contains a Sequence Listing in computer readable form, which is incorporated herein by reference.

REFERENCE TO A COMPUTER PROGRAM LISTING APPENDIX

This application contains a Computer Program Listing Appendix containing a computer program submitted on duplicate compact discs, wherein the Appendix is incorporated herein by reference.

BACKGROUND OF THE INVENTION

1. Field of the Invention

The present invention relates to polypeptides having cellulolytic activity or hemicellulolytic activity and polynucleotides encoding the polypeptides. The present invention also relates to nucleic acid constructs, vectors, and host cells comprising the polynucleotides as well as methods of producing and using the polypeptides.

2. Description of the Related Art

There is a rising demand for more sustainable solutions to important problems of a modern society. Demand for more biological processes, products and solutions: Post peak oil era makes it inevitable that the global society at large will have to change from being based on carbon resources from fossils to using renewables. Renewable carbon resources are primarily made of plant materials. The conversion of plant materials (renewable carbon) to substitute the spectrum of useful and needed products (as energy, plastics, chemicals, etc.) obtained currently from crude oil is in general achieved by conversion of the plant biopolymers by the help of microbial enzymes/proteins. This need places high demands on discovery of enzymes and auxiliary proteins from microbes, sufficiently diverse and efficient for converting q wide spectrum of different types of biomass, available globally: from corn stover and wheat straw over sugar cane bagasse and empty flower bunches of oil palm to municipality waste and agroindustrial side streams.

The complexity of the biomass available places high demands to the microbial products: Most agricultural products will have to be reserved for feeding 9 billion people as well as for feeding animals for the food chain. The biomass available for industrial purposes will largely in the future be crop residue/biowaste materials. Such materials are primarily composed of plant lignocelluloses, a highly recalcitrant structure which needs a host of enzymes for full decomposition. This requires even higher demands on the discovery of new and improved enzymes of microbial origin.

An efficient way of enhancing the conversion rate of cellulosic feedstock into ethanol is raising the temperature but this strategy is limited by the temperature stability of the available enzymes.

Another way of enhancing the conversion rate of cellulosic feedstock into ethanol is to optimize the pretreatment of the feedstock before enzymatic degradation but this strategy is limited to acidic pretreatment methods by the pH optimum of the available enzymes.

A third way of enhancing the conversion rate of cellulosic feedstocks into ethanol is adding polypeptides that enhance the cellulolytic activity at low temperatures.

It would be advantageous in the art to improve the conversion of cellulosic feedstock with polypeptides with cellulolytic activity at high temperatures and to provide polypeptides with cellulolytic activity that would be compatible with pretreatment at high pH values. Furthermore, it would be advantageous in the art to improve the conversion of cellulosic feedstocks with polypeptides with cellulolytic enhancing activity at high temperatures. However, only one polypeptide with cellulolytic enhancing activity at high temperatures is known (U.S. Pat. No. 7,271,244). We have identified a number of thermophilic fungi that produce extracellular cellulase activity (endoglucanase and cellobiohydrolase activity) with higher thermostability than cellulase activity from other thermophilic fungi. In addition, several of the fungi produce cellulases that are highly active at pH values over 7. As the fungi produce cellulases with high thermostability and interesting pH optima it is reasonable to assume that other secreted enzymes from these fungi will also have higher thermostability and pH optima than normally observed for fungal enzymes. Therefore, these fungi are useful sources of new enzymes for industrial or other applications, Protein and enzyme discovery can be based on genome sequencing (confined to one organism at a time and depends on time consuming annotations), activity screening (requiring cloning and available high throughput assays), and searching for novelty through sequence similarity (e.g., a PCR based approach).

For decomposition of cellulose and hemicelluloses it is rather simple to construct suitable PCR primers for discovering novel xylanases (e.g., GH10 and GH11) and novel endoglucanases (e.g., GH45) by PCR based screening. The 3D protein structure has through evolution maintained longer stretches of rather highly conserved regions, suitable for primer construction. However, other needed types of enzymes for cellulose decomposition such as the cellobiohydrolases or the auxiliary proteins belonging to GH61 group have either very high sequence variation within each protein family and/or limited areas of sufficient conservation or sequence similarity.

The motivation for the present invention is for more efficient PCR based discovery. The basis is a belief that it should be possible to construct primers based on further similarities than what is possible from an alignment approach simply nested in the fact that it has been possible to group enzymes and other proteins in protein families, which embrace proteins of even very low sequence similarity but with important similarities in fold and characteristics/activities. Similarly, such is also based on the fact that an in silico Blast search could identify a series of proteins which are only distantly related sequence wise but sharing characteristics as, for example, grouping in the same protein family (Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696).

Our hypothesis was that such possible regions suitable for primer construction could be identified based on bringing forward an advanced level of pattern recognition. This approach resulted in a method with simplicity on the one hand and on the other hand significant valuable advantages, such as speed.

The present invention provides polypeptides having cellulolytic activity or hemicellulolytic activity and polynucleotides encoding the polypeptides.

SUMMARY OF THE INVENTION

The present invention relates to isolated polypeptides having cellobiohydrolase activity selected from the group consisting of:

(a) a polypeptide having at least 80% sequence identity to the polypeptide of SEQ ID NO: 2 or SEQ ID NO: 4; at least 90% sequence identity to the polypeptide of SEQ ID NO: 6; at least 91% sequence identity to the polypeptide of SEQ ID NO: 8; or at least 99% sequence identity to the polypeptide of SEQ ID NO: 10;

(b) a polypeptide encoded by a polynucleotide that hybridizes under at least very high stringency conditions with (i) the polypeptide coding sequence of SEQ ID NO: 1, SEQ ID NO: 3, SEQ ID NO: 5, SEQ ID NO: 7, or SEQ ID NO: 9, (ii) the cDNA sequence thereof, or (iii) the full-length complement of (i) or (ii);

(c) a polypeptide encoded by a polynucleotide having at least 80% sequence identity to the polypeptide coding sequence of SEQ ID NO: 1 or SEQ ID NO: 3, or the cDNA sequences thereof; at least 90% sequence identity to the polypeptide coding sequence of SEQ ID NO: 5 or the cDNA sequence thereof; at least 91% sequence identity to the polypeptide coding sequence of SEQ ID NO: 7 or the cDNA sequences thereof; or at least 99% sequence identity to the polypeptide coding sequence of SEQ ID NO: 9 or the cDNA sequence thereof;

(d) a variant comprising the polypeptide of SEQ ID NO: 2, SEQ ID NO: 4, SEQ ID NO: 6, SEQ ID NO: 8, or SEQ ID NO: 10 comprising a substitution, deletion, and/or insertion at one or more (e.g., several) positions; and (e) a fragment of the polypeptide of (a), (b), (c), or (d) that has cellobiohydrolase activity.

The present invention relates to isolated polypeptides having cellobiohydrolase activity selected from the group consisting of:

(a) a polypeptide having at least 70% sequence identity to the polypeptide of SEQ ID NO: 12; at least 80% sequence identity to the polypeptide of SEQ ID NO: 14 or SEQ ID NO: 16; at least 91% sequence identity to the polypeptide of SEQ ID NO: 18; at least 96% sequence identity to the polypeptide of SEQ ID NO: 20; or at least 98% sequence identity to the polypeptide of SEQ ID NO: 22 or SEQ ID NO: 24;

(b) a polypeptide encoded by a polynucleotide that hybridizes under at least very high stringency conditions with (i) the polypeptide coding sequence of SEQ ID NO: 11, SEQ ID NO: 13, SEQ ID NO: 15, SEQ ID NO: 17, SEQ ID NO: 19, SEQ ID NO: 21, or SEQ ID NO: 23, (ii) the cDNA sequence thereof, or (iii) the full-length complement of (i) or (ii);

(c) a polypeptide encoded by a polynucleotide having at least 70% sequence identity to the polypeptide coding sequence SEQ ID NO: 11 or the cDNA sequence thereof; at least 80% sequence identity to the polypeptide coding sequence of SEQ ID NO: 13 or SEQ ID NO: 15, or the cDNA sequences thereof; at least 91% sequence identity to the polypeptide coding sequence of SEQ ID NO: 17 or the cDNA sequence thereof; at least 96% sequence identity to the polypeptide coding sequence of SEQ ID NO: 19 or the cDNA sequence thereof; or at least 98% sequence identity to the polypeptide coding sequence of SEQ ID NO: 21 or SEQ ID NO: 23, or the cDNA sequences thereof;

(d) a variant comprising the polypeptide of SEQ ID NO: 12, SEQ ID NO: 14, SEQ ID NO: 16, SEQ ID NO: 18, SEQ ID NO: 20, SEQ ID NO: 22, or SEQ ID NO: 24 comprising a substitution, deletion, and/or insertion at one or more (e.g., several) positions; and (e) a fragment of the polypeptide of (a), (b), (c), or (d) that has cellobiohydrolase activity.

The present invention relates to isolated polypeptides having endoglucanase activity selected from the group consisting of:

(a) a polypeptide having at least 60% sequence identity to the polypeptide of SEQ ID NO: 26; at least 65% sequence identity to the polypeptide of SEQ ID NO: 28; at least 70% sequence identity to the polypeptide of SEQ ID NO: 30 or SEQ ID NO: 32; at least 80% sequence identity to the polypeptide of SEQ ID NO: 34, SEQ ID NO: 36, or SEQ ID NO: 38; at least 85% sequence identity to the polypeptide of SEQ ID NO: 40 or SEQ ID NO: 42; at least 97% sequence identity to the polypeptide of SEQ ID NO: 44; or at least 98% sequence identity to the polypeptide of SEQ ID NO: 46;

(b) a polypeptide encoded by a polynucleotide that hybridizes under at least high stringency conditions with (i) the polypeptide coding sequence of SEQ ID NO: 25 or SEQ ID NO: 27, (ii) the cDNA sequence thereof, or (iii) the full-length complement of (i) or (ii); or under at least very high stringency conditions with (i) the polypeptide coding sequence of SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, or SEQ ID NO: 45, (ii) the cDNA sequence thereof, or (iii) the full-length complement of (i) or (ii);

(c) a polypeptide encoded by a polynucleotide having at least 60% sequence identity to the polypeptide coding sequence of SEQ ID NO: 25 or the cDNA sequence thereof; at least 65% sequence identity to the polypeptide coding sequence of SEQ ID NO: 27 or the cDNA sequence thereof; at least 70% sequence identity to the polypeptide coding sequence of SEQ ID NO: 29 or SEQ ID NO: 31, or the cDNA sequences thereof; at least 80% sequence identity to the polypeptide coding sequence of SEQ ID NO: 33, SEQ ID NO: 35, or SEQ ID NO: 37, or the cDNA sequences thereof; at least 85% sequence identity to the polypeptide coding sequence of SEQ ID NO: 39 or SEQ ID NO: 41, or the cDNA sequences thereof; at least 97% sequence identity to the polypeptide coding sequence of SEQ ID NO: 43 or the cDNA sequence thereof; or at least 98% sequence identity to the polypeptide coding sequence of SEQ ID NO: 45 or the cDNA sequence thereof;

(d) a variant comprising the polypeptide of SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, or SEQ ID NO: 46 comprising a substitution, deletion, and/or insertion at one or more (e.g., several) positions; and (e) a fragment of the polypeptide of (a), (b), (c), or (d) that has endoglucanase activity.

The present invention relates to isolated GH61 polypeptides having cellulolytic enhancing activity selected from the group consisting of:

(a) a polypeptide having at least 70% sequence identity to the polypeptide of SEQ ID NO: 48; at least 75% sequence identity to the polypeptide of SEQ ID NO: 50, SEQ ID NO: 52, SEQ ID NO: 54, or SEQ ID NO: 79; at least 80% sequence identity to the polypeptide of SEQ ID NO: 56, SEQ ID NO: 58, SEQ ID NO: 60, SEQ ID NO: 62, or SEQ ID NO: 64; at least 85% sequence identity to the polypeptide of SEQ ID NO: 66; or at least 90% sequence identity to the polypeptide of SEQ ID NO: 68, SEQ ID NO: 70, or SEQ ID NO: 72;

(b) a polypeptide encoded by a polynucleotide that hybridizes under at least very high stringency conditions with (i) the polypeptide coding sequence of SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, or SEQ ID NO: 71, (ii) the cDNA sequence thereof, or (iii) the full-length complement of (i) or (ii);

(c) a polypeptide encoded by a polynucleotide having at least 70% sequence identity to the polypeptide coding sequence of SEQ ID NO: 47 or the cDNA sequence thereof; at least 75% sequence identity to the polypeptide coding sequence of SEQ ID NO: 49, SEQ ID NO: 51, or SEQ ID NO: 53, or the cDNA sequences thereof; at least 80% sequence identity to the polypeptide coding sequence of SEQ ID NO: 55, SEQ ID NO: 57, SEQ ID NO: 59, SEQ ID NO: 61, or SEQ ID NO: 63, or the cDNA sequences thereof; at least 85% sequence identity to the polypeptide coding sequence of SEQ ID NO: 65 or the cDNA sequence thereof; or at least 90% sequence identity to the polypeptide coding sequence of SEQ ID NO: 67, SEQ ID NO: 69, or SEQ ID NO: 71, or the cDNA sequences thereof;

(d) a variant comprising the polypeptide of SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 69, SEQ ID NO: 70, SEQ ID NO: 72, or SEQ ID NO: 79 comprising a substitution, deletion, and/or insertion at one or more (e.g., several) positions; and (e) a fragment of the polypeptide of (a), (b), (c), or (d) that has cellulolytic enhancing activity.

The present invention relates to isolated polypeptides having xylanase activity selected from the group consisting of:

(a) a polypeptide having at least 70% sequence identity to the polypeptide of SEQ ID NO: 74, at least 94% sequence identity to the polypeptide of SEQ ID NO: 78, or at least 98% sequence identity to the polypeptide of SEQ ID NO: 76;

(b) a polypeptide encoded by a polynucleotide that hybridizes under at least very high stringency conditions with (i) the polypeptide coding sequence of SEQ ID NO: 73, SEQ ID NO: 75, or SEQ ID NO: 77, (ii) the cDNA sequence thereof, or (iii) the full-length complement of (i) or (ii);

(c) a polypeptide encoded by a polynucleotide having at least 70% sequence identity to the polypeptide coding sequence of SEQ ID NO: 73 or the cDNA sequence thereof, at least 94% sequence identity to the polypeptide coding sequence of SEQ ID NO: 77 or the cDNA sequence thereof, or at least 98% sequence identity to the polypeptide coding sequence of SEQ ID NO: 75 or the cDNA sequence thereof;

(d) a variant comprising the polypeptide of SEQ ID NO: 74, SEQ ID NO: 76, or SEQ ID NO: 78 comprising a substitution, deletion, and/or insertion at one or more (e.g., several) positions; and (e) a fragment of the polypeptide of (a), (b), (c), or (d) that has xylanase activity.

The present invention also relates to isolated polynucleotides encoding the polypeptides of the present invention; nucleic acid constructs, recombinant expression vectors, and recombinant host cells comprising the polynucleotides; and methods of producing the polypeptides.

The present invention also relates to processes for degrading or converting a cellulosic or xylan-containing material, comprising: treating the cellulosic or xylan-containing material with an enzyme composition in the presence of a polypeptide having cellobiohydrolase, endoglucanase, cellulolytic enhancing, or xylanase activity of the present invention. In one aspect, the processes further comprise recovering the degraded or converted cellulosic or xylan-containing material.

The present invention also relates to processes of producing a fermentation product, comprising: (a) saccharifying a cellulosic or xylan-containing material with an enzyme composition in the presence of a polypeptide having cellobiohydrolase, endoglucanase, cellulolytic enhancing, or xylanase activity of the present invention; (b) fermenting the saccharified cellulosic or xylan-containing material with one or more (e.g., several) fermenting microorganisms to produce the fermentation product; and (c) recovering the fermentation product from the fermentation.

The present invention also relates to processes of fermenting a cellulosic or xylan-containing material, comprising: fermenting the cellulosic or xylan-containing material with one or more (e.g., several) fermenting microorganisms, wherein the cellulosic or xylan-containing material is saccharified with an enzyme composition in the presence of a polypeptide having cellobiohydrolase, endoglucanase, cellulolytic enhancing, or xylanase activity of the present invention. In one aspect, the fermenting of the cellulosic or xylan-containing material produces a fermentation product. In another aspect, the processes further comprise recovering the fermentation product from the fermentation.

DEFINITIONS

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase equals the amount of enzyme capable of releasing 1 µmole of glucuronic or 4-O-methyl-glucuronic acid per minute at pH 5, 40° C.

Amino acid sequence: The term "amino acid sequence" means the order in which amino acid residues, connected by peptide bonds, lie in the chains of peptides and proteins. The sequence is generally reported from the N-terminal end containing a free amino group to the C-terminal end containing a free carboxyl group. Single letter amino acid codes are used. The code "X" is used to designate one or more residues of any amino acid. Single letter nucleic acid codes are used. The code "n" is used to designate one or more residues of any nucleic acid.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 µmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 µmole of p-nitrophenolate anion produced per minute at 40° C., pH 5 from 1 mM p-nitrophenyl-beta-D-xyloside as substrate in 100 mM sodium citrate containing 0.01% TWEEN® 20.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters,* 149: 152-156; van Tilbeurgh and Claeyssens, 1985, *FEBS Letters,* 187: 283-288; and Tomme et al., 1988, *Eur. J. Biochem.* 170: 575-581.

The polypeptides of the present invention have at least 20%, e.g., at least 40%, at least 50%, at least 60%, at least 70%, at least 80%, at least 90%, at least 95%, and at least 100% of the cellobiohydrolase activity of the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, or SEQ ID NO: 24.

Cellulosic material: The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material. In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is *arundo*. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is *miscanthus*. In another aspect, the cellulosic material is orange peel. In another aspect, the cellulosic material is rice straw. In another aspect, the cellulosic material is switchgrass. In another aspect, the cellulosic material is wheat straw.

In another aspect, the cellulosic material is aspen. In another aspect, the cellulosic material is *eucalyptus*. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

In another aspect, degrading or converting of a cellulosic material is performed in a bioreactor or in situ, i.e., in the place where the cellulosic material naturally occurs.

Cellulolytic enzyme or cellulase or cellulose-degrading polypeptide: The term "cellulolytic enzyme" or "cellulase" or "cellulose-degrading polypeptide" means one or more (e.g., several) enzymes that hydrolyze a cellulosic material. Such enzymes may include endoglucanase(s), cellobiohydrolase(s), beta-glucosidase(s), or combinations thereof. The term refers broadly to enzymes exhibiting cellulase or cellulolytic activity such as glycoside hydrolases (GHs) and to enzymes with capacity to enhance the breakdown of lignocellulose when used in conjunction with a cellulase or a mixture of cellulases. Cellulose-degrading proteins exhibit catalytic or other activity making the protein able to by itself or together with other proteins or with catalysts to convert cellulose to smaller cellulose chains or to monomeric sugars. Examples of such enzymes, but not limited to, are represented by glycoside hydrolases (GHs) of the Carbohydrate-Active Enzymes database (CAZy). Thus, polypeptides of the GH6, GH7, GH10, GH45, and GH61 families are herein referred to as cellulose-degrading potypeptides.

The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No. 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, Calif., USA).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Complementarity: In molecular biology the term "complementarity" is a property of double-stranded nucleic acids such as DNA and RNA as well as DNA:RNA duplexes. Each strand is complementary to the other in that the base pairs between them are non-covalently connected via two or three hydrogen bonds. For DNA, adenosine (A) bases complement thymine (T) bases and vice versa; guanine (G) bases complement cytosine (C) bases and vice versa. With RNA, it is the same except that adenine (A) bases complement uracil (U) bases instead of thymine (T) bases.

Since there is only one complementary base for each of the bases found in DNA and in RNA, one can reconstruct a complementary strand for any single strand. All C bases in one strand will pair with G bases in the complementary strand, etc. This is essential for DNA replication.

For example, the complementary strand of the DNA sequence 5' A G T C A T G 3' is 3' T C A G T A C 5'.

The sequence 5' C A T G A C T 3' is called the reverse complementary strand to the DNA sequence 5' A G T C A T G 3' when it is written with the 5' end on the left and the 3' end on the right Sequences of degenerate nucleotides such as in primers are represented according to the IUPAC code for degenerate nucleotides: A: Adenine, C: Cytosine, D: A, G, or T (A/G/T), G: Guanine, H: A, C, or T (A/C/T), K: G or T (G/T), M: A or C (NC), N: A, C, G, or T (A/C/G/T), R: A or G (NG), S: C or G (C/G), T: Thymine, V: A, C, or G(A/C/G), W: A or T (NT), Y: C or T (C/T).

Composition: The term "composition" means a mixture of two or more (e.g., several) substances, e.g., enzymes.

Control sequences: The term "control sequences" means nucleic acid sequences necessary for expression of a polynucleotide encoding a polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

The polypeptides of the present invention have at least 20%, e.g., at least 40%, at least 50%, at least 60%, at least 70%, at least 80%, at least 90%, at least 95%, and at least 100% of the endoglucanase activity of the polypeptide of SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, or SEQ ID NO: 46.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Family 6 glycoside hydrolase: The term "Family 6 glycoside hydrolase" or "Family GH6" or "GH6" means a polypeptide falling into the glycoside hydrolase Family 6 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Family 7 glycoside hydrolase: The term "Family 7 glycoside hydrolase" or "Family GH7" or "GH7" means a polypeptide falling into the glycoside hydrolase Family 7 according to Henrissat, 1991, supra, and Henrissat and Bairoch, 1996, supra.

Family 10 glycoside hydrolase: The term "Family 10 glycoside hydrolase" or "Family GH10" or "GH10" means a polypeptide falling into the glycoside hydrolase Family 10 according to Henrissat, 1991, supra, and Henrissat and Bairoch, 1996, supra.

Family 45 glycoside hydrolase: The term "Family 45 glycoside hydrolase" or "Family GH45" or "GH45" means a polypeptide falling into the glycoside hydrolase Family 45 according to Henrissat, 1991, supra, and Henrissat and Bairoch, 1996, supra.

Family 61 glycoside hydrolase: The term "Family 61 glycoside hydrolase" or "Family GH61" or "GH61" means a polypeptide falling into the glycoside hydrolase Family 61 according to Henrissat, 1991, supra, and Henrissat and Bairoch, 1996, supra. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3-methoxycinnamoyl (feruloyl) groups from esterified sugar, which is usually arabinose in natural biomass substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a polypeptide; wherein the fragment has cellobiohydrolase, endoglucanase, cellulolytic enhancing, or xylanase activity. In one aspect, a fragment contains at least 85% of the amino acid residues, e.g., at least 90% of the amino acid residues or at least 90% of the amino acid residues of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 74, SEQ ID NO: 76, SEQ ID NO: 78, or SEQ ID NO: 79.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). The polypeptide of the present invention may be used in industrial applications in the form of a fermentation broth product, that is, the polypeptide of the present invention is a component of a fermentation broth used as a product in industrial applications (e.g., ethanol production). The fermentation broth product will in addition to the polypeptide of the present invention comprise additional ingredients used in the fermentation process, such as, for example, cells (including, the host cells containing the gene encoding the polypeptide of the present invention which are used to produce the polypeptide of interest), cell debris, biomass, fermentation media and/or fermentation products. The fermentation broth may optionally be subjected to one or more purification (including filtration) steps to remove or reduce one more components of a fermentation process. Accordingly, an isolated substance may be present in such a fermentation broth product.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having cellobiohydrolase, endoglucanase, cellulolytic enhancing, or xylanase activity.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Peptide: The term "peptide" means a smaller peptide comprising fewer than about 20 consecutive amino acids.

Polynucleotide: The term "polynucleotide" means to a nucleic acid sequence that comprises more than about 30 consecutive nucleotides or modified nucleotides. Polynucleotides include DNA, RNA, m-RNA, r-RNA, t-RNA, cDNA, DNA-RNA duplexes, etc.

Polypeptide: The term "polypeptide" means a longer peptide that comprises more than about 20 consecutive amino acids. The term "polypeptide" encompasses proteins, fragments of proteins, cleaved forms of proteins, partially digested proteins, and the like, which are greater than about 20 consecutive amino acids.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes NS, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

The polypeptides of the present invention have at least 20%, e.g., at least 40%, at least 50%, at least 60%, at least 70%, at least 80%, at least 90%, at least 95%, and at least 100% of the cellulolytic enhancing activity of the polypeptide of SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 69, SEQ ID NO: 70, SEQ ID NO: 72, or SEQ ID NO: 79.

Pretreated corn stover: The term "PCS" or "Pretreated Corn Stover" means a cellulosic material derived from corn stover by treatment with heat and dilute sulfuric acid, alkaline pretreatment, or neutral pretreatment.

Sequence identity: The term "sequence identity" means a comparison between pairs of nucleic acid or amino acid molecules, i.e., the relatedness between two amino acid sequences or between two nucleotide sequences. In general, the sequences are aligned so that the highest order match is obtained. Methods for determining sequence identity are known and can be determined by commercially available computer programs that can calculate % identity between two or more sequences. A typical example of such a computer program is CLUSTAL. As an illustration, by a polynucleotide having a nucleotide sequence having at least, for example, 90% sequence identity to a reference nucleotide sequence is intended that the nucleotide sequence of the polynucleotide is identical to the reference sequence except that the polynucleotide sequence may include on average of up to 10 point mutations per each 100 nucleotides of the reference nucleotide sequence. In other words, to obtain a polynucleotide having a nucleotide sequence at least 90% identical to a reference nucleotide sequence, up to 10% of the nucleotides in the reference sequence may be deleted or substituted with another nucleotide, or a number of nucleotides up to 10% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Similarly, by a polypeptide having an amino acid sequence having at least, for example, 90% sequence identity to a reference amino acid sequence is intended that the amino acid sequence of the polypeptide is identical to the reference sequence except that the polypeptide sequence may include on average up to 10 amino acid alterations per each 100 amino acids of the reference amino acid. In other words, to obtain a polypeptide having an amino acid sequence at least 90% identical to a reference amino acid sequence, up to 10% of the amino acid residues in the reference sequence may be deleted or substituted with another amino acid, or a number of amino acids up to 10% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Preferred methods to determine identity are designed to give the largest match between the sequences tested. Methods to determine identity are described in publicly available computer programs. Preferred computer program methods to determine identity between two sequences include the GCG program package, including GAP (Devereux et al., 1984, *Nucl. Acid. Res.* 12: 387; Genetics Computer Group, University of Wisconsin, Madison, Wis., USA), BLASTP, BLASTN, and FASTA (Altschul et al., 1990, *J. Mol. Biol.* 215: 403-410). The BLASTX program is publicly available from the National Center for Biotechnology Information (NCBI) and other sources (BLAST Manual, Altschul et al. NCB/NLM/NIH Bethesda, Md., USA; Altschul et al., supra).

The well-known Smith Waterman algorithm may also be used to determine identity. For example, using the computer algorithm GAP (Genetics Computer Group, University of Wisconsin, Madison, Wis., USA), two proteins for which the percent sequence identity is to be determined are aligned for optimal matching of their respective amino acids (the "matched span", as determined by the algorithm). A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix is also used by the algorithm (see Dayhoff et al., 1978, Atlas of Protein Sequence and Structure, Vol. 5, Suppl. 3, (1978) for the PAM 250 comparison matrix; Henikoff et al., 1992, *Proc. Natl. Acad. Sci USA* 89: 10915-10919, for the BLOSUM 62 comparison matrix).

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment–Total Number of Gaps in Alignment)

Subsequence: The term "subsequence" means a polynucleotide having one or more (e.g., several) nucleotides absent from the 5' and/or 3' end of a polypeptide coding sequence; wherein the subsequence encodes a fragment having cellobiohydrolase, endoglucanase, cellulolytic enhancing, or xylanase activity. In one aspect, a subsequence contains at least 85% of the nucleotides, e.g., at least 90% of the nucleotides or at least 95% of the nucleotides of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, or SEQ ID NO: 77.

Variant: The term "variant" means a polypeptide having cellobiohydrolase, endoglucanase, cellulolytic enhancing, or xylanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In the processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580(19): 4597-4601; Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 (4-(1,1,3,3-tetramethylbutyl)phenyl-polyethylene glycol) and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

The polypeptides of the present invention have at least 20%, e.g., at least 40%, at least 50%, at least 60%, at least 70%, at least 80%, at least 90%, at least 95%, and at least 100% of the xylanase activity of the polypeptide of SEQ ID NO: 74, SEQ ID NO: 76, or SEQ ID NO: 78.

DETAILED DESCRIPTION OF THE INVENTION

Polypeptides Having Cellobiohydrolase, Endoglucanase, Cellulolytic Enhancing, or Xylanase Activity In an embodiment, the present invention relates to isolated polypeptides having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 2 or SEQ ID NO: 4; at least 90%, e.g., at least 91%, at least 92%, at least 93%, at least 94%, at least 95%, at least 96%, at least 97%, at least 98%, at least 99%, or 100% sequence identity to the polypeptide of SEQ ID NO: 6; at least 91%, e.g., at least 92%, at least 93%, at least 94%, at least 95%, at least 96%, at least 97%, at least 98%, at least 99%, or 100% sequence identity to the polypeptide of SEQ ID NO: 8; or at least 99%, e.g., 100% sequence identity to the polypeptide of SEQ ID NO: 10, which have cellobiohydrolase activity. In one aspect, the polypeptides differ by up to 10 amino acids, e.g., 1, 2, 3, 4, 5, 6, 7, 8, 9, or 10, from the polypeptide of SEQ ID NO: 2, SEQ ID NO: 4, SEQ ID NO: 6, SEQ ID NO: 8, or SEQ ID NO: 10.

A polypeptide of the present invention preferably comprises or consists of the amino acid sequence of SEQ ID NO:

2; or an allelic variant thereof; or is a fragment thereof having cellobiohydrolase activity. In another aspect, the polypeptide comprises or consists of the polypeptide of SEQ ID NO: 2.

A polypeptide of the present invention preferably comprises or consists of the amino acid sequence of SEQ ID NO: 4; or an allelic variant thereof; or is a fragment thereof having cellobiohydrolase activity. In another aspect, the polypeptide comprises or consists of the polypeptide of SEQ ID NO: 4.

A polypeptide of the present invention preferably comprises or consists of the amino acid sequence of SEQ ID NO: 6; or an allelic variant thereof; or is a fragment thereof having cellobiohydrolase activity. In another aspect, the polypeptide comprises or consists of the polypeptide of SEQ ID NO: 6.

A polypeptide of the present invention preferably comprises or consists of the amino acid sequence of SEQ ID NO: 8; or an allelic variant thereof; or is a fragment thereof having cellobiohydrolase activity. In another aspect, the polypeptide comprises or consists of the polypeptide of SEQ ID NO: 8.

A polypeptide of the present invention preferably comprises or consists of the amino acid sequence of SEQ ID NO: 10; or an allelic variant thereof; or is a fragment thereof having cellobiohydrolase activity. In another aspect, the polypeptide comprises or consists of the polypeptide of SEQ ID NO: 10.

In another embodiment, the present invention relates to isolated polypeptides having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 12; at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 14 or SEQ ID NO: 16; at least 91%, e.g., at least 92%, at least 93%, at least 94%, at least 95%, at least 96%, at least 97%, at least 98%, at least 99%, or 100% sequence identity to the polypeptide of SEQ ID NO: 18; at least 96%, e.g., at least 97%, at least 98%, at least 99%, or 100% sequence identity to the polypeptide of SEQ ID NO: 20; or at least 98%, e.g., at least 99% or 100% sequence identity to the polypeptide of SEQ ID NO: 22 or SEQ ID NO: 24, which have cellobiohydrolase activity. In one aspect, the polypeptides differ by up to 10 amino acids, e.g., 1, 2, 3, 4, 5, 6, 7, 8, 9, or 10, from the polypeptide of SEQ ID NO: 12, SEQ ID NO: 14, SEQ ID NO: 16, SEQ ID NO: 18, SEQ ID NO: 20, SEQ ID NO: 22, or SEQ ID NO: 24.

A polypeptide of the present invention preferably comprises or consists of the amino acid sequence of SEQ ID NO: 12; or an allelic variant thereof; or is a fragment thereof having cellobiohydrolase activity. In another aspect, the polypeptide comprises or consists of the polypeptide of SEQ ID NO: 12.

A polypeptide of the present invention preferably comprises or consists of the amino acid sequence of SEQ ID NO: 14; or an allelic variant thereof; or is a fragment thereof having cellobiohydrolase activity. In another aspect, the polypeptide comprises or consists of the polypeptide of SEQ ID NO: 14.

A polypeptide of the present invention preferably comprises or consists of the amino acid sequence of SEQ ID NO: 16; or an allelic variant thereof; or is a fragment thereof having cellobiohydrolase activity. In another aspect, the polypeptide comprises or consists of the polypeptide of SEQ ID NO: 16.

A polypeptide of the present invention preferably comprises or consists of the amino acid sequence of SEQ ID NO: 18; or an allelic variant thereof; or is a fragment thereof having cellobiohydrolase activity. In another aspect, the polypeptide comprises or consists of the polypeptide of SEQ ID NO: 18.

A polypeptide of the present invention preferably comprises or consists of the amino acid sequence of SEQ ID NO: 20; or an allelic variant thereof; or is a fragment thereof having cellobiohydrolase activity. In another aspect, the polypeptide comprises or consists of the polypeptide of SEQ ID NO: 20.

A polypeptide of the present invention preferably comprises or consists of the amino acid sequence of SEQ ID NO: 22; or an allelic variant thereof; or is a fragment thereof having cellobiohydrolase activity. In another aspect, the polypeptide comprises or consists of the polypeptide of SEQ ID NO: 22.

A polypeptide of the present invention preferably comprises or consists of the amino acid sequence of SEQ ID NO: 24; or an allelic variant thereof; or is a fragment thereof having cellobiohydrolase activity. In another aspect, the polypeptide comprises or consists of the polypeptide of SEQ ID NO: 24.

In another embodiment, the present invention relates to isolated polypeptides having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 26; at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 28; at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 30 or SEQ ID NO: 32; at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 34, SEQ ID NO: 36, or SEQ ID NO: 38; at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 40 or SEQ ID NO: 42; at least 97%, e.g., at least 98%, at least 99%, or 100% sequence identity to the polypeptide of SEQ ID NO: 44; or at least 98%, e.g., at least 99% or 100% sequence identity to the polypeptide of SEQ ID NO: 46, which have endoglucanase activity. In one aspect, the polypeptides differ by up to 10 amino acids, e.g., 1, 2, 3, 4, 5, 6, 7, 8, 9, or 10, from the polypeptide of SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, or SEQ ID NO: 46.

A polypeptide of the present invention preferably comprises or consists of the amino acid sequence of SEQ ID NO: 26; or an allelic variant thereof; or is a fragment thereof having cellobiohydrolase activity. In another aspect, the polypeptide comprises or consists of the polypeptide of SEQ ID NO: 26.

A polypeptide of the present invention preferably comprises or consists of the amino acid sequence of SEQ ID NO: 28; or an allelic variant thereof; or is a fragment thereof having cellobiohydrolase activity. In another aspect, the polypeptide comprises or consists of the polypeptide of SEQ ID NO: 28.

A polypeptide of the present invention preferably comprises or consists of the amino acid sequence of SEQ ID NO: 30; or an allelic variant thereof; or is a fragment thereof having cellobiohydrolase activity. In another aspect, the polypeptide comprises or consists of the polypeptide of SEQ ID NO: 30.

A polypeptide of the present invention preferably comprises or consists of the amino acid sequence of SEQ ID NO: 32; or an allelic variant thereof; or is a fragment thereof having cellobiohydrolase activity. In another aspect, the polypeptide comprises or consists of the polypeptide of SEQ ID NO: 32.

A polypeptide of the present invention preferably comprises or consists of the amino acid sequence of SEQ ID NO: 34; or an allelic variant thereof; or is a fragment thereof having cellobiohydrolase activity. In another aspect, the polypeptide comprises or consists of the polypeptide of SEQ ID NO: 34.

A polypeptide of the present invention preferably comprises or consists of the amino acid sequence of SEQ ID NO: 36; or an allelic variant thereof; or is a fragment thereof having cellobiohydrolase activity. In another aspect, the polypeptide comprises or consists of the polypeptide of SEQ ID NO: 36.

A polypeptide of the present invention preferably comprises or consists of the amino acid sequence of SEQ ID NO: 38; or an allelic variant thereof; or is a fragment thereof having cellobiohydrolase activity. In another aspect, the polypeptide comprises or consists of the polypeptide of SEQ ID NO: 38.

A polypeptide of the present invention preferably comprises or consists of the amino acid sequence of SEQ ID NO: 40; or an allelic variant thereof; or is a fragment thereof having cellobiohydrolase activity. In another aspect, the polypeptide comprises or consists of the polypeptide of SEQ ID NO: 40.

A polypeptide of the present invention preferably comprises or consists of the amino acid sequence of SEQ ID NO: 42; or an allelic variant thereof; or is a fragment thereof having cellobiohydrolase activity. In another aspect, the polypeptide comprises or consists of the polypeptide of SEQ ID NO: 42.

A polypeptide of the present invention preferably comprises or consists of the amino acid sequence of SEQ ID NO: 44; or an allelic variant thereof; or is a fragment thereof having cellobiohydrolase activity. In another aspect, the polypeptide comprises or consists of the polypeptide of SEQ ID NO: 44.

A polypeptide of the present invention preferably comprises or consists of the amino acid sequence of SEQ ID NO: 46; or an allelic variant thereof; or is a fragment thereof having cellobiohydrolase activity. In another aspect, the polypeptide comprises or consists of the polypeptide of SEQ ID NO: 46.

In another embodiment, the present invention relates to isolated polypeptides having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 48; at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 50, SEQ ID NO: 52, SEQ ID NO: 54, or SEQ ID NO: 79; at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 56, SEQ ID NO: 58, SEQ ID NO: 60, SEQ ID NO: 62, or SEQ ID NO: 64; at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 66; or at least 90%, e.g., at least 91%, at least 92%, at least 93%, at least 94%, at least 95%, at least 96%, at least 97%, at least 98%, at least 99%, or 100% sequence identity to the polypeptide of SEQ ID NO: 68, SEQ ID NO: 70, or SEQ ID NO: 72, which have cellulolytic enhancing activity. In one aspect, the polypeptides differ by up to 10 amino acids, e.g., 1, 2, 3, 4, 5, 6, 7, 8, 9, or 10, from the polypeptide of SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 69, SEQ ID NO: 70, SEQ ID NO: 72, or SEQ ID NO: 79.

A polypeptide of the present invention preferably comprises or consists of the amino acid sequence of SEQ ID NO: 48; or an allelic variant thereof; or is a fragment thereof having cellobiohydrolase activity. In another aspect, the polypeptide comprises or consists of the polypeptide of SEQ ID NO: 48.

A polypeptide of the present invention preferably comprises or consists of the amino acid sequence of SEQ ID NO: 50; or an allelic variant thereof; or is a fragment thereof having cellobiohydrolase activity. In another aspect, the polypeptide comprises or consists of the polypeptide of SEQ ID NO: 50.

A polypeptide of the present invention preferably comprises or consists of the amino acid sequence of SEQ ID NO: 52; or an allelic variant thereof; or is a fragment thereof having cellobiohydrolase activity. In another aspect, the polypeptide comprises or consists of the polypeptide of SEQ ID NO: 52.

A polypeptide of the present invention preferably comprises or consists of the amino acid sequence of SEQ ID NO: 54; or an allelic variant thereof; or is a fragment thereof having cellobiohydrolase activity. In another aspect, the polypeptide comprises or consists of the polypeptide of SEQ ID NO: 54.

A polypeptide of the present invention preferably comprises or consists of the amino acid sequence of SEQ ID NO: 56; or an allelic variant thereof; or is a fragment thereof having cellobiohydrolase activity. In another aspect, the polypeptide comprises or consists of the polypeptide of SEQ ID NO: 56.

A polypeptide of the present invention preferably comprises or consists of the amino acid sequence of SEQ ID NO: 58; or an allelic variant thereof; or is a fragment thereof having cellobiohydrolase activity. In another aspect, the polypeptide comprises or consists of the polypeptide of SEQ ID NO: 58.

A polypeptide of the present invention preferably comprises or consists of the amino acid sequence of SEQ ID NO: 60; or an allelic variant thereof; or is a fragment thereof having cellobiohydrolase activity. In another aspect, the polypeptide comprises or consists of the polypeptide of SEQ ID NO: 60.

A polypeptide of the present invention preferably comprises or consists of the amino acid sequence of SEQ ID NO: 62; or an allelic variant thereof; or is a fragment thereof having cellobiohydrolase activity. In another aspect, the polypeptide comprises or consists of the polypeptide of SEQ ID NO: 62.

A polypeptide of the present invention preferably comprises or consists of the amino acid sequence of SEQ ID NO: 64; or an allelic variant thereof; or is a fragment thereof having cellobiohydrolase activity. In another aspect, the polypeptide comprises or consists of the polypeptide of SEQ ID NO: 64.

A polypeptide of the present invention preferably comprises or consists of the amino acid sequence of SEQ ID NO: 66; or an allelic variant thereof; or is a fragment thereof having cellobiohydrolase activity. In another aspect, the polypeptide comprises or consists of the polypeptide of SEQ ID NO: 66.

A polypeptide of the present invention preferably comprises or consists of the amino acid sequence of SEQ ID NO: 68; or an allelic variant thereof; or is a fragment thereof having cellobiohydrolase activity. In another aspect, the polypeptide comprises or consists of the polypeptide of SEQ ID NO: 68.

A polypeptide of the present invention preferably comprises or consists of the amino acid sequence of SEQ ID NO: 70; or an allelic variant thereof; or is a fragment thereof having cellobiohydrolase activity. In another aspect, the polypeptide comprises or consists of the polypeptide of SEQ ID NO: 70.

A polypeptide of the present invention preferably comprises or consists of the amino acid sequence of SEQ ID NO: 72; or an allelic variant thereof; or is a fragment thereof having cellobiohydrolase activity. In another aspect, the polypeptide comprises or consists of the polypeptide of SEQ ID NO: 72.

A polypeptide of the present invention preferably comprises or consists of the amino acid sequence of SEQ ID NO: 79; or an allelic variant thereof; or is a fragment thereof having cellobiohydrolase activity. In another aspect, the polypeptide comprises or consists of the polypeptide of SEQ ID NO: 79.

In another embodiment, the present invention relates to isolated polypeptides having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 74, at least 94%, e.g., at least 95%, at least 96%, at least 97%, at least 98%, at least 99%, or 100% sequence identity to the polypeptide of SEQ ID NO: 78, or at least 98%, e.g., at least 99% or 100% sequence identity to the polypeptide of SEQ ID NO: 76, which have xylanase activity. In one aspect, the polypeptides differ by up to 10 amino acids, e.g., 1, 2, 3, 4, 5, 6, 7, 8, 9, or 10, from the polypeptide of SEQ ID NO: 74, SEQ ID NO: 76, or SEQ ID NO: 78.

A polypeptide of the present invention preferably comprises or consists of the amino acid sequence of SEQ ID NO: 74; or an allelic variant thereof; or is a fragment thereof having cellobiohydrolase activity. In another aspect, the polypeptide comprises or consists of the polypeptide of SEQ ID NO: 74.

A polypeptide of the present invention preferably comprises or consists of the amino acid sequence of SEQ ID NO: 76; or an allelic variant thereof; or is a fragment thereof having cellobiohydrolase activity. In another aspect, the polypeptide comprises or consists of the polypeptide of SEQ ID NO: 76.

A polypeptide of the present invention preferably comprises or consists of the amino acid sequence of SEQ ID NO: 78; or an allelic variant thereof; or is a fragment thereof having cellobiohydrolase activity. In another aspect, the polypeptide comprises or consists of the polypeptide of SEQ ID NO: 78.

In another embodiment, the present invention relates to isolated polypeptides having cellobiohydrolase activity encoded by polynucleotides that hybridize under very low stringency conditions, low stringency conditions, medium stringency conditions, medium-high stringency conditions, high stringency conditions, or very high stringency conditions with (i) the polypeptide coding sequence of SEQ ID NO: 1, SEQ ID NO: 3, SEQ ID NO: 5, SEQ ID NO: 7, or SEQ ID NO: 9, (ii) the cDNA sequence thereof, or (iii) the full-length complement of (i) or (ii) (Sambrook et al., 1989, *Molecular Cloning, A Laboratory Manual,* 2nd edition, Cold Spring Harbor, New York).

In another embodiment, the present invention relates to isolated polypeptides having cellobiohydrolase activity encoded by polynucleotides that hybridize under very low stringency conditions, low stringency conditions, medium stringency conditions, medium-high stringency conditions, high stringency conditions, or very high stringency conditions with (i) the polypeptide coding sequence of SEQ ID NO: 11, SEQ ID NO: 13, SEQ ID NO: 15, SEQ ID NO: 17, SEQ ID NO: 19, SEQ ID NO: 21, or SEQ ID NO: 23, (ii) the cDNA sequence thereof, or (iii) the full-length complement of (i) or (ii) (Sambrook et al., 1989, *Molecular Cloning, A Laboratory Manual,* 2d edition, Cold Spring Harbor, New York).

In another embodiment, the present invention relates to isolated polypeptides having endoglucanase activity encoded by polynucleotides that hybridize under very low stringency conditions, low stringency conditions, medium stringency conditions, medium-high stringency conditions, high stringency conditions, or very high stringency conditions with (i) the polypeptide coding sequence of SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, or SEQ ID NO: 45, (ii) the cDNA sequence thereof, or (iii) the full-length complement of (i) or (ii) (Sambrook et al., 1989, *Molecular Cloning, A Laboratory Manual,* 2d edition, Cold Spring Harbor, New York).

In another embodiment, the present invention relates to isolated polypeptides having cellulolytic enhancing activity encoded by polynucleotides that hybridize under very low stringency conditions, low stringency conditions, medium stringency conditions, medium-high stringency conditions, high stringency conditions, or very high stringency conditions with (i) the polypeptide coding sequence of SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, or SEQ ID NO: 71, (ii) the cDNA sequence thereof, or (iii) the full-length complement of (i) or (ii) (Sambrook et al., 1989, *Molecular Cloning, A Laboratory Manual,* 2d edition, Cold Spring Harbor, New York).

In another embodiment, the present invention relates to isolated polypeptides having xylanase activity encoded by polynucleotides that hybridize under very low stringency conditions, low stringency conditions, medium stringency conditions, medium-high stringency conditions, high stringency conditions, or very high stringency conditions with (i) the polypeptide coding sequence of SEQ ID NO: 73, SEQ ID NO: 75, or SEQ ID NO: 77, (ii) the cDNA sequence thereof, or (iii) the full-length complement of (i) or (ii) (Sambrook et al., 1989, *Molecular Cloning, A Laboratory Manual,* 2d edition, Cold Spring Harbor, New York).

The polynucleotide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, or SEQ ID NO: 77, or a subsequence thereof, as well as the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 74, SEQ ID NO: 76, SEQ ID NO: 78, or SEQ ID NO: 79, the mature polypeptide thereof, or a fragment thereof, may be used to design nucleic acid probes to identify and clone DNA encoding polypeptides having cellobiohydrolase, endoglucanase, cellulolytic enhancing, or xylanase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having cellobiohydrolase, endoglucanase, cellulolytic enhancing, or xylanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45. SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, or SEQ ID NO: 77, the mature polypeptide coding sequence thereof, or a subsequence thereof, the carrier material is used in a Southern blot.

For purposes of the present invention, hybridization indicates that the polynucleotides hybridize to a labeled nucleic acid probe corresponding to (i) SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, or SEQ ID NO: 77; (ii) the polypeptide coding sequence thereof; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is a polynucleotide that encodes the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 74, SEQ ID NO: 76, SEQ ID NO: 78, or SEQ ID NO: 79; the mature polypeptide thereof; or a fragment thereof. In another aspect, the nucleic acid probe is SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, or SEQ ID NO: 77; the mature polypeptide coding sequence thereof; or the cDNA sequence thereof.

In another embodiment, the present invention relates to isolated polypeptides having cellobiohydrolase activity encoded by polynucleotides having at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 1 or SEQ ID NO: 3, or the cDNA sequences thereof; at least 90%, e.g., at least 91%, at least 92%, at least 93%, at least 94%, at least 95%, at least 96%, at least 97%, at least 98%, at least 99%, or 100% sequence identity to the polypeptide coding sequence of SEQ ID NO: 5 or the cDNA sequence thereof; at least 91%, e.g., at least 92%, at least 93%, at least 94%, at least 95%, at least 96%, at least 97%, at least 98%, at least 99%, or 100% sequence identity to the polypeptide coding sequence of SEQ ID NO: 7 or the cDNA sequences thereof; or at least 99%, e.g., 100% sequence identity to the polypeptide coding sequence of SEQ ID NO: 9 or the cDNA sequence thereof.

In another embodiment, the present invention relates to isolated polypeptides having cellobiohydrolase activity encoded by polynucleotides having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence SEQ ID NO: 11 or the cDNA sequence thereof; at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 13 or SEQ ID NO: 15, or the cDNA sequences thereof; at least 91%, e.g., at least 92%, at least 93%, at least 94%, at least 95%, at least 96%, at least 97%, at least 98%, at least 99%, or 100% sequence identity to the polypeptide coding sequence of SEQ ID NO: 17 or the cDNA sequence thereof; at least 96%, e.g., at least 97%, at least 98%, at least 99%, or 100% sequence identity to the polypeptide coding sequence of SEQ ID NO: 19 or the cDNA sequence thereof; or at least 98%, e.g., at least 99% or 100% sequence identity to the polypeptide coding sequence of SEQ ID NO: 21 or SEQ ID NO: 23, or the cDNA sequences thereof.

In another embodiment, the present invention relates to isolated polypeptides having endoglucanase activity encoded by polynucleotides having at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 25 or the cDNA sequence thereof; at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 27 or the cDNA sequence thereof; at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 29 or SEQ ID NO: 31, or the cDNA sequences thereof; at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 33, SEQ ID NO: 35, or SEQ ID NO: 37, or the cDNA sequences thereof; at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 39 or SEQ ID NO: 41, or the cDNA sequences thereof; at least 97%, e.g., at least 98%, at least 99%, or 100% sequence identity to the polypeptide coding sequence of SEQ ID NO: 43 or the cDNA sequence thereof; or at least 98%, e.g., at least 99% or 100% sequence identity to the polypeptide coding sequence of SEQ ID NO: 45 or the cDNA sequence thereof.

In another embodiment, the present invention relates to isolated polypeptides having cellulolytic enhancing activity encoded by polynucleotides having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 47 or the cDNA sequence thereof; at least 75%, e.g., at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 49, SEQ ID NO: 51, or SEQ ID NO: 53, or the cDNA sequences thereof; at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 55, SEQ ID NO: 57, SEQ ID NO: 59, SEQ ID NO: 61, or SEQ ID NO: 63, or the cDNA sequences thereof; at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 65 or the cDNA sequence thereof; or at least 90%, e.g., at least 91%, at least 92%, at least 93%, at least 94%, at least 95%, at least 96%, at least 97%, at least 98%, at least 99%, or 100% sequence identity to the polypeptide coding sequence of SEQ ID NO: 67, SEQ ID NO: 69, or SEQ ID NO: 71, or the cDNA sequences thereof.

In another embodiment, the present invention relates to isolated polypeptides having xylanase activity encoded by polynucleotides having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 73 or the cDNA sequence thereof, at least 94%, e.g., at least 95%, at least 96%, at least 97%, at least 98%, at least 99%, or 100% sequence identity to the polypeptide coding sequence of SEQ ID NO: 77 or the cDNA sequence thereof, or at least 98%, e.g., at least 99% or 100% sequence identity to the polypeptide coding sequence of SEQ ID NO: 75 or the cDNA sequence thereof.

In another embodiment, the present invention relates to variants comprising the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 74, SEQ ID NO: 76, SEQ ID NO: 78, or SEQ ID NO: 79 comprising a substitution, deletion, and/or insertion at one or more (e.g., several) positions. In an embodiment, the number of amino acid substitutions, deletions and/or insertions introduced into the polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 74, SEQ ID NO: 76, SEQ ID NO: 78, or SEQ ID NO: 79 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, AlaNal, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, or the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for cellobiohydrolase, endoglucanase, cellulolytic enhancing, or xylanase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

A polypeptide of the present invention may be a hybrid polypeptide in which a region of one polypeptide is fused at the N-terminus or the C-terminus of a region of another polypeptide.

A polypeptide of the present invention may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

In one embodiment, a cellulose-degrading polypeptide of the present invention may be functionally stable over a temperature of up to 120° C., in particular up to 100° C. in particular up to 80° C., in particular up to 70° C., in particular up to 60° C. more particularly up to 50° C.

In another embodiment, a cellulose-degrading polypeptide of the present invention may exhibit optimum substrate hydrolysis or substrate hydrolysis enhancing activity at a temperature within the range from about 10° C. to about 90° C., such as about 10° C. to about 80° C., particularly in the range from about 20° C. to about 60° C. or about 50° C. to about 80° C.

In another embodiment, a cellulose-degrading polypeptide of the present invention may exhibit optimum substrate hydrolysis or substrate hydrolysis enhancing activity at a pH within the range from about pH 2 to about 10, such as about 3 to about 9, particularly in the range from about 4 to about 8 or about 5 to about 7.

In another embodiment, a cellulose-degrading polypeptide of the present invention enhances the hydrolysis of a cellulosic material in combination with other enzymes having cellulolytic activity.

Sources of Polypeptides Having Cellulolytic or Hemicellulolytic Activity

A polypeptide having cellobiohydrolase, endoglucanase, cellulolytic enhancing, or xylanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly. In another aspect, the polypeptide may be obtained from a microorganism such as a prokaryotic cell, an archaeal cell or a eukaryotic cell. In another aspect, the polypeptide may be synthetically made, naturally occurring, or a combination thereof.

In another aspect, the polypeptide is a *Chaetomium* polypeptide. In another aspect, the polypeptide is a *Chaetomium senegalense* polypeptide. In another aspect, the polypeptide is a *Chaetomium thermophilum* polypeptide.

In another aspect, the polypeptide is a *Corynascus* polypeptide. In another aspect, the polypeptide is a *Corynascus thermophilus* polypeptide.

In another aspect, the polypeptide is a *Malbranchea* polypeptide. In another aspect, the polypeptide is a *Malbranchea cinnamomea* polypeptide.

In another aspect, the polypeptide is a *Melanocarpus* polypeptide. In another aspect, the polypeptide is a *Melanocarpus albomyces* polypeptide.

In another aspect, the polypeptide is a *Remersonia* polypeptide. In another aspect, the polypeptide is a *Remersonia thermophila* polypeptide.

In another aspect, the polypeptide is a *Rhizomucor* polypeptide. In another aspect, the polypeptide is a *Rhizomucor miehei* polypeptide.

In another aspect, the polypeptide is a *Scytalidium* polypeptide. In another aspect, the polypeptide is a *Scytalidium indonesiacum* polypeptide.

In another aspect, the polypeptide is a *Talaromyces* polypeptide. In another aspect, the polypeptide is a *Talaromyces byssochlamydoides* polypeptide. In another aspect, the polypeptide is a *Talaromyces emersonii* polypeptide. In another aspect, the polypeptide is a *Talaromyces leycettanus* polypeptide. In another aspect, the polypeptide is a *Talaromyces thermophilus* polypeptide.

In another aspect, the polypeptide is a *Thermoascus* polypeptide. In another aspect, the polypeptide is a *Thermoascus aurantiacus* polypeptide.

In another aspect, the polypeptide is a *Thermomyces* polypeptide. In another aspect, the polypeptide is a *Thermomyces lanuginosus* polypeptide.

In another aspect, the polypeptide is a *Thermomucor* polypeptide. In another aspect, the polypeptide is a *Thermomucor indicae-seudaticae* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Chaetomium, Corynascus, Malbranchea, Melanocarpus, Remersonia, Scytalidium, Talaromyces, Thermomyces,* or *Thermomucor*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, or SEQ ID NO: 77, or the cDNA sequences thereof, by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

In an embodiment, the polynucleotides of the present invention are selected from a DNA, cDNA, or RNA. The nucleotide sequence may be obtained by standard cloning procedures used in genetic engineering to relocate the nucleotide sequence from its natural location to a different site where it will be reproduced. The cloning procedures may involve excision and isolation of a desired fragment comprising the nucleotide sequence encoding the polypeptide, insertion of the fragment into a vector molecule, and incorporation of the recombinant vector into a host cell where multiple copies or clones of the nucleotide sequence will be replicated. The nucleotide sequence may be of genomic, cDNA, RNA, semisynthetic, synthetic origin, or any combinations thereof.

In another embodiment, the polynucleotides of the present invention belong to the GH6, GH7, GH10, GH45 and GH61 families of glucosyl hydrolases. In the present invention the nucleotide sequence was obtained by generating libraries of known GH6, GH7, GH10, GH45 and GH61 glucosyl hydrolases and running an algorithm that can identify conserved peptide sequences, also called n-mers such as conserved hexapeptides. Such an algorithm includes the following steps: for each biopolymer make all the n-mers that occur in the biopolymer sequence, select all biopolymer that contain more than a defined number of the n-mers, make all the n-mers that occur in these biopolymers and a defined number of the most abundant n-mers, go back to step 2 until no new n-mers are made in the following round. The algorithm is exemplified in Example 1 of the present invention and can for example be used to identify conserved peptides in for example gene families or subgroup of gene families.

Practical testing has shown that a stretch of at least six conserved amino acids is necessary for design of functional primers for degenerate PCR from genomic DNA or cDNA (Sambrook and Russell, 2001, *Molecular Cloning: A Laboratory Manual*, Third Edition, Cold Spring Harbor, New York). On the other hand it can be difficult to find conserved amino acid sequences that are longer than six residues when working with large or very divergent protein families. Therefore, a way to analyze a protein family in order to find conserved peptides than can be used for design of degenerated primers is to identify the most frequently occurring hexapeptides in the family. Conserved hexapeptides were reverse translated according to the genetic code and positions containing any nucleotide (A, C, G or T) were substituted with inosine. Degenerate nucleotides at the 3' end of the primers were removed from the sequence of the primers. The degeneracy of the primer that resulted from reverse translation of each hexapeptide was calculated based on the genetic code and substituting positions containing any nucleotide (A, C, G or T) with inosine. In addition, the relative position of the hexapeptides in the proteins was estimated as the median of the distance of the peptide to the N-terminal of each protein in the subgroup that contained the peptide.

Sequences for primers were selected based on three criteria: they should have high frequency in the GH gene family, they should give an amplicon of at least 40 base pairs excluding primer sequences in order to obtain sufficient sequence information to identify the PCR product, and the primers should have the smallest possible redundancy and redundant bases at the 3' end are not allowed. A tail of six bases (CTG-GAC) was added to the 5' end of all primer sequences as this improves the performance of short primers. Reverse primers were designed to be complementary to the DNA sequence encoding the hexapeptide and according to the same rules and PCR from DNA of different microorganisms amplified and sequence analyzed. Detailed explanations of this approach are described herein in the Examples of the present invention.

In another embodiment, a polynucleotide of the present invention may be isolated from or produced on the basis of a DNA library from a prokaryote, such as a bacterium or an eukaryote, such as a fungus or yeast.

In another embodiment, a polynucleotide of the present invention may be isolated from a fungus that degrades carbohydrates, such as cellulosic substrates. Such fungi include, e.g., Ascomycota, Basidiomycota, Zygomycota or Oomycota.

Nucleic Acid Constructs

The present invention also relates to nucleic acid constructs comprising a polynucleotide of the present invention operably linked to one or more (e.g., several) control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff at al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert at al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more (e.g., several) convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more (e.g., several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, METS, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is a hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more (e.g., several) control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus*, *Clostridium*, *Enterococcus*, *Geobacillus*, *Lactobacillus*, *Lactococcus*, *Oceanobacillus*, *Staphylococcus*, *Streptococcus*, and *Streptomyces*. Gram-negative bacteria include, but are not limited to, *Campylobacter*, *E. coli*, *Flavobacterium*, *Fusobacterium*, *Helicobacter*, *Ilyobacter*, *Neisseria*, *Pseudomonas*, *Salmonella*, and *Ureaplasma*.

The bacterial host cell may be any *Bacillus* cell including, but not limited to, *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis* cells.

The bacterial host cell may also be any *Streptococcus* cell including, but not limited to, *Streptococcus equisimilis*, *Streptococcus pyogenes*, *Streptococcus uberis*, and *Streptococcus equi* subsp. *Zooepidemicus* cells.

The bacterial host cell may also be any *Streptomyces* cell including, but not limited to, *Streptomyces achromogenes*, *Streptomyces avermitilis*, *Streptomyces coelicolor*, *Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomy-* ces, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen at al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and (b) recovering the polypeptide.

In one aspect, the cell is a *Chaetomium* cell. In another aspect, the cell is a *Chaetomium senegalense* cell. In another aspect, the cell is a *Chaetomium thermophilum* cell.

In another aspect, the cell is a *Corynascus* cell. In another aspect, the cell is a *Corynascus thermophilus* cell.

In another aspect, the cell is a *Malbranchea* cell. In another aspect, the cell is a *Malbranchea cinnamomea* cell.

In another aspect, the cell is a *Melanocarpus* cell. In another aspect, the cell is a *Melanocarpus albomyces* cell.

In another aspect, the cell is a *Remersonia* cell. In another aspect, the cell is a *Remersonia thermophila* cell.

In another aspect, the cell is a *Rhizomucor* cell. In another aspect, the cell is a *Rhizomucor miehei* cell.

In another aspect, the cell is a *Scytalidium* cell. In another aspect, the cell is a *Scytalidium indonesiacum* cell.

In another aspect, the cell is a *Talaromyces* cell. In another aspect, the cell is a *Talaromyces byssochlamydoides* cell. In another aspect, the cell is a *Talaromyces emersonii* cell. In another aspect, the cell is a *Talaromyces leycettanus* cell. In another aspect, the cell is a *Talaromyces thermophilus* cell.

In another aspect, the cell is a *Thermoascus* cell. In another aspect, the cell is a *Thermoascus aurantiacus* cell.

In another aspect, the cell is a *Thermomyces* cell. In another aspect, the cell is a *Thermomyces lanuginosus* cell.

In another aspect, the cell is a *Thermomucor* cell. In another aspect, the cell is a *Thermomucor indicae-seudaticae* cell.

The present invention also relates to methods of producing a polypeptide of the present invention, comprising (a) cultivating a recombinant host cell of the present invention under conditions conducive for production of the polypeptide; and (b) recovering the polypeptide.

The cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, the whole fermentation broth is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Plants

The present invention also relates to isolated plants, e.g., a transgenic plant, plant part, or plant cell, comprising a polynucleotide of the present invention so as to express and produce a polypeptide in recoverable quantities. The polypeptide may be recovered from the plant or plant part. Alternatively, the plant or plant part containing the polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilization of the invention are also considered plant parts, e.g., embryos, endosperms, aleurone and seed coats.

Also included within the scope of the present invention are the progeny of such plants, plant parts, and plant cells.

The transgenic plant or plant cell expressing the polypeptide may be constructed in accordance with methods known in the art. In short, the plant or plant cell is constructed by incorporating one or more expression constructs encoding the polypeptide into the plant host genome or chloroplast genome and propagating the resulting modified plant or plant cell into a transgenic plant or plant cell.

The expression construct is conveniently a nucleic acid construct that comprises a polynucleotide encoding a polypeptide operably linked with appropriate regulatory sequences required for expression of the polynucleotide in the plant or plant part of choice. Furthermore, the expression construct may comprise a selectable marker useful for identifying plant cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed.

For instance, the expression of the gene encoding a polypeptide may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, or the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant Cell Physiol.* 39: 885-889), a *Vicia faba* promoter from the legumin B4 and the unknown seed protein gene from *Vicia faba* (Conrad et al., 1998, *J. Plant Physiol.* 152: 708-711), a promoter from a seed oil body protein (Chen et al., 1998, *Plant Cell Physiol.* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiol.* 102: 991-1000), the *chlorella* virus adenine methyltransferase gene promoter (Mitra and Higgins, 1994, *Plant Mol. Biol.* 26: 85-93), the aldP gene promoter from rice (Kagaya et al., 1995, *Mol. Gen. Genet.* 248: 668-674), or a wound inducible promoter such as the potato pin2 promoter (Xu et al., 1993, *Plant Mol. Biol.* 22: 573-588). Likewise, the promoter may be induced by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide in the plant. For instance, the promoter enhancer element may be an intron that is placed between the promoter and the polynucleotide encoding a polypeptide. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

*Agrobacterium tumefaciens*-mediated gene transfer is a method for generating transgenic dicots (for a review, see Hooykas and Schilperoort, 1992, *Plant Mol. Biol.* 19: 15-38) and for transforming monocots, although other transformation methods may be used for these plants. A method for generating transgenic monocots is particle bombardment (microscopic gold or tungsten particles coated with the transforming DNA) of embryonic calli or developing embryos (Christou, 1992, *Plant J.* 2: 275-281; Shimamoto, 1994, *Curr. Opin. Biotechnol.* 5: 158-162; Vasil et al., 1992, *Bio/Technology* 10: 667-674). An alternative method for transformation of monocots is based on protoplast transformation as described by Omirulleh et al., 1993, *Plant Mol. Biol.* 21: 415-428. Additional transformation methods include those described in U.S. Pat. Nos. 6,395,966 and 7,151,204 (both of which are herein incorporated by reference in their entirety).

Following transformation, the transformants having incorporated the expression construct are selected and regenerated into whole plants according to methods well known in the art. Often the transformation procedure is designed for the selective elimination of selection genes either during regeneration or in the following generations by using, for example, co-transformation with two separate T-DNA constructs or site specific excision of the selection gene by a specific recombinase.

In addition to direct transformation of a particular plant genotype with a construct of the present invention, transgenic plants may be made by crossing a plant having the construct to a second plant lacking the construct. For example, a construct encoding a polypeptide can be introduced into a particular plant variety by crossing, without the need for ever directly transforming a plant of that given variety. Therefore, the present invention encompasses not only a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention. Crossing results in the introduction of a transgene into a plant line by cross pollinating a starting line with a donor plant line. Non-limiting examples of such steps are described in U.S. Pat. No. 7,151,204.

Plants may be generated through a process of backcross conversion. For example, plants include plants referred to as a backcross converted genotype, line, inbred, or hybrid.

Genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

The present invention also relates to methods of producing a polypeptide of the present invention comprising (a) cultivating a transgenic plant or a plant cell comprising a polynucleotide encoding the polypeptide under conditions conducive for production of the polypeptide; and (b) recovering the polypeptide.

Removal or Reduction of Cellulolytic or Hemicellulolytic Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of the polynucleotide using methods well known in the art, for example, insertions, disruptions, replacements, or deletions. In a preferred aspect, the polynucleotide is inactivated. The polynucleotide to be modified or inactivated may be, for example, the coding region or a part thereof essential for activity, or a regulatory element required for expression of the coding region. An example of such a regulatory or control sequence may be a promoter sequence or a functional part thereof, i.e., a part that is sufficient for affecting expression of the polynucleotide. Other control sequences for possible modification include, but are not limited to, a leader, polyadenylation sequence, propeptide sequence, signal peptide sequence, transcription terminator, and transcriptional activator.

Modification or inactivation of the polynucleotide may be performed by subjecting the parent cell to mutagenesis and selecting for mutant cells in which expression of the polynucleotide has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the polynucleotide may be accomplished by insertion, substitution, or deletion of one or more nucleotides in the gene or a regulatory element required for transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the polynucleotide to be modified, it is preferred that the modification be performed in vitro as exemplified below.

An example of a convenient way to eliminate or reduce expression of a polynucleotide is based on techniques of gene replacement, gene deletion, or gene disruption. For example, in the gene disruption method, a nucleic acid sequence corresponding to the endogenous polynucleotide is mutagenized in vitro to produce a defective nucleic acid sequence that is then transformed into the parent cell to produce a defective gene. By homologous recombination, the defective nucleic acid sequence replaces the endogenous polynucleotide. It may be desirable that the defective polynucleotide also encodes a marker that may be used for selection of transformants in which the polynucleotide has been modified or destroyed. In an aspect, the polynucleotide is disrupted with a selectable marker such as those described herein.

The present invention also relates to methods of inhibiting the expression of a polypeptide having cellobiohydrolase, endoglucanase, cellulolytic enhancing, or xylanase activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA for inhibiting transcription. In another preferred aspect, the dsRNA is micro RNA for inhibiting translation.

The present invention also relates to such double-stranded RNA (dsRNA) molecules, comprising a portion of the polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, or SEQ ID NO: 77 for inhibiting expression of the polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using a dsRNAi of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art; see, for example, U.S. Pat. Nos. 6,489,127; 6,506,559; 6,511,824; and 6,515,109.

The present invention further relates to a mutant cell of a parent cell that comprises a disruption or deletion of a polynucleotide encoding the polypeptide or a control sequence thereof or a silenced gene encoding the polypeptide, which results in the mutant cell producing less of the polypeptide or no polypeptide compared to the parent cell.

The polypeptide-deficient mutant cells are particularly useful as host cells for expression of native and heterologous polypeptides. Therefore, the present invention further relates to methods of producing a native or heterologous polypeptide, comprising (a) cultivating the mutant cell under conditions conducive for production of the polypeptide; and (b) recovering the polypeptide. The term "heterologous polypeptides" means polypeptides that are not native to the host cell, e.g., a variant of a native protein. The host cell may comprise more than one copy of a polynucleotide encoding the native or heterologous polypeptide.

The methods used for cultivation and purification of the product of interest may be performed by methods known in the art.

The methods of the present invention for producing an essentially cellobiohydrolase, endoglucanase, cellulolytic enhancing, or xylanase-free product is of particular interest in the production of eukaryotic polypeptides, in particular fungal proteins such as enzymes. The cellobiohydrolase, endoglucanase, cellulolytic enhancing, or xylanase-deficient cells may also be used to express heterologous proteins of pharmaceutical interest such as hormones, growth factors, receptors, and the like. The term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from cellobiohydrolase, endoglucanase, cellulolytic enhancing, or xylanase activity that is produced by a method of the present invention.

Compositions

The present invention also relates to compositions comprising a polypeptide of the present invention. Preferably, the compositions are enriched in such a polypeptide. The term "enriched" indicates that the cellobiohydrolase, endoglucanase, cellulolytic enhancing, or xylanase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) additional enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

The compositions may be prepared in accordance with methods known in the art and may be in the form of a liquid or a dry composition. The compositions may be stabilized in accordance with methods known in the art.

In one embodiment, the composition further comprises one or more enzymes selected from the group consisting of one or more (e.g., several) xylanases, mannanases, glucanases, cellulases, lipases, esterases, proteases, endoglycosidases, endo-beta-1,4-glucanases, beta-glucanases, endo-beta-1,3(4)-glucanases, cutinases, peroxidases, catalases, laccases, amylases, glucoamylases, pectinases, reductases, oxidases, phenoloxidases, ligninases, pullulanases, arabinanases, hemicellulases, mannanases, xyloglucanases, xylanases, mannanases, glucanases, pectin acetyl esterases, rhamnogalacturonan acetyl esterases, polygalacturonases, rhamnogalacturonases, galactanases, pectin lyases, pectin methylesterases, and transglutaminases.

The compositions may be prepared in accordance with methods known in the art and may have any physical appearance such as liquid, paste or solid. For instance, the polypeptide composition may be formulated using methods known to the art of formulating enzymes and/or pharmaceutical products, e.g., into coated or uncoated granules or micro granules. The polypeptide to be included in the composition may be stabilized in accordance with methods known in the art, e.g., by stabilizing the polypeptide in the composition by adding an antioxidant or reducing agent to limit oxidation or the polypeptide may be stabilized by adding polymers such as PVP, PVA, PEG or other suitable polymers known to be beneficial to the stability of polypeptides in solid or liquid compositions.

The compositions may be a fermentation broth formulation or a cell composition, as described herein. Consequently, the present invention also relates to fermentation broth formulations and cell compositions comprising a polypeptide having cellobiohydrolase, endoglucanase, cellulolytic enhancing, or xylanase activity of the present invention. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or non-viable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compostions may further comprise a preservative and/or anti-microbial (e.g., bacteriostatic) agent, including, but not limited to, sorbitol, sodium chloride, potassium sorbate, and others known in the art.

The cell-killed whole broth or composition may further comprise one or more enzyme activities such as acetylxylan esterase, alpha-arabinofuranosidase, alpha-galactosidase, alpha-glucuronidase, amylase, arabinanase, arabinofuranosidase, beta-galactosidase, beta-glucosidase, cellobiohydrolase, endoglucanase, endo-beta-1,3(4)-glucanase, ferrulic acid esterase, galactanase, glucoamylase, glucohydrolase, hybrid peroxidases, with combined properties of lignin peroxidases and manganese-dependent peroxidases, laccase, lignin peroxidase, manganese-dependent peroxidases, mannanase, mannan acetyl esterase, mannosidase, pectate lyase, pectin acetyl esterase, pectinase lyase, pectin methyl esterase, polygalacturonase, protease, rhamnogalacturonan lyase, rhamnogalacturonan acetyl esterase, rhamnogalacturonase, xylanase, xylogalacturonosidase, xylogalacturonase, xyloglucanase, and xylosidase.

In some embodiments, the cell-killed whole broth or composition includes cellulolytic enzymes including, but not limited to, (i) endoglucanases (EG) or 1,4-D-glucan-4-glucanohydrolases (EC 3.2.1.4), (ii) exoglucanases, including 1,4-D-glucan glucanohydrolases (also known as cellodextnnases) (EC 3.2.1.74) and 1,4-D-glucan cellobiohydrolases (exo-cellobiohydrolases, CBH) (EC 3.2.1.91), and (iii) beta-glucosidase (BG) or beta-glucoside glucohydrolases (EC 3.2.1.21).

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Examples are given below of preferred uses of the compositions of the present invention. The dosage of the composition and other conditions under which the composition is used may be determined on the basis of methods known in the art.

Uses

The present invention is also directed to the following processes for using the polypeptides having cellobiohydrolase, endoglucanase, cellulolytic enhancing, or xylanase activity, or compositions thereof.

The present invention also relates to processes for degrading or converting a cellulosic or xylan-containing material, comprising: treating the cellulosic or xylan-containing material with an enzyme composition in the presence of a polypeptide having cellobiohydrolase, endoglucanase, cellulolytic enhancing, or xylanase activity of the present invention. In one aspect, the processes further comprise recovering the degraded or converted cellulosic or xylan-containing material. Soluble products of degradation or conversion of the cellulosic or xylan-containing material can be separated from insoluble cellulosic or xylan-containing material using a method known in the art such as, for example, centrifugation, filtration, or gravity settling.

The present invention also relates to processes of producing a fermentation product, comprising: (a) saccharifying a cellulosic or xylan-containing material with an enzyme composition in the presence of a polypeptide having cellobiohydrolase, endoglucanase, cellulolytic enhancing, or xylanase activity of the present invention; (b) fermenting the saccharified cellulosic or xylan-containing material with one or more (e.g., several) fermenting microorganisms to produce the fermentation product; and (c) recovering the fermentation product from the fermentation.

The present invention also relates to processes of fermenting a cellulosic or xylan-containing material, comprising: fermenting the cellulosic or xylan-containing material with one or more (e.g., several) fermenting microorganisms, wherein the cellulosic or xylan-containing material is saccharified with an enzyme composition in the presence of a polypeptide having cellobiohydrolase, endoglucanase, cellulolytic enhancing, or xylanase activity of the present invention. In one aspect, the fermenting of the cellulosic or xylan-containing material produces a fermentation product. In another aspect, the processes further comprise recovering the fermentation product from the fermentation.

The present invention also relates to use of a cellulose-degrading polypeptide of the present invention in a detergent composition, in textile finishing processes, purification of polypeptides, for immobilization of active enzymes, for baking, for manufacturing of biofuel, for modification of plant cell walls, or for processing of cellulose fibre.

The processes of the present invention can be used to saccharify the cellulosic or xylan-containing material to fermentable sugars and to convert the fermentable sugars to many useful fermentation products, e.g., fuel, potable ethanol, and/or platform chemicals (e.g., acids, alcohols, ketones, gases, and the like). The production of a desired fermentation product from the cellulosic or xylan-containing material typically involves pretreatment, enzymatic hydrolysis (saccharification), and fermentation.

The processing of the cellulosic or xylan-containing material according to the present invention can be accomplished using methods conventional in the art. Moreover, the processes of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof, can be used in the practicing the processes of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flávio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, 0. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include fluidized bed, upflow blanket, immobilized, and extruder type reactors for hydrolysis and/or fermentation.

Pretreatment.

In practicing the processes of the present invention, any pretreatment process known in the art can be used to disrupt plant cell wall components of the cellulosic or xylan-containing material (Chandra et al., 2007, Substrate pretreatment: The key to effective enzymatic hydrolysis of lignocellulosics?, *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18; Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic or xylan-containing material can also be subjected to particle size reduction, sieving, pre-soaking, wetting, washing, and/or conditioning prior to pretreatment using methods known in the art.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosols pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

The cellulosic or xylan-containing material can be pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic or xylan-containing material is heated to disrupt the plant cell wall components, including lignin, hemicellulose, and cellulose to make the cellulose and other fractions, e.g., hemicellulose, accessible to enzymes. The cellulosic or xylan-containing material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on temperature range and addition of a chemical catalyst. Steam pretreatment allows for relatively high solids loadings, so that the cellulosic or xylan-containing material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical treatment" refers to any chemical pretreatment that promotes the separation and/or release of cellulose, hemicellulose, and/or lignin. Such a pretreatment can convert crystalline cellulose to amorphous cellulose. Examples of suitable chemical pretreatment processes include, for example, dilute acid pretreatment, lime pretreatment, wet oxidation, ammonia fiber/freeze explosion (AFEX), ammonia percolation (APR), ionic liquid, and organosolv pretreatments.

A catalyst such as $H_2SO_4$ or $SO_2$ (typically 0.3 to 5% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic or xylan-containing material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al, 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, sodium hydroxide, lime, wet oxidation, ammonia percolation (APR), and ammonia fiber/freeze explosion (AFEX).

Lime pretreatment is performed with calcium oxide or calcium hydroxide at temperatures of 85-150° C. and residence times from 1 hour to several days (Wyman et al., 2005, *Bioresource Technol.* 96: 1959-1966; Mosier et al., 2005, *Bioresource Technol* 96: 673-686). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol* 64: 139-151; Palonen et al., 2004, *App. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating the cellulosic or xylan-containing material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh at al., 2005, *Appl. Biochem. Biotechnol.* 121: 1133-1141; Teymouri at al., 2005, *Bioresource Technol.* 96: 2014-2018). During AFEX pretreatment cellulose and hemicelluloses remain relatively intact. Lignin-carbohydrate complexes are cleaved.

Organosolv pretreatment delignifies the cellulosic or xylan-containing material by extraction using aqueous ethanol (40-60% ethanol) at 160-200° C. for 30-60 minutes (Pan at al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol* 121: 219-230). Sulphuric acid is usually added as a catalyst. In organosolv pretreatment, the majority of hemicellulose and lignin is removed.

Other examples of suitable pretreatment methods are described by Schell at al., 2003, *Appl. Biochem. and Biotechnol. Vol.* 105-108, p. 69-85, and Mosier et al., 2005, *Bioresource Technology* 96: 673-686, and U.S. Published Application 2002/0164730.

In one aspect, the chemical pretreatment is preferably carried out as a dilute acid treatment, and more preferably as a continuous dilute acid treatment. The acid is typically sulfuric acid, but other acids can also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one aspect, the acid concentration is in the range from preferably 0.01 to 10 wt % acid, e.g., 0.05 to 5 wt % acid or 0.1 to 2 wt % acid. The acid is contacted with the cellulosic or xylan-containing material and held at a temperature in the range of preferably 140-200° C., e.g., 165-190° C., for periods ranging from 1 to 60 minutes.

In another aspect, pretreatment takes place in an aqueous slurry. In preferred aspects, the cellulosic or xylan-containing material is present during pretreatment in amounts preferably between 10-80 wt %, e.g., 20-70 wt % or 30-60 wt %, such as around 40 wt %. The pretreated cellulosic or xylan-containing material can be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment can involve various types of grinding or milling (e.g., dry milling, wet milling, or vibratory ball milling).

The cellulosic or xylan-containing material can be pretreated both physically (mechanically) and chemically. Mechanical or physical pretreatment can be coupled with steaming/steam explosion, hydrothermolysis, dilute or mild acid treatment, high temperature, high pressure treatment, irradiation (e.g., microwave irradiation), or combinations thereof. In one aspect, high pressure means pressure in the range of preferably about 100 to about 400 psi, e.g., about 150 to about 250 psi. In another aspect, high temperature means temperatures in the range of about 100 to about 300° C., e.g., about 140 to about 200° C. In a preferred aspect, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments can be carried out sequentially or simultaneously, as desired.

Accordingly, in a preferred aspect, the cellulosic or xylan-containing material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic or xylan-containing material. Biological pretreatment techniques can involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification.

In the hydrolysis step, also known as saccharification, the cellulosic or xylan-containing material, e.g., pretreated, is hydrolyzed to break down cellulose and/or hemicellulose to fermentable sugars, such as glucose, cellobiose, xylose, xylulose, arabinose, mannose, galactose, and/or soluble oligosaccharides. The hydrolysis is performed enzymatically by an enzyme composition as described herein in the presence of a polypeptide having cellobiohydrolase, endoglucanase, cellulolytic enhancing, or xylanase activity of the present invention. The enzyme components of the compositions can be added simultaneously or sequentially.

Enzymatic hydrolysis is preferably carried out in a suitable aqueous environment under conditions that can be readily determined by one skilled in the art. In one aspect, hydrolysis is performed under conditions suitable for the activity of the enzyme components, i.e., optimal for the enzyme components. The hydrolysis can be carried out as a fed batch or continuous process where the cellulosic or xylan-containing material is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 120 hours, e.g., about 16 to about 72 hours or about 24 to about 48 hours. The temperature is in the range of preferably about 25° C. to about 70° C., e.g., about 30° C. to about 65° C., about 40° C. to about 60° C., or about 50° C. to about 55° C. The pH is in the range of preferably about 3 to about 8, e.g., about 3.5 to about 7, about 4 to about 6, or about 5.0 to about 5.5. The dry solids content is in the range of preferably about 5 to about 50 wt %, e.g., about 10 to about 40 wt % or about 20 to about 30 wt %.

The enzyme compositions can comprise any protein useful in degrading or converting the cellulosic or xylan-containing material.

In one aspect, the enzyme composition comprises or further comprises one or more (e.g., several) proteins selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin. In another aspect, the cellulase is preferably one or more (e.g., several) enzymes selected from the group consisting of an endoglucanase, a cellobiohydrolase, and a beta-glucosidase. In another aspect, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In another aspect, the enzyme composition comprises one or more (e.g., several) cellulolytic enzymes. In another aspect, the enzyme composition comprises or further comprises one or more (e.g., several) hemicellulolytic enzymes. In another aspect, the enzyme composition comprises one or more (e.g., several) cellulolytic enzymes and one or more (e.g., several) hemicellulolytic enzymes. In another aspect, the enzyme composition comprises one or more (e.g., several) enzymes selected from the group of cellulolytic enzymes and hemicellulolytic enzymes. In another aspect, the enzyme composition comprises an endoglucanase. In another aspect, the enzyme composition comprises a cellobiohydrolase. In another aspect, the enzyme composition comprises a beta-glucosidase. In another aspect, the enzyme composition comprises a polypeptide having cellulolytic enhancing activity. In another aspect, the enzyme composition comprises an endoglucanase and a polypeptide having cellulolytic enhancing activity. In another aspect, the enzyme composition comprises a cellobiohydrolase and a polypeptide having cellulolytic enhancing activity. In another aspect, the enzyme composition comprises a beta-glucosidase and a polypeptide having cellulolytic enhancing activity. In another aspect, the enzyme composition comprises an endoglucanase and a cellobiohydrolase. In another aspect, the enzyme composition comprises an endoglucanase and a beta-glucosidase. In another aspect, the enzyme composition comprises a cellobiohydrolase and a beta-glucosidase. In another aspect, the enzyme composition comprises an endoglucanase, a cellobiohydrolase, and a polypeptide having cellulolytic enhancing activity. In another aspect, the enzyme composition comprises an endoglucanase, a beta-glucosidase, and a polypeptide having cellulolytic enhancing activity. In another aspect, the enzyme composition comprises a cellobiohydrolase, a beta-glucosidase, and a polypeptide having cellulolytic enhancing activity. In another aspect, the enzyme composition comprises an endoglucanase, a cellobiohydrolase, and a beta-glucosidase. In another aspect, the enzyme composition comprises an endoglucanase, a cellobiohydrolase, a beta-glucosidase, and a polypeptide having cellulolytic enhancing activity.

In another aspect, the enzyme composition comprises an acetylmannan esterase. In another aspect, the enzyme composition comprises an acetylxylan esterase. In another aspect, the enzyme composition comprises an arabinanase (e.g., alpha-L-arabinanase). In another aspect, the enzyme composition comprises an arabinofuranosidase (e.g., alpha-L-arabinofuranosidase). In another aspect, the enzyme composition comprises a coumaric acid esterase. In another aspect, the enzyme composition comprises a feruloyl esterase. In another aspect, the enzyme composition comprises a galactosidase (e.g., alpha-galactosidase and/or beta-galactosidase). In another aspect, the enzyme composition comprises a glucuronidase (e.g., alpha-D-glucuronidase). In another aspect, the enzyme composition comprises a glucuronoyl esterase. In another aspect, the enzyme composition comprises a mannanase. In another aspect, the enzyme composition comprises a mannosidase (e.g., beta-mannosidase). In another aspect, the enzyme composition comprises a xylanase. In a preferred aspect, the xylanase is a Family 10 xylanase. In another aspect, the enzyme composition comprises a xylosidase (e.g., beta-xylosidase).

In another aspect, the enzyme composition comprises an esterase. In another aspect, the enzyme composition comprises an expansin. In another aspect, the enzyme composition comprises a laccase. In another aspect, the enzyme composition comprises a ligninolytic enzyme. In a preferred aspect, the ligninolytic enzyme is a manganese peroxidase. In another preferred aspect, the ligninolytic enzyme is a lignin peroxidase. In another preferred aspect, the ligninolytic enzyme is a $H_2O_2$-producing enzyme. In another aspect, the enzyme composition comprises a pectinase. In another aspect, the enzyme composition comprises a peroxidase. In another aspect, the enzyme composition comprises a protease. In another aspect, the enzyme composition comprises a swollenin In the processes of the present invention, the enzyme(s) can be added prior to or during saccharification, saccharification and fermentation, or fermentation.

One or more (e.g., several) components of the enzyme composition may be wild-type proteins, recombinant proteins, or a combination of wild-type proteins and recombinant proteins. For example, one or more (e.g., several) components may be native proteins of a cell, which is used as a host cell to express recombinantly one or more (e.g., several) other components of the enzyme composition. One or more (e.g., several) components of the enzyme composition may be produced as monocomponents, which are then combined to form the enzyme composition. The enzyme composition may be a combination of multicomponent and monocomponent protein preparations.

The enzymes used in the processes of the present invention may be in any form suitable for use, such as, for example, a fermentation broth formulation or a cell composition, a cell lysate with or without cellular debris, a semi-purified or purified enzyme preparation, or a host cell as a source of the enzymes. The enzyme composition may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The optimum amounts of the enzymes and polypeptides having cellobiohydrolase, endoglucanase, cellulolytic enhancing, or xylanase activity depend on several factors including, but not limited to, the mixture of cellulolytic and/or hemicellulolytic enzyme components, the cellulosic or xylan-containing material, the concentration of cellulosic or xylan-containing material, the pretreatment(s) of the cellulosic or xylan-containing material, temperature, time, pH, and inclusion of fermenting organism (e.g., yeast for Simultaneous Saccharification and Fermentation).

In one aspect, an effective amount of cellulolytic or hemicellulolytic enzyme to the cellulosic or xylan-containing material is about 0.5 to about 50 mg, e.g., about 0.5 to about 40 mg, about 0.5 to about 25 mg, about 0.75 to about 20 mg, about 0.75 to about 15 mg, about 0.5 to about 10 mg, or about 2.5 to about 10 mg per g of the cellulosic or xylan-containing material.

In another aspect, an effective amount of a polypeptide having cellobiohydrolase, endoglucanase, cellulolytic enhancing, or xylanase activity to the cellulosic or xylan-containing material is about 0.01 to about 50.0 mg, e.g., about 0.01 to about 40 mg, about 0.01 to about 30 mg, about 0.01 to about 20 mg, about 0.01 to about 10 mg, about 0.01 to about 5 mg, about 0.025 to about 1.5 mg, about 0.05 to about 1.25 mg, about 0.075 to about 1.25 mg, about 0.1 to about 1.25 mg, about 0.15 to about 1.25 mg, or about 0.25 to about 1.0 mg per g of the cellulosic or xylan-containing material.

In another aspect, an effective amount of a polypeptide having cellobiohydrolase, endoglucanase, cellulolytic enhancing, or xylanase activity to cellulolytic or hemicellulolytic enzyme is about 0.005 to about 1.0 g, e.g., about 0.01 to about 1.0 g, about 0.15 to about 0.75 g, about 0.15 to about 0.5 g, about 0.1 to about 0.5 g, about 0.1 to about 0.25 g, or about 0.05 to about 0.2 g per g of cellulolytic or hemicellulolytic enzyme.

The polypeptides having cellulolytic enzyme activity or hemicellulolytic enzyme activity as well as other proteins/polypeptides useful in the degradation of the cellulosic or xylan-containing material, e.g., GH61 polypeptides having cellulolytic enhancing activity (collectively hereinafter "polypeptides having enzyme activity") can be derived or obtained from any suitable origin, including, bacterial, fungal, yeast, plant, or mammalian origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

A polypeptide having enzyme activity may be a bacterial polypeptide. For example, the polypeptide may be a Gram-positive bacterial polypeptide such as a *Bacillus, Streptococcus, Streptomyces, Staphylococcus, Enterococcus, Lactobacillus, Lactococcus, Clostridium, Geobacillus, Caldicellulosiruptor, Acidothermus, Thermobifidia,* or *Oceanobacillus* polypeptide having enzyme activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having enzyme activity.

In one aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having enzyme activity.

In another aspect, the polypeptide is a *Streptococcus equisimilis*, *Streptococcus pyogenes*, *Streptococcus uberis*, or *Streptococcus equi* subsp. *Zooepidemicus* polypeptide having enzyme activity.

In another aspect, the polypeptide is a *Streptomyces achromogenes*, *Streptomyces avermitilis*, *Streptomyces coelicolor*, *Streptomyces griseus*, or *Streptomyces lividans* polypeptide having enzyme activity.

The polypeptide having enzyme activity may also be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having enzyme activity; or more preferably a filamentous fungal polypeptide such as an *Acremonium*, *Agaricus*, *Alternaria*, *Aspergillus*, *Aureobasidium*, *Botryosphaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide having enzyme activity.

In one aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide having enzyme activity.

In another aspect, the polypeptide is an *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia spededonium*, *Thielavia setosa*, *Thielavia subthermophila*, *Thielavia terrestris*, *Trichoderma harzianum*, *Trichoderma koningii*, *Trichoderma longibrachiatum*, *Trichoderma reesei*, *Trichoderma viride*, or *Trichophaea saccata* polypeptide having enzyme activity.

Chemically modified or protein engineered mutants of polypeptides having enzyme activity may also be used.

One or more (e.g., several) components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

In one aspect, the one or more (e.g., several) cellulolytic enzymes comprise a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLUCLAST™ (Novozymes A/S), NOVOZYM™ 188 (Novozymes NS), CELLUZYME™ (Novozymes A/S), CEREFLO™ (Novozymes NS), and ULTRAFLO™ (Novozymes NS), ACCELERASE™ (Genencor Int.), LAMINEX™ (Genencor Int.), SPEZYME™ CP (Genencor Int.), FILTRASE® NL (DSM); METHAPLUS® S/L 100 (DSM), ROHAMENT™ 7069 W (Röhm GmbH), FIBREZYME® LDI (Dyadic International, Inc.), FIBREZYME® LBR (Dyadic International, Inc.), or VISCOSTAR® 150 L (Dyadic International, Inc.). The cellulase enzymes are added in amounts effective from about 0.001 to about 5.0 wt % of solids, e.g., about 0.025 to about 4.0 wt % of solids or about 0.005 to about 2.0 wt % of solids.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovara* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

Examples of cellobiohydrolases useful in the present invention include, but are not limited to, *Aspergillus aculeatus* cellobiohydrolase II (WO 2011/059740), *Chaetomium* thermophilum cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, and *Trichophaea saccata* cellobiohydrolase II (WO 2010/057086).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (WO 2005/047499), *Aspergillus niger* (Dan et al., 2000, *J. Biol. Chem.* 275: 4973-4980), *Aspergillus oryzae* (WO 2002/095014), *Penicillium brasilianum* IBT 20888 (WO 2007/019442 and WO 2010/088387), *Thielavia terrestris* (WO 2011/035029), and *Trichophaea saccata* (WO 2007/019442).

The beta-glucosidase may be a fusion protein. In one aspect, the beta-glucosidase is an *Aspergillus oryzae* beta-glucosidase variant BG fusion protein (WO 2008/057637) or an *Aspergillus oryzae* beta-glucosidase fusion protein (WO 2008/057637.

Other useful endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in WO 98/13465, WO 98/015619, WO 98/015633, WO 99/06574, WO 99/10481, WO 99/025847, WO 99/031255, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. No. 5,457,046, U.S. Pat. No. 5,648,263, and U.S. Pat. No. 5,686,593.

In the processes of the present invention, any GH61 polypeptide having cellulolytic enhancing activity can be used as a component of the enzyme composition.

Examples of GH61 polypeptides having cellulolytic enhancing activity useful in the processes of the present invention include, but are not limited to, GH61 polypeptides from *Thielavia terrestris* (WO 2005/074647, WO 2008/148131, and WO 2011/035027), *Thermoascus aurantiacus* (WO 2005/074656 and WO 2010/065830), *Trichoderma reesei* (WO 2007/089290), *Myceliophthora thermophila* (WO 2009/085935, WO 2009/085859, WO 2009/085864, WO 2009/085868), *Aspergillus fumigatus* (WO 2010/138754), GH61 polypeptides from *Penicillium pinophilum* (WO 2011/005867), *Thermoascus* sp. (WO 2011/039319), *Penicillium* sp. (WO 2011/041397), and *Thermoascus crustaceous* (WO 2011/041504).

In one aspect, the GH61 polypeptide having cellulolytic enhancing activity is used in the presence of a soluble activating divalent metal cation according to WO 2008/151043, e.g., manganese or copper sulfate.

In another aspect, the GH61 polypeptide having cellulolytic enhancing activity is used in the presence of a dioxy compound, a bicyclic compound, a heterocyclic compound, a nitrogen-containing compound, a quinone compound, a sulfur-containing compound, or a liquor obtained from a pretreated cellulosic material such as pretreated corn stover (PCS).

The dioxy compound may include any suitable compound containing two or more oxygen atoms. In some aspects, the dioxy compounds contain a substituted aryl moiety as described herein. The dioxy compounds may comprise one or more (e.g., several) hydroxyl and/or hydroxyl derivatives, but also include substituted aryl moieties lacking hydroxyl and hydroxyl derivatives. Non-limiting examples of the dioxy compounds include pyrocatechol or catechol; caffeic acid; 3,4-dihydroxybenzoic acid; 4-tert-butyl-5-methoxy-1,2-benzenediol; pyrogallol; gallic acid; methyl-3,4,5-trihydroxybenzoate; 2,3,4-trihydroxybenzophenone; 2,6-dimethoxphenol; sinapinic acid; 3,5-dihydroxybenzoic acid; 4-chloro-1,2-benzenediol; 4-nitro-1,2-benzenediol; tannic acid; ethyl gallate; methyl glycolate; dihydroxyfumaric acid; 2-butyne-1,4-diol; (croconic acid; 1,3-propanediol; tartaric acid; 2,4-pentanediol; 3-ethyoxy-1,2-propanediol; 2,4,4'-trihydroxybenzophenone; cis-2-butene-1,4-diol; 3,4-dihydroxy-3-cyclobutene-1,2-dione; dihydroxyacetone; acrolein acetal; methyl-4-hydroxybenzoate; 4-hydroxybenzoic acid; and methyl-3,5-dimethoxy-4-hydroxybenzoate; or a salt or solvate thereof.

The bicyclic compound may include any suitable substituted fused ring system as described herein. The compounds may comprise one or more (e.g., several) additional rings, and are not limited to a specific number of rings unless otherwise stated. In one aspect, the bicyclic compound is a flavonoid. In another aspect, the bicyclic compound is an optionally substituted isoflavonoid. In another aspect, the bicyclic compound is an optionally substituted flavylium ion, such as an optionally substituted anthocyanidin or optionally substituted anthocyanin, or derivative thereof. Non-limiting examples of the bicyclic compounds include epicatechin; quercetin; myricetin; taxifolin; kaempferol; morin; acacetin; naringenin; isorhamnetin; apigenin; cyanidin; cyanin; kuromanin; keracyanin; or a salt or solvate thereof.

The heterocyclic compound may be any suitable compound, such as an optionally substituted aromatic or non-aromatic ring comprising a heteroatom, as described herein. In one aspect, the heterocyclic is a compound comprising an optionally substituted heterocycloalkyl moiety or an optionally substituted heteroaryl moiety. In another aspect, the optionally substituted heterocycloalkyl moiety or optionally substituted heteroaryl moiety is an optionally substituted 5-membered heterocycloalkyl or an optionally substituted 5-membered heteroaryl moiety. In another aspect, the optionally substituted heterocycloalkyl or optionally substituted heteroaryl moiety is an optionally substituted moiety selected from pyrazolyl, furanyl, imidazolyl, isoxazolyl, oxadiazolyl, oxazolyl, pyrrolyl, pyridyl, pyrimidyl, pyridazinyl, thiazolyl, triazolyl, thienyl, dihydrothieno-pyrazolyl, thianaphthenyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, isoindolyl, acridinyl, benzoisazolyl, dimethylhydantoin, pyrazinyl, tetrahydrofuranyl, pyrrolinyl, pyrrolidinyl, morpholinyl, indolyl, diazepinyl, azepinyl, thiepinyl, piperidinyl, and oxepinyl. In another aspect, the optionally substituted heterocycloalkyl moiety or optionally substituted heteroaryl moiety is an optionally substituted furanyl. Non-limiting examples of the heterocyclic compounds include (1,2-dihydroxyethyl)-3,4-dihydroxyfuran-2(5H)-one; 4-hydroxy-5-methyl-3-furanone; 5-hydroxy-2(5H)-furanone; [1,2-dihydroxyethyl]furan-2,3,4(5H)-trione; α-hydroxy-γ-butyrolactone; ribonic γ-lactone; aldohexuronicaldohexuronic acid γ-lactone; gluconic acid δ-lactone; 4-hydroxycoumarin; dihydrobenzofuran; 5-(hydroxymethyl)furfural; furoin; 2(5H)-furanone; 5,6-dihydro-2H-pyran-2-one; and 5,6-dihydro-4-hydroxy-6-methyl-2H-pyran-2-one; or a salt or solvate thereof.

The nitrogen-containing compound may be any suitable compound with one or more nitrogen atoms. In one aspect, the nitrogen-containing compound comprises an amine, imine, hydroxylamine, or nitroxide moiety. Non-limiting examples of the nitrogen-containing compounds include acetone oxime; violuric acid; pyridine-2-aldoxime; 2-aminophenol; 1,2-benzenediamine; 2,2,6,6-tetramethyl-1-piperidinyloxy; 5,6,7,8-tetrahydrobiopterin; 6,7-dimethyl-5,6,7,8-tetrahydropterine; and maleamic acid; or a salt or solvate thereof.

The quinone compound may be any suitable compound comprising a quinone moiety as described herein. Non-limiting examples of the quinone compounds include 1,4-benzoquinone; 1,4-naphthoquinone; 2-hydroxy-1,4-naphthoquinone; 2,3-dimethoxy-5-methyl-1,4-benzoquinone or coenzyme $Q_0$; 2,3,5,6-tetramethyl-1,4-benzoquinone or duroquinone; 1,4-dihydroxyanthraquinone; 3-hydroxy-1-methyl-5,6-indolinedione or adrenochrome; 4-tert-butyl-5-methoxy-1,2-benzoquinone; pyrroloquinoline quinone; or a salt or solvate thereof.

The sulfur-containing compound may be any suitable compound comprising one or more sulfur atoms. In one aspect, the sulfur-containing comprises a moiety selected from thionyl, thioether, sulfinyl, sulfonyl, sulfamide, sulfonamide, sulfonic acid, and sulfonic ester. Non-limiting examples of the sulfur-containing compounds include ethanethiol; 2-propanethiol; 2-propene-1-thiol; 2-mercaptoethanesulfonic acid; benzenethiol; benzene-1,2-dithiol; cysteine; methionine; glutathione; cystine; or a salt or solvate thereof.

In one aspect, an effective amount of such a compound described above to cellulosic material as a molar ratio to glucosyl units of cellulose is about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another aspect, an effective amount of such a compound described above is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described herein, and the soluble contents thereof. A liquor for cellulolytic enhancement of a GH61 polypeptide can be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and a GH61 polypeptide during hydrolysis of a cellulosic substrate by a cellulase preparation. The liquor can be separated from the treated material using a method standard in the art, such as filtration, sedimentation, or centrifugation.

In one aspect, an effective amount of the liquor to cellulose is about $10^{-6}$ to about 10 g per g of cellulose, e.g., about $10^{-6}$ to about 7.5 g, about $10^{-6}$ to about 5, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

In one aspect, the one or more (e.g., several) hemicellulolytic enzymes comprise a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), VISCOZYME® (Novozymes A/S), ULTRAFLO® (Novozymes NS), PULPZYME® HC (Novozymes NS), MULTIFECT® Xylanase (Genencor), ACCELLERASE® XY (Genencor), ACCELLERASE® XC (Genencor), ECOPULP® TX-200A (AB Enzymes), HSP 6000 Xylanase (DSM), DEPOL™ 333P (Biocatalysts Limit, Wales, UK), DEPOL™ 740 L. (Biocatalysts Limit, Wales, UK), and DEPOL™ 762P (Biocatalysts Limit, Wales, UK).

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8X212).

Examples of acetylxylan esterases useful in the processes of the present invention include, but are not limited to, acetylxylan esterases from *Aspergillus aculeatus* (WO 2010/108918), *Chaetomium globosum* (Uniprot accession number Q2GWX4), *Chaetomium gracile* (GeneSeqP accession number AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt accession number q7s259), *Phaeosphaeria nodorum* (Uniprot accession number Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases form *Humicola insolens* DSM 1800 (WO 2009/076122), *Neosartorya fischeri* (UniProt Accession number A1D9T4), *Neurospora crassa* (UniProt accession number Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP accession number AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt accession number alcc12), *Aspergillus fumigatus* (SwissProt accession number Q4WW45), *Aspergillus niger* (Uniprot accession number Q96WX9), *Aspergillus terreus* (SwissProt accession number Q0CJP9), *Humicola insolens* (WO 2010/014706), *Penicillium aurantiogriseum* (WO 2009/068565), *Talaromy-*

*ces emersonii* (UniProt accession number Q8X211), and *Trichoderma reesei* (Uniprot accession number Q99024).

The polypeptides having enzyme activity used in the processes of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of an enzyme or protein. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation.

The fermentable sugars obtained from the hydrolyzed cellulosic or xylan-containing material can be fermented by one or more (e.g., several) fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic or xylan-containing material as a result of the pretreatment and enzymatic hydrolysis steps, are fermented to a product, e.g., ethanol, by a fermenting organism, such as yeast. Hydrolysis (saccharification) and fermentation can be separate or simultaneous, as described herein.

Any suitable hydrolyzed cellulosic or xylan-containing material can be used in the fermentation step in practicing the present invention. The material is generally selected based on the desired fermentation product, i.e., the substance to be obtained from the fermentation, and the process employed, as is well known in the art.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Preferred yeast includes strains of *Candida*, *Kluyveromyces*, and *Saccharomyces*, e.g., *Candida sonorensis*, *Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans*, *Clostridium acetobutylicum*, *Clostridium thermocellum*, *Clostridium phytofermentans*, *Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis*, *C. methanosorbosa*, *C. diddensiae*, *C. parapsilosis*, *C. naedodendra*, *C. blankii*, *C. entomophilia*, *C. brassicae*, *C. pseudotropicalis*, *C. boidinii*, *C. utilis*, and *C. scehatae*; *Clostridium*, such as *C. acetobutylicum*, *C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus*, *K. lactis*, *K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*. In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*. In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic or xylan-containing material or hydrolysate and the fermentation is performed for about 8 to about 96 hours, e.g., about 24 to about 60 hours. The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic or xylan-containing material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products:

A fermentation product can be any substance derived from the fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide ($CO$)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

In another preferred aspect, the fermentation product is isoprene.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *App. Biochem. Biotechnol.* 63-65: 435-448.

In another preferred aspect, the fermentation product is polyketide.

Recovery.

The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic or xylan-containing material and purified by conventional methods of distillation. Ethanol with a purity of up to about 96 vol. % can be obtained, which can be used as, for example, fuel ethanol, drinking ethanol, i.e., potable neutral spirits, or industrial ethanol.

The present invention is further described by the following examples that should not be construed as limiting the scope of the invention.

EXAMPLES

Example 1

Computer algorithm for classifying related biopolymers in groups and finding n-mer sequences with a predefined frequency and example of classifying animal proteins with related function and sequence in six separate groups.

Algorithm

The algorithm to be implemented was:
1. For each biopolymer make all the n-mers that occur in the biopolymer sequence.
2. Select all biopolymer that contain more than a defined number of the n-mers.
3. Make all the n-mers that occur in these biopolymers and a defined number of the most abundant n-mers.
4. Go back to step 2 until no new n-mers are made in the following round.

Program

The computer program is written in the Ruby programming language version 1.8.6 and normally executed on a machine with the Microsoft Windows XP version 2002 operative system but can also be executed under other operative systems and would easily be adapted to other versions of Ruby. The computer program is disclosed in the Computer Program Listing Appendix.

The input consists of a text file (".txt" in windows format) containing biopolymer sequences in FASTA format. In the present example the input file is called "six_families.txt" and contains 105 different protein sequences.

"classify_family3.rb" can be opened in a text editor such as notepad, SciTE, wordpad, MSword or other to define a number of parameters. The most frequently used parameters are:

cut_off: The number of selected n-mers that are present in a biopolymer should be larger than this value to include the biopolymer in the group that is defined by the n-mers.

limit: Number of n-mers that are selected based on frequency. E.g.; limit=100 means that the 100 most frequently occurring n-mers will be selected.

pep_length: Length of the n-mers.

The value of these three parameters is listed in lines 1-3 of "classify_family3.rb". Other parameters may be changed, e.g., file names or information written to the log file may be changed.

In the present example the parameters are: cut_off=9 (A protein should contain at least 10 of the selected peptides to be included in the group); limit=100 (The 100 most frequently occurring peptides are selected); and pep_length=6 (The peptides are hexamers (six amino acids long)).

Classes, arrays, methods and other parameters and objects may be named as "amino acid", "peptide", "protein" or similar referring to peptide and amino acid nomenclature but the program works just as well for biopolymers and n-mers consisting of nucleotide sequences.

When executing "classify_family3.rb" the algorithm will generate two output files for each group of biopolymers:

One file ("group_n.txt" where n is an integer) with the selected biopolymers in FASTA format and with the score included in the name line of the sequence (The score is the number of selected n-mers that were found in the protein).

Another file ("group_n_peps.txt" where n is the same integer) with the corresponding selected n-mer sequences listed according to frequence of occurrence (frequency). In addition, the following information about each n-mer is listed:

Position: The median position in the selected biopolymers that contain the n-mer.

Hits: Number of biopolymers in the group that contain the n-mer. This is the same as frequency.

Degeneracy: Number of nucleotide sequences that will encode the n-mer, last nucleotide not included if this position is degenerate, Degeneracy_w_I: Same as degeneracy but with nucleotide positions that can include all four bases (A,C,G,T) substituted with an inosine that is not degenerate.

Degeneracy and degeneracy_w_I are only relevant when the n-mers are peptides. "group_n_peps.txt" is a text file that can be opened as such or opened or imported into MS excel Open Office calc or another spread sheet.

In addition to the files for each group, the program will write selected information about the result to a logfile called "parameter_variation.txt".

In the present example, the information written to the logfile is the date of the run, number of input sequences, values for limit, cut_off and pep_length, number of groups generated, and for each group: Group number, activity of the protein used to generate the first set of hexapeptides for generation of the group and number of proteins included in the group.

Protein Sequences:

The proteins included in the input file (accession numbers: 1705782, 224983391, 224983654, 301757408, 301785071, 296474442, 77736363, 114053227, 115496822, 260789607, 296211128, 296198149, 73997778, 54114982, 145558686, 148231179, 18858509, 113682259, 19880484, 194211581, 198443141, 2506136, 1345958, 193695213, 157115283, 301754163, 312376091, 158299938, 66515350, 60592790, 170587440, 309360367, 268566311, 212642053, 308499509, 73964695, 148841334, 78214939, 170038418, 292619618, 229366888, 225718944, 41152191, 225716152, 57525242, 159159985, 3043445, 225713940, 126302643, 225705832, 149546904, 225706882, 114627636, 226372738, 157817161, 209737752, 148228671, 296487921, 45709387, 45382955, 38512205, 62088936, 291389251, 114644522, 149031929, 5069468, 38511776, 148232916, 260831456, 296215214, 73963109, 292619987, 176866349, 317419553, 4885563, 28557781, 241293326, 22085162, 114653371, 291239731, 47224750, 270010958, 301757916, 209447036, 296203637, 73993349, 73993361, 57104988, 149730179, 224458362, 35920, 4507047, 189053509, 109120366, 4096268, 148673899, 291410388, 114649243, 114649241, 114649245, 55730091, 297693777, 18181964, 6981556 and 60302866) were found in databases provided by the National Center for Biotechnology Information (http://www.ncbi.nlm.nih.gov) by searching for proteins related to the following protein names: "fatty acid synthetases", "cyclin D", "EDF-1", "SP1", "PKC" and "cationic amino acid transporter 1" and sequences related to these names.

Each protein was assigned a number between ">" and "gi" in the name line of the FASTA formatted sequence. The number can be used for manual tracking of the origin of the protein:

Numbers below 100: fatty acid synthetases (FAS)
Numbers between 100 and 200: cyclin D (cycD)
Numbers between 200 and 300: Endothelial Differentiation Factor 1 (EDF-1)
Numbers between 300 and 400: Sp1 transcription factor (SP1)
Numbers between 400 and 500: Protein Kinase C (PKC)
Numbers between 500 and 600: Cationic Amino Acid Transporter 1 (CAT1)

Results

The input file contained animal protein sequences of six different types. Between 11 and 23 proteins sequence of each type were included.

Execution of "classify_family3.rb" classified the proteins into six groups with the corresponding files: "group_1.txt", "group_1_peps.txt", "group_2.txt", "group_2_peps.txt", "group_3.txt", "group_3_peps.txt", "group_4.txt", "group_4_peps.txt", "group_5.txt", "group_5_peps.txt", "group_6.txt", "group_6_peps.txt".

The groups and the sequences were related in the following ways as shown below in

TABLE 1

| Group number | Proteins | Protein accession numbers |
|---|---|---|
| 1 | All (23) CAT1-type proteins | 301757916, 209447036, 296203637, 73993349, 73993361, 57104988, 149730179, 224458362, 35920, 4507047, 189053509, 109120366, 4096268, 148673899, 291410388, 114649243, 114649241, 114649245, 55730091, 297693777, 18181964, 6981556, 60302866 |
| 2 | All (20) FAS-type proteins | 198443141, 2506136, 1345958, 193695213, 157115283, 301754163, 312376091, 158299938, 66515350, 60592790, 170587440, 309360367, 268566311, 212642053, 308499509, 73964695, 148841334, 78214939, 170038418, 292619618 |
| 3 | All (20) cycD-type proteins | 1705782, 224983391, 224983654, 301757408, 301785071, 296474442, 77736363, 114053227, 115496822, 260789607, 296211128, 296198149, 73997778, 54114982, 145558686, 148231179, 18858509, 113682259, 19880484, 194211581 |
| 4 | All (17) EDF1-type proteins | 229366888, 225718944, 41152191, 225716152, 57525242, 159159985, 3043445, 225713940, 126302643, 225705832, 149546904, 225706882, 114627636, 226372738, 157817161, 209737752, 148228671 |
| 5 | All (14) PKC-type proteins | 260831456, 296215214, 73963109, 292619987, 176866349, 317419553, 4885563, 28557781, 241293326, 22085162, 114653371, 291239731, 47224750, 270010958 |
| 6 | All (11) SP1-type proteins | 296487921, 45709387, 45382955, 38512205, 62088936, 291389251, 114644522, 149031929, 5069468, 38511776, 148232916 |

Conclusion

As seen from Table 1, all sequences were classified together with the other proteins of the same type as expected. This result shows that the algorithm executed by "classify_family3.rb" is able to classify many sequences of several different types into functionally related groups. Furthermore, the program provides a library of the most frequently occurring hexapeptides for each group. This library is useful for further characterization of the protein, for generation of degenerated primers or probes or other purposes related to understanding the protein groups.

Example 2

Classification of GH61 Proteins in New Groups

Input Sequences:

Names and sequences of 467 proteins with a glycosyl-hydrolase family 61 domain accession numbers:
74667001, 74623591, 296439555, 262118542, 296439558, 74681380, 166327, 225557038, 150407066, 239612339, 239607981, 261199970, 261202604, 291178704, 296817237, 119403851, 119403039, 119402879, 121706932, 121699858, 121701491, 119401707, 238490450, 220691752, 238497908, 238491658, 238503077, 220700751, 159129837, 159122044, 159123538, 66848476, 70986426, 70994524, 66853425, 70986442, 42820662, 259486007, 67517718, 259480946, 40740355, 40739935, 259479347, 259480639, 259487791, 75859132, 40739882, 259481977, 134082518, 134080048, 145239987, 145258912, 145246562, 145249108, 169772537, 169776393, 169772353, 83766624, 83770187, 83775441, 83774271, 114192450, 114196513, 114192138, 114196092, 114189374, 115385899, 115391767, 115401906, 115433194, 114192785, 115491813, 115401646, 194010899, 157679842, 154319179, 150848256, 150843601, 154291544, 154305677, 154305687, 150846167, 150843791, 154303615, 154321720, 116198863, 116197146, 88180011, 116208464, 116196852, 88179151, 116194372, 88176999, 88175803, 88177898, 116206022, 116208766, 88180297, 116201473, 88184980, 116178904, 88176171, 116193969, 116208324, 88178730, 88178174, 88178872, 116181126, 88182035, 116208244, 88181972, 88184289, 88179554, 88182057, 116195750, 88181172, 116202763, 116199761, 116203843, 116179468, 88178947, 116199201, 88184520, 88177588, 116196738, 116200237, 116199041, 116200816, 116203395, 119183059, 240109478, 23429037, 116503205, 116498049, 116497843, 299742296, 299741430, 116506365, 299744767, 169851646, 299741891, 299742644, 299753892, 169856301, 116506859, 298405205, 299747134, 116500962, 298409438, 169855583, 298408738, 298405278, 169863978, 298404712, 298405412, 169857546, 298408101, 116497409, 298405114, 298408187, 169868872, 169866035, 116504243, 298405932, 169856214, 299754619, 298405923, 134107111, 57223077, 46118057, 46115580, 46119467, 46139947, 46110641, 46115706, 46116252, 46124039, 46127069, 46127267, 46123465, 46123419, 46123661, 209570280, 209570302, 209570284, 209570424, 31747162, 2315274, 170102152, 170092074, 164651300, 164636998, 164642401, 170109392, 164642863, 164642075, 170105517, 170101484, 170105309, 145011373, 145011030, 145020107, 145014411, 145011646, 145015510, 145019304, 145016906, 145017744, 145014077, 145015931, 145021993, 39945800, 39968819, 145603548, 39946206, 149209397, 145608220, 145608962, 39972659, 145607904, 39971969, 39944092, 145605188, 145609409, 238616327, 238615335, 215456441, 238568683, 238587009, 238583365, 238591056, 215461462, 238579289, 238590448, 215458915, 215450835, 215451124, 238587956, 238567983, 238569868, 238579260, 215458309, 238616405, 302911456, 302883424, 302911391, 302888437, 302885549, 256726867, 302890355, 302885390, 302889367, 302887358, 256726596, 256727058, 256726169, 119498947, 119406222, 119485741, 119500958, 119415683, 119481757, 119495445, 119474543, 119481769, 28919725, 28920895, 85118747, 85078092, 28919956, 28924255, 28919596, 28925415, 28920933, 157071792, 85119231, 85107660, 28881165, 18376179, 16945376, 211583790, 255933578, 255945663, 255937397, 212532291, 111056092, 160705691, 160701235, 169617890, 111070506, 160706762, 111061286, 169596753, 160703463, 169596264, 111068298, 160705400, 169616886, 111060360, 160706840, 111065694, 169598246, 169622513, 169598063, 169594960, 169604850, 169608836, 111069743, 160704974, 160701263, 169617193, 111062780, 169619068, 160703254, 21694047, 170936818, 171693009, 171677338, 170939885, 171685476, 170946510, 171679531, 171676648, 170946519, 171680024, 171679531, 170936992, 170942657, 171683179, 171683736, 170945726, 170944138, 171684255, 170941524, 170941094, 170945939, 171694598, 171681337, 171688168, 171692645, 171690944, 171681359, 171683760, 170942722, 171681569, 170942522, 170941813, 170939504, 242218042, 242217378, 220731934, 220723726, 189198079, 187980642, 189199012, 189194773, 189193113, 187983705, 187976621, 187983395, 189201760, 189207084, 189188194, 189200058, 187979887, 189188372, 187977147, 187984916, 189200631, 189192108, 189193871, 189205641, 187972977, 187983372, 189191958, 187979866, 189194025, 302686954, 300103229, 300103287, 300108602, 300101553, 300111682, 302696233, 300105858, 302674513, 300100257, 300103639, 300106070, 302675767, 300101263, 302683644, 302679828, 302682756, 300101194, 300103387, 302677564, 300100552, 300100648, 302689207, 300105576, 302674561, 289620945, 289620832, 289621556, 289615045, 289618715, 289618337, 148553353, 218722209, 284451272, 201066457, 299892806, 302656446, 296418037, 295636680, 237904675, 302409770, 261358989, 302420443, 261361024, 302410193, 261352381, 261358929, 302414852, 302418676, 261360020, 302413657, 302417124, 302405483, 261353895, 302419149, 261358115, 302405803, 261359888, 261359952, 302405821, 261361512, 302409258, 49333361, 238011426, 194704134, and 11359621 were used as input.

Algorithm and Implementation

The same program as in example 1 was used with the parameters cut_off=9, limit=100 and pep_length=6.

Results

The program was executed with the 467 gh61 proteins as input. After 13 rounds the groups became too small (five or less proteins) to define any common peptide profile because the remaining proteins had very different sequences. However, 13 round defined the groups as listed in Table 2. Each group had its own profile of hexapeptides (100 most frequently occurring hexapeptides) with little overlap between groups as illustrated in Table 3.

TABLE 2

Groups of GH61 proteins

| Group | Proteins |
|---|---|
| 1 | 86 |
| 2 | 43 |
| 3 | 27 |
| 4 | 24 |
| 5 | 19 |
| 6 | 18 |
| 7 | 15 |
| 8 | 15 |
| 9 | 14 |
| 10 | 14 |
| 11 | 13 |
| 12 | 10 |
| 13 | 9 |

TABLE 3

Cross comparison of the hexapeptide signatures for each group (group) of GH61 proteins

| Subfamily | 1 | 2 | 3 | 4 | 5 | 6 | 7 | 8 | 9 | 10 | 11 | 12 | 13 |
|---|---|---|---|---|---|---|---|---|---|---|---|---|---|
| 1 | 100 | 3 | 3 | 1 | 0 | 0 | 0 | 5 | 1 | 2 | 3 | 0 | 2 |
| 2 | 3 | 100 | 12 | 0 | 0 | 1 | 1 | 7 | 0 | 5 | 2 | 1 | 4 |
| 3 | 3 | 12 | 100 | 7 | 0 | 2 | 0 | 4 | 2 | 5 | 3 | 0 | 3 |
| 4 | 1 | 0 | 7 | 100 | 0 | 1 | 0 | 0 | 2 | 1 | 0 | 1 | 1 |
| 5 | 0 | 0 | 0 | 0 | 100 | 0 | 0 | 0 | 0 | 0 | 0 | 0 | 0 |
| 6 | 0 | 1 | 2 | 1 | 0 | 100 | 0 | 1 | 6 | 2 | 0 | 0 | 1 |
| 7 | 0 | 1 | 0 | 0 | 0 | 0 | 100 | 0 | 0 | 0 | 3 | 1 | 0 |
| 8 | 5 | 7 | 4 | 0 | 0 | 1 | 0 | 100 | 0 | 3 | 6 | 1 | 2 |
| 9 | 1 | 0 | 2 | 2 | 0 | 6 | 0 | 0 | 100 | 0 | 0 | 0 | 0 |
| 10 | 2 | 5 | 5 | 1 | 0 | 2 | 0 | 3 | 0 | 100 | 2 | 0 | 1 |
| 11 | 3 | 2 | 3 | 0 | 0 | 0 | 3 | 6 | 0 | 2 | 100 | 0 | 1 |
| 12 | 0 | 1 | 0 | 1 | 0 | 0 | 1 | 1 | 0 | 0 | 0 | 100 | 0 |
| 13 | 2 | 4 | 3 | 1 | 0 | 1 | 0 | 2 | 0 | 1 | 1 | 0 | 100 |

300101299, 154700549, 156063440, 154694216, 156050139, 156045950, 154700442, 156039846, 154700551, 156049573, 289621959, 289615175, 289616424, 289621869, 289618672, 289622259, 289614784, 289619034, 289615496, 289618626, 289616197, 289616196, 289617770, 289620809,

Conclusion

The distribution of the hexapeptides showed that almost all the conserved peptides were found in the first 240 amino acids of the gh61 proteins whereas the remaining part of the proteins was highly variable. Interestingly, two peaks were observed where most of the conserved hexapeptides were found for all the family. Region 1 located between amino acid residues 100-120 has a clear peak whereas region 2 (amino acids 160-200) has a shoulder at amino acids 200-240. The distribution of peptides for each group shows that groups 1, 5, 7, 8 9, 10 and 12 (type 1) only have peaks in regions 1 and 2 whereas groups 2, 3, 4, 6, 11 and 13 (type 2) have an additional peak from amino acids 200-220. Peak 1 was very small in group 7, indicating that this group is poorly conserved in region 1.

To investigate the three conserved regions in more detail we aligned the hexapeptides for each group in these regions to generate a consensus sequence. Alignment of the consensus sequences for each group shows that region 1 is similar in 11 of the 13 groups and contains one of the histidines that coordinates the divalent nickel atom bound to the gh61 crystal structure (Karkehabadi, S. et al., 2008. The first structure of a glycoside hydrolase family 61 member, Cel61B from *Hypocrea jecorina*, at 1.6 A resolution. Journal of Molecular Biology, 383(1), 144-154). Furthermore, the two cysteines that form a cysteine bridge in the crystal structure were found in this region but were only conserved in groups 1, 8 and 11. In group 11, the second of the two cysteines was found in the protein sequences but was located outside the conserved hexapeptides.

Region 2 was conserved in all 13 groups and contains a conserved histidine that does not participate in coordination of the nickel atom (Karkehabadi, S. et al., 2008. The first structure of a glycoside hydrolase family 61 member, Cel61B from *Hypocrea jecorina*, at 1.6 A resolution. Journal of Molecular Biology, 383(1), 144-154) but nevertheless is located on the nickel-binding surface of gh61 together with two other conserved residues (Q/E49 and Y51) in region 2. Region 3 is outside the reported crystal structure and contains a conserved proline-glycine dipeptide.

To further compare the groups we aligned the proteins that gave the highest score in each group. Notably, this alignment showed that His23 that participates in binding to the nickel atom was conserved in all families. Also the two cysteines (Cys78 and Cys228) that form a cysteine bridge in the crystal were conserved. Interestingly, the alignment is poor between amino acids 60 and 80 where several residues map to the nickel binding surface of gh61. Thus the herein described algorithm programmed as in example 1 is able to divide a large number of highly divergent gh61 family proteins into comprehensible groups.

Example 3

Generation of Primers to Isolate Novel Genes Belonging to GH61 Group 1 Genes

Design of Degenerated Primers

Conserved hexapeptides identified in example 2 were reverse translated according to the genetic code and positions containing any nucleotide (A, C, G or T) were substituted with inosine (Table 4). Degenerate nucleotides at the 3' end of the primers were removed from the sequence of the primers. The degeneracy of the primer that results from reverse translation of each hexapeptide was calculated based on the genetic code and substituting positions containing any nucleotide (A, C, G or T) with inosine (Table 4). In addition, the relative position of the hexapeptides in the proteins was estimated as the median of the distance of the peptide to the N-terminal of each protein in the subgroup that contained the peptide.

Sequences for primers were selected on three criteria:
1. They should have high frequency in the subfamily of proteins
2. They should give an amplicon of at least 40 base pairs excluding primer sequences in order to be able to get sufficient sequence information to identify the PCR product.
3. The primers should have the smallest possible redundancy and redundant bases at the 3' end are not allowed.

A tail of six bases (CTGGAC) was added to the 5' end of all primer sequences as this is reported to improve the performance of short primers. Reverse primers were designed to be reverse complementary to the DNA sequence encoding the hexapeptide and according to the same rules. The primers were synthesized and HPLC-purified by Sigma-Aldrich (UK/Europe).

TABLE 4

List of degenerated primers

| Peptide | Primer name | Final primer sequence |
|---|---|---|
| DIICHK | 61.1 | CTGGACGAYATHATHTGYCAYAA (SEQ ID NO: 80) |
| EIIALH | 61.2 | CTGGACTGIAGIGCDATDATYTC (SEQ ID NO: 81) |
| HHGPV | 61.3 | CTGGACCAYCAYGGICCIGT (SEQ ID NO: 82) |
| GAQNYP | 61.4 | CTGGACGGRTARTTYTGIGCICC (SEQ ID NO: 83) |
| LEFFKI | 61.5 | CTGGACCTIGARTTYTTYAARAT (SEQ ID NO: 84) |

Fungi

The following fungi as listed in table 6 were purchased from The Centraalbureau voor Schimmelcultures, The Netherlands and grown on 6% wheat bran (Finax, Denmark), 15% agar (Sigma-Aldrich, UK/Europe) plates at the recommended temperature.

TABLE 5

List of fungi

| Fungus | CBS number |
|---|---|
| *Chaetomium senegalense* | 728.84 |
| *Chaetomium thermophilum* | 180.67 |
| *Corynascus thermophilus* | 406.69 |
| *Malbranchea cinnamomea* | 115.68 |
| *Melanocarpus albomyces* | 638.94 |
| Remersonia thermophila | 540.69 |
| *Scytalidium indonesiacum* | 259.81 |
| *Scytalidium thermophilum* | 620.91 |
| *Talaromyces byssochlamydoides* | 151.75 |
| *Talaromyces emersonii* | 393.64 |
| *Talaromyces leycettanus* | 398.68 |
| *Talaromyces thermophilus* | 236.58 |
| *Thermoascus aurantiacus* | 891.70 |
| *Thermomyces lanuginosus* | 632.91 |

DNA Purification

Fungal mycelium was scraped of the top of a wheat bran agar plate, frozen in $N_2(I)$ and grinded with a mortar and pestle. DNA was extracted from the homogenized mycelium with the Fungal DNA Mini Kit (Omega Bio-Tek, USA) according to the manufacturer's instructions.

PCR

A mix of 100 ng total fungal RNA in 1×Run PCR buffer, 2 mM each dATP, dCTP, dGTP and dTTP, 400 nM forward primer; 400 nM reverse primer; 1U RUN DNA polymerase (A&A Biotechnology, Poland) in a total volume of 20 µl was used for PCR on an MyCycler (Bio-Rad, USA) with the following thermal profile: Initial denaturation 95° C., 5 minutes. 40 cycles of 95° C., 20 seconds; 54° C., 30 seconds; 72° C., 60 seconds and a final extension at 72° C. 5 minutes. PCR products were analyzed by agarose gel electrophoresis and selected DNA were cut out and purified using a QIAQUICK® Kit (QIAGEN, Germany). One µl of the purified PCR product was reamplified in a 50 µl reaction under the same conditions as the original PCR except that only 15 to 20 cycles of PCR were performed.

Sequencing and Analysis

PCR products were cycle sequenced by Eurofins-MWG (Germany) or StarSEQ (Germany) with one of the degenerated primers used for PCR. The resulting sequences were translated to amino acid sequence and used for BLAST search (Altschul et al., 1997) against the non-redundant protein sequence database at NCBI and inspected for conserved domains (Marchler-Bauer et al., 2009) in the CDD database at NCBI to identify sequences encoding glycoside hydrolase family 61-like proteins.

Results

The most frequently occurring hexapeptides defining group 1 of GH61s were used for design of degenerated primers (Table 4). As the two most conserved hexapeptides (occurring in 80 and 78% of the proteins) could be used for design of reverse primers we did not find it necessary to design a third reverse primer. One of the three hexapeptides used for forward primer design (SHHGPV) contains one serine residue that is coded by 6 different codons at the N-terminal. A degenerate primer to serine does not contribute significantly to specificity and therefore, the primer was made by reverse translation of the peptide HHGPV. In virtual PCR the three forward and two reverse primers were able to amplify 66 of the 85 proteins in group 1 and no proteins from other groups.

The primers were used for all six possible combinations for PCR of DNA from the 14 thermophilic fungi.

For all the fungi at least one of the primer sets gave an amplification product with the expected size and for some fungi all the primer sets gave a positive product. For each fungus, the longest ampliqon that had the expected size was sequenced and analyzed for open reading frames. All the ampliqons yielded a sequence that encodes a novel, putative GH61 family gene. Although the isolated sequences are only partial, it was possible to classify all except one as belonging to group 1. The unassigned sequence from *Chaetomium senegalense* was the shortest of the sequences and is only 37 amino acids long but had up to 73% identity to known gh61 sequences and 78% identity to the new sequence from *Remersonia thermophila*. In fact, it is surprising that the some of the new sequences had so many of the conserved hexapeptides. E.g.; the partial gh61 sequence from *Malbranchea cinnamomea* had 17 of the conserved peptides from group 1 although the sequence is only 73 amino acids long. In summary, the PCR result showed that degenerated primers based on the hexapeptide finder algorithm could be used to find new gh61 proteins.

Example 4

Generation of Primers to Isolate Novel Genes Belonging to GH6, GH7 and GH45 Genes Using the same approach conserved hexapeptides was identified for the GH6, 7 and 45 families.

Input Sequences:

Names and sequences of: 17 proteins with a glycosyl-hydrolase family 6 domain accession numbers: (119473935, 119495997, 220693815, 70986018, 145239297, 145246118, 115401052, 115491303, 67521632, 67538224, 95025919, 913560, 60729586, 68270848, 50837707, 50837690, 50837696)

19 proteins with a glycosyl-hydrolase family 7 domain accession numbers: (950686, 4883502, 156712278, 156712280, 156712284, 20986705, 27125837, 150021831, 29160357, 117935080, 58045187, 156712282, 50844407, 2761, 950686, 950688, 4883502, 7224903, 29160311)

12 proteins with a glycosyl-hydrolase family 45 domain accession numbers: (154294519, 222103630, 116180480, 310789959, 312217600, 39951371, 169616266, 171687659, 189197649, 27530617, 156032908 and 158138919) were used as input.

Conserved hexapeptides were identified for the 3 gene families as in Example 2 and the below listed degenerate primes were generated and PCR amplification was performed as described in Example 3.

TABLE 6

List of degenerate primes

| Target genes | Target sequence | primer sequence | Target genes | redundancy | name |
|---|---|---|---|---|---|
| GH6 | LPDRDC | caggtccticcigaymgigaytg | GH6 | 512 | CBHII.7 |
| GH6 | GWLGWP | caggtcggitggctiggitggc | GH6 | 64 | CBHII.9 |
| GH6 | GLATNV | caggtcggictigciaciaaygt | GH6 | 512 | CBHII.11 |
| GH6 | PAPEAG | caggtcccigcytciggigcigg | GH6 | 512 | CBHII.6 |
| GH6 | WFQAYF | caggtcaartaigcytgraacca | GH6 | 32 | CBHII.8 |
| GH6 | VVYDLP | ctggacgtigtitaygaycticc | GH6 | 256 | cbhII.13 |
| GH6 | WVKPGG | ctggaccciccigygttiaccca | GH6 | 128 | cbhII.10 |
| GH7 | DANWRW | ctggacgaygciaaytggmgitgg | GH7 | 128 | cbhI.1 |
| GH7 | EFTFDVD | ctggacgarttyacittygaygtiga | GH7 | 256 | cbhI.3 |
| GH7 | GTGYCD | ctggacggiaciggitaytgyga | GH7 | 256 | cbhI.5 |

TABLE 6-continued

List of degenerate primes

| Target genes | Target sequence | primer sequence | Target genes | redundancy | name |
|---|---|---|---|---|---|
| GH7 | EMDIWEA | ctggacgcytcccadatrtccatytc | GH7 | 24 | cbhI.2 |
| GH7 | DGCDFN | ctggacttraartcrcaiccrtc | GH7 | 64 | cbhI.4 |
| GH7 | VVTQF | ctggacaaytgigtiaciac | GH7 | 128 | cbhI.6 |
| GH45 | YWDCCK | caggtctaytgggaytgytgyaa | GH45 | 16 | GH45.3 |
| GH45 | PGGGVG | caggtcociacioccioccigg | GH45 | 1024 | GH45.6 |
| GH45 | WR(F/Y)(D/N)WF | caggtcaaccarttrtaickcca | GH45 | 128 | GH45.8 |
| GH45 | WCCACY | ctggactggtgytgygcitgyta | GH45 | 32 | 45.5 |
| GH45 | WCCACY | ctggactarcaigcrcarcacca | GH45 | 32 | 45.10 |
| GH45 | WDCCKP | ctggactgggaytgytgyaarcc | GH45 | 16 | 45.7 |

Results

By performing PCR amplification of DNA isolated from the 14 fungus listed in Table 5 using combinations of the degenerate primes listed in table 6 and sequence analysis of the resulting amplified DNA fragments lead to the isolation of fragments of 6 novel GH6 genes, 8 novel GH7 genes and 10 novel GH45 genes.

The present invention is further described by the following numbered paragraphs:

[1] An isolated polypeptide having cellobiohydrolase activity, selected from the group consisting of: (a) a polypeptide having at least 80% sequence identity to the polypeptide of SEQ ID NO: 2 or SEQ ID NO: 4; at least 90% sequence identity to the polypeptide of SEQ ID NO: 6; at least 91% sequence identity to the polypeptide of SEQ ID NO: 8; or at least 99% sequence identity to the polypeptide of SEQ ID NO: 10; (b) a polypeptide encoded by a polynucleotide that hybridizes under at least very high stringency conditions with (i) the polypeptide coding sequence of SEQ ID NO: 1, SEQ ID NO: 3, SEQ ID NO: 5, SEQ ID NO: 7, or SEQ ID NO: 9, (ii) the cDNA sequence thereof, or (iii) the full-length complement of (i) or (ii); (c) a polypeptide encoded by a polynucleotide having at least 80% sequence identity to the polypeptide coding sequence of SEQ ID NO: 1 or SEQ ID NO: 3, or the cDNA sequences thereof; at least 90% sequence identity to the polypeptide coding sequence of SEQ ID NO: 5 or the cDNA sequence thereof; at least 91% sequence identity to the polypeptide coding sequence of SEQ ID NO: 7 or the cDNA sequences thereof; or at least 99% sequence identity to the polypeptide coding sequence of SEQ ID NO: 9 or the cDNA sequence thereof; (d) a variant comprising the polypeptide of SEQ ID NO: 2, SEQ ID NO: 4, SEQ ID NO: 6, SEQ ID NO: 8, or SEQ ID NO: 10 comprising a substitution, deletion, and/or insertion at one or more (e.g., several) positions; and (e) a fragment of the polypeptide of (a), (b), (c), or (d) that has cellobiohydrolase activity.

[2] The polypeptide of paragraph 1, having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 2 or SEQ ID NO: 4; at least 90%, at least 91%, at least 92%, at least 93%, at least 94%, at least 95%, at least 96%, at least 97%, at least 98%, at least 99%, or 100% sequence identity to the polypeptide of SEQ ID NO: 6; at least 91%, at least 92%, at least 93%, at least 94%, at least 95%, at least 96%, at least 97%, at least 98%, at least 99%, or 100% sequence identity to the polypeptide of SEQ ID NO: 8; or at least 99% or 100% sequence identity to the polypeptide of SEQ ID NO: 10.

[3] The polypeptide of paragraph 1, which is encoded by a polynucleotide that hybridizes under very high stringency conditions with (i) the polypeptide coding sequence of SEQ ID NO: 1, SEQ ID NO: 3, SEQ ID NO: 5, SEQ ID NO: 7, or SEQ ID NO: 9, (ii) the cDNA sequence thereof, or (iii) the full-length complement of (i) or (ii).

[4] The polypeptide of paragraph 1, which is encoded by a polynucleotide having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 1 or SEQ ID NO: 3, or the cDNA sequences thereof; at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 5 or the cDNA sequence thereof; at least 91%, at least 92%, at least 93%, at least 94%, at least 95%, at least 96%, at least 97%, at least 98%, at least 99%, or 100% sequence identity to the polypeptide coding sequence of SEQ ID NO: 7 or the cDNA sequences thereof; or at least 99% or 100% sequence identity to the polypeptide coding sequence of SEQ ID NO: 9 or the cDNA sequence thereof.

[5] The polypeptide of any of paragraphs 1-4, comprising or consisting of SEQ ID NO: 2, SEQ ID NO: 4, SEQ ID NO: 6, SEQ ID NO: 8, or SEQ ID NO: 10 or the polypeptide of SEQ ID NO: 2, SEQ ID NO: 4, SEQ ID NO: 6, SEQ ID NO: 8, or SEQ ID NO: 10.

[6] The polypeptide of paragraph 1, which is a variant comprising the polypeptide of SEQ ID NO: 2, SEQ ID NO: 4, SEQ ID NO: 6, SEQ ID NO: 8, or SEQ ID NO: 10 comprising a substitution, deletion, and/or insertion at one or more positions.

[7] The polypeptide of paragraph 1, which is a fragment of SEQ ID NO: 2, SEQ ID NO: 4, SEQ ID NO: 6, SEQ ID NO: 8, or SEQ ID NO: 10, wherein the fragment has cellobiohydrolase activity.

[8] An isolated polypeptide having cellobiohydrolase activity, selected from the group consisting of: (a) a polypeptide having cellobiohydrolase activity having at least 70% sequence identity to the polypeptide of SEQ ID NO: 12; at least 80% sequence identity to the polypeptide of SEQ ID NO: 14 or SEQ ID NO: 16; at least 91% sequence identity to the polypeptide of SEQ ID NO: 18; at least 96% sequence identity to the polypeptide of SEQ ID NO: 20; or at least 98% sequence identity to the polypeptide of SEQ ID NO: 22 or SEQ ID NO: 24; (b) a polypeptide having cellobiohydrolase activity encoded by a polynucleotide that hybridizes under at least very high stringency conditions with (i) the polypeptide coding sequence of SEQ ID NO: 11, SEQ ID NO: 13, SEQ ID NO: 15, SEQ ID NO: 17, SEQ ID NO: 19, SEQ ID NO: 21, or SEQ ID NO: 23, (ii) the cDNA sequence thereof, or (iii) the full-length complement of (i) or (ii); (c) a polypeptide having cellobiohydrolase activity encoded by a polynucleotide having at least 70% sequence identity to the polypeptide coding sequence SEQ ID NO: 11 or the cDNA sequence thereof; at least 80% sequence identity to the polypeptide coding sequence of SEQ ID NO: 13 or SEQ ID NO: 15, or the cDNA sequences thereof; at least 91% sequence identity to the polypeptide coding sequence of SEQ ID NO: 17 or the cDNA sequence thereof; at least 96% sequence identity to the polypeptide coding sequence of SEQ ID NO: 19 or the cDNA sequence thereof; or at least 98% sequence identity to the polypeptide coding sequence of SEQ ID NO: 21 or SEQ ID NO: 23, or the cDNA sequences thereof; (d) a cellobiohydrolase variant comprising the polypeptide of SEQ ID NO: 12, SEQ ID NO: 14, SEQ ID NO: 16, SEQ ID NO: 18, SEQ ID NO: 20, SEQ ID NO: 22, or SEQ ID NO: 24 comprising a substitution, deletion, and/or insertion at one or more positions; and (e) a fragment of the polypeptide of (a), (b), (c), or (d) that has cellobiohydrolase activity.

[9] The polypeptide of paragraph 8, having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 12; at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 14 or SEQ ID NO: 16; at least 91%, at least 92%, at least 93%, at least 94%, at least 95%, at least 96%, at least 97%, at least 98%, at least 99%, or 100% sequence identity to the polypeptide of SEQ ID NO: 18; at least 96%, at least 97%, at least 98%, at least 99%, or 100% sequence identity to the polypeptide of SEQ ID NO: 20; or at least 98%, at least 99% or 100% sequence identity to the polypeptide of SEQ ID NO: 22 or SEQ ID NO: 24.

[10] The polypeptide of paragraph 8, which is encoded by a polynucleotide that hybridizes under very high stringency conditions with (i) the polypeptide coding sequence of SEQ ID NO: 11, SEQ ID NO: 13, SEQ ID NO: 15, SEQ ID NO: 17, SEQ ID NO: 19, SEQ ID NO: 21, or SEQ ID NO: 23, (ii) the cDNA sequence thereof, or (iii) the full-length complement of (i) or (ii).

[11] The polypeptide of paragraph 8, which is encoded by a polynucleotide having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence SEQ ID NO: 11 or the cDNA sequence thereof; at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 13 or SEQ ID NO: 15, or the cDNA sequences thereof; at least 91%, at least 92%, at least 93%, at least 94%, at least 95%, at least 96%, at least 97%, at least 98%, at least 99%, or 100% sequence identity to the polypeptide coding sequence of SEQ ID NO: 17 or the cDNA sequence thereof; at least 96%, at least 97%, at least 98%, at least 99%, or 100% sequence identity to the polypeptide coding sequence of SEQ ID NO: 19 or the cDNA sequence thereof; or at least 98%, at least 99% or 100% sequence identity to the polypeptide coding sequence of SEQ ID NO: 21 or SEQ ID NO: 23, or the cDNA sequences thereof.

[12] The polypeptide of any of paragraphs 8-11, comprising or consisting of SEQ ID NO: 12, SEQ ID NO: 14, SEQ ID NO: 16, SEQ ID NO: 18, SEQ ID NO: 20, SEQ ID NO: 22, or SEQ ID NO: 24 or the polypeptide of SEQ ID NO: 12, SEQ ID NO: 14, SEQ ID NO: 16, SEQ ID NO: 18, SEQ ID NO: 20, SEQ ID NO: 22, or SEQ ID NO: 24.

[13] The polypeptide of paragraph 8, which is a variant comprising the polypeptide of SEQ ID NO: 12, SEQ ID NO: 14, SEQ ID NO: 16, SEQ ID NO: 18, SEQ ID NO: 20, SEQ ID NO: 22, or SEQ ID NO: 24 comprising a substitution, deletion, and/or insertion at one or more positions.

[14] The polypeptide of paragraph 8, which is a fragment of SEQ ID NO: 12, SEQ ID NO: 14, SEQ ID NO: 16, SEQ ID NO: 18, SEQ ID NO: 20, SEQ ID NO: 22, or SEQ ID NO: 242, wherein the fragment has cellobiohydrolase activity.

[15] An isolated polypeptide having endoglucanase activity, selected from the group consisting of: (a) a polypeptide having at least 60% sequence identity to the polypeptide of SEQ ID NO: 26; at least 65% sequence identity to the polypeptide of SEQ ID NO: 28; at least 70% sequence identity to the polypeptide of SEQ ID NO: 30 or SEQ ID NO: 32; at least 80% sequence identity to the polypeptide of SEQ ID NO: 34, SEQ ID NO: 36, or SEQ ID NO: 38; at least 85% sequence identity to the polypeptide of SEQ ID NO: 40 or SEQ ID NO: 42; at least 97% sequence identity to the polypeptide of SEQ ID NO: 44; or at least 98% sequence identity to the polypeptide of SEQ ID NO: 46; (b) a polypeptide encoded by a polynucleotide that hybridizes under at least high stringency conditions with (i) the polypeptide coding sequence of SEQ ID NO: 25 or SEQ ID NO: 27, (ii) the cDNA sequence thereof, or (iii) the full-length complement of (i) or (ii); or under at least very high stringency conditions with (i) the polypeptide coding sequence of SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, or SEQ ID NO: 45, (ii) the cDNA sequence thereof, or (iii) the full-length complement of (i) or (ii); (c) a polypeptide encoded by a polynucleotide having at least 60% sequence identity to the polypeptide coding sequence of SEQ ID NO: 25 or the cDNA sequence thereof; at least 65% sequence identity to the polypeptide coding sequence of SEQ ID NO: 27 or the cDNA sequence thereof; at least 70% sequence identity to the polypeptide coding sequence of SEQ ID NO: 29 or SEQ ID NO: 31, or the cDNA sequences thereof; at least 80% sequence identity to the polypeptide coding sequence of SEQ ID NO: 33, SEQ ID NO: 35, or SEQ ID NO: 37, the cDNA sequences thereof; at least 85% sequence identity to the polypeptide coding sequence of SEQ ID NO: 39 or SEQ ID NO: 41, or the cDNA sequences thereof; at least 97% sequence identity to the polypeptide coding sequence of SEQ ID NO: 43 or the cDNA sequence thereof; or at least 98% sequence identity to the polypeptide coding sequence of SEQ ID NO: 45 or the cDNA sequence thereof; (d) a variant comprising the polypeptide of SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, or SEQ ID NO: 46 comprising a substitution, deletion, and/or insertion at one or more positions; and (e) a fragment of the polypeptide of (a), (b), (c), or (d) that has endoglucanase activity.

[16] The polypeptide of paragraph 15, having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 26; at least 65%, e.g., at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 28; at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 30 or SEQ ID NO: 32; at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 34, SEQ ID NO: 36, or SEQ ID NO: 38; at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 40 or SEQ ID NO: 42; at least 97%, at least 98%, at least 99%, or 100% sequence identity to the polypeptide of SEQ ID NO: 44; or at least 98%, at least 99% or 100% sequence identity to the polypeptide of SEQ ID NO: 46.

[17] The polypeptide of paragraph 15, which is encoded by a polynucleotide that hybridizes under high or very high stringency conditions with (i) the polypeptide coding sequence of SEQ ID NO: 25 or SEQ ID NO: 27, (ii) the cDNA sequence thereof, or (iii) the full-length complement of (i) or (ii); or under very high stringency conditions with (i) the polypeptide coding sequence of SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, or SEQ ID NO: 45, (ii) the cDNA sequence thereof, or (iii) the full-length complement of (i) or (ii).

[18] The polypeptide of paragraph 15, which is encoded by a polynucleotide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 25 or the cDNA sequence thereof; at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 27 or the cDNA sequence thereof; at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 29 or SEQ ID NO: 31, or the cDNA sequences thereof; at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 33, SEQ ID NO: 35, or SEQ ID NO: 37, or the cDNA sequences thereof; at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 39 or SEQ ID NO: 41, or the cDNA sequences thereof; at least 97%, at least 98%, at least 99%, or 100% sequence identity to the polypeptide coding sequence of SEQ ID NO: 43 or the cDNA sequence thereof; or at least 98%, at least 99% or 100% sequence identity to the polypeptide coding sequence of SEQ ID NO: 45 or the cDNA sequence thereof.

[19] The polypeptide of any of paragraphs 15-18, comprising or consisting of SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, or SEQ ID NO: 46 or the polypeptide of SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, or SEQ ID NO: 46.

[20] The polypeptide of paragraph 15, which is a variant comprising the polypeptide of SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, or SEQ ID NO: 462 comprising a substitution, deletion, and/or insertion at one or more positions.

[21] The polypeptide of paragraph 15, which is a fragment of SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, or SEQ ID NO: 46, wherein the fragment has endoglucanase activity.

[22] An isolated polypeptide having cellulolytic enhancing activity, selected from the group consisting of: (a) a polypeptide having at least 70% sequence identity to the polypeptide of SEQ ID NO: 48; at least 75% sequence identity to the polypeptide of SEQ ID NO: 50, SEQ ID NO: 52, SEQ ID NO: 54, or SEQ ID NO: 79; at least 80% sequence identity to the polypeptide of SEQ ID NO: 56, SEQ ID NO: 58, SEQ ID NO: 60, SEQ ID NO: 62, or SEQ ID NO: 64; at least 85% sequence identity to the polypeptide of SEQ ID NO: 66; or at least 90% sequence identity to the polypeptide of SEQ ID NO: 68 or SEQ ID NO: 70; (b) a polypeptide encoded by a polynucleotide that hybridizes under at least very high stringency conditions with (i) the polypeptide coding sequence of SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, or SEQ ID NO: 71, (ii) the cDNA sequence thereof, or (iii) the full-length complement of (i) or (ii); (c) a polypeptide encoded by a polynucleotide having at least 70% sequence identity to the polypeptide coding sequence of SEQ ID NO: 47 or the cDNA sequence thereof; at least 75% sequence identity to the polypeptide coding sequence of SEQ ID NO: 49, SEQ ID NO: 51, or SEQ ID NO: 53, or the cDNA sequences thereof; at least 80% sequence identity to the polypeptide coding sequence of SEQ ID NO: 55, SEQ ID NO: 57, SEQ ID NO: 59, SEQ ID NO: 61, or SEQ ID NO: 63, or the cDNA sequences thereof; at least 85% sequence identity to the polypeptide coding sequence of SEQ ID NO: 65 or the cDNA sequence thereof; or at least 90% sequence identity to the polypeptide coding sequence of SEQ ID NO: 67, SEQ ID NO: 69, or SEQ ID NO: 71, or the cDNA sequences thereof; (d) a variant comprising the polypeptide of SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 69, SEQ ID NO: 70, SEQ ID NO: 72, or SEQ ID NO: 79 comprising a substitution, deletion, and/or insertion at one or more positions; and (e) a fragment of the polypeptide of (a), (b), (c), or (d) that has cellulolytic enhancing activity.

[23] The polypeptide of paragraph 22, having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 48; at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 50, SEQ ID NO: 52, SEQ ID NO: 54, or SEQ ID NO: 79; at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 56, SEQ ID NO: 58, SEQ ID NO: 60, SEQ ID NO: 62, or SEQ ID NO: 64; at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 66; or at least 90%, at least 91%, at least 92%, at least 93%, at least 94%, at least 95%, at least 96%, at least 97%, at least 98%, at least 99%, or 100% sequence identity to the polypeptide of SEQ ID NO: 68, SEQ ID NO: 70, or SEQ ID NO: 72.

[24] The polypeptide of paragraph 22, which is encoded by a polynucleotide that hybridizes under very high stringency conditions with (i) the polypeptide coding sequence of SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, or SEQ ID NO: 71, (ii) the cDNA sequence thereof, or (iii) the full-length complement of (i) or (ii).

[25] The polypeptide of paragraph 22, which is encoded by a polynucleotide having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 47 or the cDNA sequence thereof; at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 49, SEQ ID NO: 51, or SEQ ID NO: 53, or the cDNA sequences thereof; at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 55, SEQ ID NO: 57, SEQ ID NO: 59, SEQ ID NO: 61, or SEQ ID NO: 63, or the cDNA sequences thereof; at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 65 or the cDNA sequence thereof; or at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 67, SEQ ID NO: 69, or SEQ ID NO: 71, or the cDNA sequences thereof.

[26] The polypeptide of any of paragraphs 22-25, comprising or consisting of SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 69, SEQ ID NO: 70, or SEQ ID NO: 72 or the polypeptide of SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 69, SEQ ID NO: 70, SEQ ID NO: 72, or SEQ ID NO: 79.

[27] The polypeptide of paragraph 22, which is a variant comprising the polypeptide of SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 69, SEQ ID NO: 70, SEQ ID NO: 72, or SEQ ID NO: 79 comprising a substitution, deletion, and/or insertion at one or more positions.

[28] The polypeptide of paragraph 22, which is a fragment of SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 69, SEQ ID NO: 70, SEQ ID NO: 72, or SEQ ID NO: 79, wherein the fragment has cellulolytic enhancing activity.

[29] An isolated polypeptide having xylanase activity, selected from the group consisting of: (a) a polypeptide having at least 70% sequence identity to the polypeptide of SEQ ID NO: 74, at least 94% sequence identity to the polypeptide of SEQ ID NO: 78, or at least 98% sequence identity to the polypeptide of SEQ ID NO: 76; (b) a polypeptide encoded by a polynucleotide that hybridizes under at least very high stringency conditions with (i) the polypeptide coding sequence of SEQ ID NO: 73, SEQ ID NO: 75, or SEQ ID NO: 77, (ii) the cDNA sequence thereof, or (iii) the full-length complement of (i) or (ii); (c) a polypeptide encoded by a polynucleotide having at least 70% sequence identity to the polypeptide coding sequence of SEQ ID NO: 73 or the cDNA sequence thereof, at least 94% sequence identity to the polypeptide coding sequence of SEQ ID NO: 77 or the cDNA sequence thereof, or at least 98% sequence identity to the polypeptide coding sequence of SEQ ID NO: 75 or the cDNA sequence thereof; (d) a variant comprising the polypeptide of SEQ ID NO: 74, SEQ ID NO: 76, or SEQ ID NO: 78 comprising a substitution, deletion, and/or insertion at one or more positions; and (e) a fragment of the polypeptide of (a), (b), (c), or (d) that has xylanase activity.

[30] The polypeptide of paragraph 29, having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 74, at least 94%, at least 95%, at least 96%, at least 97%, at least 98%, at least 99%, or 100% sequence identity to the polypeptide of SEQ ID NO: 78, or at least 98%, at least 99%, or 100% sequence identity to the polypeptide of SEQ ID NO: 76.

[30] The polypeptide of paragraph 29, which is encoded by a polynucleotide that hybridizes under very high stringency conditions with (i) the polypeptide coding sequence of SEQ ID NO: 73, SEQ ID NO: 75, or SEQ ID NO: 77, (ii) the cDNA sequence thereof, or (iii) the full-length complement of (i) or (ii).

[32] The polypeptide of paragraph 29, which is encoded by a polynucleotide having at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide coding sequence of SEQ ID NO: 73 or the cDNA sequence thereof, at least 94%, at least 95%, at least 96%, at least 97%, at least 98%, at least 99%, or 100% sequence identity to the polypeptide coding sequence of SEQ ID NO: 77 or the cDNA sequence thereof, or at least 98%, at least 99%, or 100% sequence identity to the polypeptide coding sequence of SEQ ID NO: 75 or the cDNA sequence thereof.

[33] The polypeptide of any of paragraphs 29-32, comprising or consisting of SEQ ID NO: 74, SEQ ID NO: 76, or SEQ ID NO: 78 or the polypeptide of SEQ ID NO: 74, SEQ ID NO: 76, or SEQ ID NO: 78.

[34] The polypeptide of paragraph 29, which is a variant comprising the polypeptide of SEQ ID NO: 74, SEQ ID NO: 76, or SEQ ID NO: 78 comprising a substitution, deletion, and/or insertion at one or more positions.

[35] The polypeptide of paragraph 29, which is a fragment of SEQ ID NO: 74, SEQ ID NO: 76, or SEQ ID NO: 78, wherein the fragment has xylanase activity.

[36] A composition comprising the polypeptide of any of paragraphs 1-35.

[37] An isolated polynucleotide encoding the polypeptide of any of paragraphs 1-35.

[38] A nucleic acid construct or expression vector comprising the polynucleotide of paragraph 37 operably linked to one or more control sequences that direct the production of the polypeptide in an expression host.

[39] A recombinant host cell comprising the polynucleotide of paragraph 37 operably linked to one or more control sequences that direct the production of the polypeptide.

[40] A method of producing the polypeptide of any of paragraphs 1-35, comprising: (a) cultivating a cell, which in its wild-type form produces the polypeptide, under conditions conducive for production of the polypeptide; and (b) recovering the polypeptide.

[41] A method of producing a polypeptide having enzyme activity, comprising: (a) cultivating the host cell of paragraph 39 under conditions conducive for production of the polypeptide; and (b) recovering the polypeptide.

[42] A transgenic plant, plant part or plant cell transformed with a polynucleotide encoding the polypeptide of any of paragraphs 1-35.

[43] A method of producing a polypeptide having xylanase activity, comprising: (a) cultivating the transgenic plant or plant cell of paragraph 42 under conditions conducive for production of the polypeptide; and (b) recovering the polypeptide.

[44] A method of producing a mutant of a parent cell, comprising inactivating a polynucleotide encoding the polypeptide of any of paragraphs 1-35, which results in the mutant producing less of the polypeptide than the parent cell.

[45] A mutant cell produced by the method of paragraph 44.

[46] The mutant cell of paragraph 45, further comprising a gene encoding a native or heterologous protein.

[47] A method of producing a protein, comprising: (a) cultivating the mutant cell of paragraph 45 or 46 under conditions conducive for production of the protein; and (b) recovering the protein.

[48] A double-stranded inhibitory RNA (dsRNA) molecule comprising a subsequence of the polynucleotide of paragraph 37, wherein optionally the dsRNA is an siRNA or an miRNA molecule.

[49] The double-stranded inhibitory RNA (dsRNA) molecule of paragraph 48, which is about 15, 16, 17, 18, 19, 20, 21, 22, 23, 24, 25 or more duplex nucleotides in length.

[50] A method of inhibiting the expression of a polypeptide having xylanase activity in a cell, comprising administering to the cell or expressing in the cell the double-stranded inhibitory RNA (dsRNA) molecule of paragraph 48 or 49.

[51] A cell produced by the method of paragraph 50.

[52] The cell of paragraph 51, further comprising a gene encoding a native or heterologous protein.

[53] A method of producing a protein, comprising: (a) cultivating the cell of paragraph 51 or 52 under conditions conducive for production of the protein; and (b) recovering the protein.

[54] A process for degrading or converting a cellulosic or xylan-containing material, comprising: treating the cellulosic or xylan-containing material with an enzyme composition in the presence of the polypeptide having xylanase activity of any of paragraphs 1-35.

[55] The process of paragraph 54, wherein the cellulosic or xylan-containing material is pretreated.

[56] The process of paragraph 54 or 55, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[57] The process of paragraph 56, wherein the cellulase is one or more enzymes selected from the group consisting of an endoglucanase, a cellobiohydrolase, and a beta-glucosidase.

[58] The process of paragraph 56, wherein the hemicellulase is one or more enzymes selected from the group consisting of a xylanase, an acetylxylan esterase, a feruloyl esterase, an arabinofuranosidase, a xylosidase, and a glucuronidase.

[59] The process of any of paragraphs 54-58, further comprising recovering the degraded cellulosic or xylan-containing material.

[60] The process of paragraph 59, wherein the degraded cellulosic or xylan-containing material is a sugar.

[61] The process of paragraph 60, wherein the sugar is selected from the group consisting of glucose, xylose, mannose, galactose, and arabinose.

[62] A process for producing a fermentation product, comprising: (a) saccharifying a cellulosic or xylan-containing material with an enzyme composition in the presence of the polypeptide having xylanase activity of any of paragraphs 1-35; (b) fermenting the saccharified cellulosic or xylan-containing material with one or more fermenting microorganisms to produce the fermentation product; and (c) recovering the fermentation product from the fermentation.

[63] The process of paragraph 62, wherein the cellulosic or xylan-containing material is pretreated.

[64] The process of paragraph 62 or 63, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[65] The process of paragraph 64, wherein the cellulase is one or more enzymes selected from the group consisting of an endoglucanase, a cellobiohydrolase, and a beta-glucosidase.

[66] The process of paragraph 64, wherein the hemicellulase is one or more enzymes selected from the group consisting of a xylanase, an acetylxylan esterase, a feruloyl esterase, an arabinofuranosidase, a xylosidase, and a glucuronidase.

[67] The process of any of paragraphs 62-66, wherein steps (a) and (b) are performed simultaneously in a simultaneous saccharification and fermentation.

[68] The process of any of paragraphs 62-67, wherein the fermentation product is an alcohol, an alkane, a cycloalkane, an alkene, an amino acid, a gas, isoprene, a ketone, an organic acid, or polyketide.

[69] A process of fermenting a cellulosic or xylan-containing material, comprising: fermenting the cellulosic or xylan-containing material with one or more fermenting microorganisms, wherein the cellulosic or xylan-containing material is saccharified with an enzyme composition in the presence of the polypeptide having xylanase activity of any of paragraphs 1-35.

[70] The process of paragraph 69, wherein the fermenting of the cellulosic or xylan-containing material produces a fermentation product.

[71] The process of paragraph 70, further comprising recovering the fermentation product from the fermentation.

[72] The process of paragraph 71, wherein the fermentation product is an alcohol, an alkane, a cycloalkane, an alkene, an amino acid, a gas, isoprene, a ketone, an organic acid, or polyketide.

[73] The process of any of paragraphs 69-72, wherein the cellulosic or xylan-containing material is pretreated before saccharification.

[74] The process of any of paragraphs 69-73, wherein the enzyme composition comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

[75] The process of paragraph 74, wherein the cellulase is one or more enzymes selected from the group consisting of an endoglucanase, a cellobiohydrolase, and a beta-glucosidase.

[76] The process of paragraph 74, wherein the hemicellulase is one or more enzymes selected from the group consisting of a xylanase, an acetylxylan esterase, a feruloyl esterase, an arabinofuranosidase, a xylosidase, and a glucuronidase.

[77] A whole broth formulation or cell culture composition comprising the polypeptide of any of paragraphs 1-35.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A nucleic acid construct comprising a polynucleotide encoding a polypeptide having cellobiohydrolase activity, wherein the polynucleotide is operably linked to one or more heterologous control sequences that direct the production of the polypeptide having cellobiohydrolase activity in a host cell, and wherein the polypeptide having cellobiohydrolase activity is selected from the group consisting of:
   (a) a polypeptide having at least 90% sequence identity to the polypeptide of SEQ ID NO: 4;
   (b) a polypeptide encoded by a polynucleotide that hybridizes under very high stringency conditions with (i) the polypeptide coding sequence of SEQ ID NO: 3, (ii) the cDNA sequence thereof, or (iii) the full-length complement of (i) or (ii), wherein very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.;
   (c) a polypeptide encoded by a polynucleotide having at least 90% sequence identity to the polypeptide coding sequence of SEQ ID NO: 3, or the cDNA sequence thereof;
   (d) a fragment of the polypeptide of (a), (b), or (c) that has cellobiohydrolase activity;
   (e) a polypeptide comprising SEQ ID NO: 4; and
   (f) a polypeptide encoded by the polynucleotide of SEQ ID NO: 3 or the cDNA sequence thereof.

2. A recombinant host cell comprising the nucleic acid construct of claim 1.

3. A method of producing a polypeptide having enzyme activity, comprising:
   (a) cultivating the host cell of claim 2 under conditions conducive for production of the polypeptide; and
   (b) recovering the polypeptide.

4. A process for degrading or converting a cellulosic or xylan-containing material, comprising:
   (a) treating the cellulosic or xylan-containing material with an enzyme composition comprising a polypeptide having cellobiohydrolase activity at a temperature of about 50° C. to about 80° C., wherein the polypeptide having cellobiohydrolase activity is selected from the group consisting of:
   (1) a polypeptide having at least 90% sequence identity to the polypeptide of SEQ ID NO: 4;
   (2) a polypeptide encoded by a polynucleotide that hybridizes under very high stringency conditions with (i) the polypeptide coding sequence of SEQ ID NO: 3, (ii) the cDNA sequence thereof, or (iii) the full-length complement of (i) or (ii), wherein very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.;
   (3) a polypeptide encoded by a polynucleotide having at least 90% sequence identity to the polypeptide coding sequence of SEQ ID NO: 3, or the cDNA sequence thereof;
   (4) a fragment of the polypeptide of (1), (2), or (3) that has cellobiohydrolase activity;
   (5) a polypeptide comprising SEQ ID NO: 4; and
   (6) a polypeptide encoded by the polynucleotide of SEQ ID NO: 3 or the cDNA sequence thereof.

5. The process of claim 4, further comprising recovering the degraded or converted cellulosic or xylan-containing material.

6. A process for producing a fermentation product, comprising:
   (a) saccharifying a cellulosic or xylan-containing material with an enzyme composition comprising a polypeptide having cellobiohydrolase activity at a temperature of about 50° C. to about 80° C., wherein the polypeptide having cellobiohydrolase activity is selected from the group consisting of:
   (1) a polypeptide having at least 90% sequence identity to the polypeptide of SEQ ID NO: 4;
   (2) a polypeptide encoded by a polynucleotide that hybridizes under very high stringency conditions with (i) the polypeptide coding sequence of SEQ ID NO: 3, (ii) the cDNA sequence thereof, or (iii) the full-length complement of (i) or (ii), wherein very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.;
   (3) a polypeptide encoded by a polynucleotide having at least 90% sequence identity to the polypeptide coding sequence of SEQ ID NO: 3, or the cDNA sequence thereof;
   (4) a fragment of the polypeptide of (1), (2), or (3) that has cellobiohydrolase activity
   (5) a polypeptide comprising SEQ ID NO: 4; and
   (6) a polypeptide encoded by the polynucleotide of SEQ ID NO: 3 or the cDNA sequence thereof;
   (b) fermenting the saccharified cellulosic or xylan-containing material with one or more fermenting microorganisms to produce the fermentation product; and
   (c) recovering the fermentation product from the fermentation.

7. A process of fermenting a cellulosic or xylan-containing material, comprising: fermenting the cellulosic or xylan-containing material with one or more fermenting microorganisms, wherein the cellulosic or xylan-containing material is saccharified with an enzyme composition comprising a polypeptide having cellobiohydrolase activity at a temperature of about 50° C. to about 80° C., wherein the polypeptide having cellobiohydrolase activity is selected from the group consisting of:
   (1) a polypeptide having at least 90% sequence identity to the polypeptide of SEQ ID NO: 4;
   (2) a polypeptide encoded by a polynucleotide that hybridizes under very high stringency conditions with (i) the polypeptide coding sequence of SEQ ID NO: 3, (ii) the cDNA sequence thereof, or (iii) the full-length complement of (i) or (ii), wherein very high stringency conditions are defined as prehybridization and hybridization at 42° C. in 5×SSPE, 0.3% SDS, 200 micrograms/ml sheared and denatured salmon sperm DNA, and 50% formamide, and washing three times each for 15 minutes using 2×SSC, 0.2% SDS at 70° C.;
   (3) a polypeptide encoded by a polynucleotide having at least 90% sequence identity to the polypeptide coding sequence of SEQ ID NO: 3, or the cDNA sequence thereof;
   (4) a fragment of the polypeptide of (1), (2), or (3) that has cellobiohydrolase activity;
   (5) a polypeptide comprising SEQ ID NO: 4; and
   (6) a polypeptide encoded by the polynucleotide of SEQ ID NO: 3 or the cDNA sequence thereof.

8. The nucleic acid construct of claim 1, wherein the polypeptide has at least 95% sequence identity to the polypeptide of SEQ ID NO: 4.

9. The process of claim 4, wherein the cellulosic or xylan-containing material is pretreated.

10. The process of claim 4, wherein the degraded or converted cellulosic or xylan-containing material is a sugar.

11. The process of claim 10, wherein the sugar is selected from the group consisting of glucose, xylose, mannose, galactose, and arabinose.

12. The process of claim 4, wherein the polypeptide has at least 95% sequence identity to the polypeptide of SEQ ID NO: 4.

13. The process of claim 4, wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

14. The process of claim 6, wherein the cellulosic or xylan-containing material is pretreated.

15. The process of claim 6, wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollenin.

16. The process of claim 6, wherein steps (a) and (b) are performed simultaneously in a simultaneous saccharification and fermentation.

17. The process of claim 6, wherein the polypeptide has at least 95% sequence identity to the polypeptide of SEQ ID NO: 4.

18. The process of claim 7, wherein the fermenting of the cellulosic or xylan-containing material produces a fermentation product.

19. The process of claim 18, further comprising recovering the fermentation product from the fermentation.

20. The process of claim 7, wherein the cellulosic or xylan-containing material is pretreated before saccharification.

21. The process of claim 7, wherein the enzyme composition further comprises one or more enzymes selected from the group consisting of a cellulase, a polypeptide having cellulolytic enhancing activity, a hemicellulase, an esterase, an expansin, a laccase, a ligninolytic enzyme, a pectinase, a peroxidase, a protease, and a swollen in.

22. The process of claim 7, wherein the polypeptide has at least 95% sequence identity to the polypeptide of SEQ ID NO: 4.

23. The nucleic acid construct of claim 1, wherein the polypeptide has at least 91% sequence identity to the polypeptide of SEQ ID NO: 4.

24. The nucleic acid construct of claim 1, wherein the polypeptide has at least 92% sequence identity to the polypeptide of SEQ ID NO: 4.

25. The nucleic acid construct of claim 1, wherein the polypeptide has at least 93% sequence identity to the polypeptide of SEQ ID NO: 4.

26. The nucleic acid construct of claim 1, wherein the polypeptide has at least 94% sequence identity to the polypeptide of SEQ ID NO: 4.

27. The nucleic acid construct of claim 1, wherein the polypeptide has at least 96% sequence identity to the polypeptide of SEQ ID NO: 4.

28. The nucleic acid construct of claim 1, wherein the polypeptide has at least 97% sequence identity to the polypeptide of SEQ ID NO: 4.

29. The nucleic acid construct of claim 1, wherein the polypeptide has at least 98% sequence identity to the polypeptide of SEQ ID NO: 4.

30. The nucleic acid construct of claim 1, wherein the polypeptide has at least 99% sequence identity to the polypeptide of SEQ ID NO: 4.

31. The nucleic acid construct of claim 1, wherein the polypeptide comprises SEQ ID NO: 4.

32. The process of claim 4, wherein the polypeptide has at least 91% sequence identity to the polypeptide of SEQ ID NO: 4.

33. The process of claim 4, wherein the polypeptide has at least 92% sequence identity to the polypeptide of SEQ ID NO: 4.

34. The process of claim 4, wherein the polypeptide has at least 93% sequence identity to the polypeptide of SEQ ID NO: 4.

35. The process of claim 4, wherein the polypeptide has at least 94% sequence identity to the polypeptide of SEQ ID NO: 4.

36. The process of claim 4, wherein the polypeptide has at least 96% sequence identity to the polypeptide of SEQ ID NO: 4.

37. The process of claim 3, wherein the polypeptide has at least 97% sequence identity to the polypeptide of SEQ ID NO: 4.

38. The process of claim 3, wherein the polypeptide has at least 98% sequence identity to the polypeptide of SEQ ID NO: 4.

39. The process of claim 4, wherein the polypeptide has at least 99% sequence identity to the polypeptide of SEQ ID NO: 4.

40. The process of claim 4, wherein the polypeptide comprises SEQ ID NO: 4.

41. The process of claim 6, wherein the polypeptide has at least 91% sequence identity to the polypeptide of SEQ ID NO: 4.

42. The process of claim 6, wherein the polypeptide has at least 92% sequence identity to the polypeptide of SEQ ID NO: 4.

43. The process of claim 6, wherein the polypeptide has at least 93% sequence identity to the polypeptide of SEQ ID NO: 4.

44. The process of claim 6, wherein the polypeptide has at least 94% sequence identity to the polypeptide of SEQ ID NO: 4.

45. The process of claim 6, wherein the polypeptide has at least 96% sequence identity to the polypeptide of SEQ ID NO: 4.

46. The process of claim 6, wherein the polypeptide has at least 97% sequence identity to the polypeptide of SEQ ID NO: 4.

47. The process of claim 6, wherein the polypeptide has at least 98% sequence identity to the polypeptide of SEQ ID NO: 4.

48. The process of claim 6, wherein the polypeptide has at least 99% sequence identity to the polypeptide of SEQ ID NO: 4.

49. The process of claim 6, wherein the polypeptide comprises SEQ ID NO: 4.

50. The process of claim 7, wherein the polypeptide has at least 91% sequence identity to the polypeptide of SEQ ID NO: 4.

51. The process of claim 7, wherein the polypeptide has at least 92% sequence identity to the polypeptide of SEQ ID NO: 4.

52. The process of claim 7, wherein the polypeptide has at least 93% sequence identity to the polypeptide of SEQ ID NO: 4.

53. The process of claim 7, wherein the polypeptide has at least 94% sequence identity to the polypeptide of SEQ ID NO: 4.

54. The process of claim 7, wherein the polypeptide has at least 96% sequence identity to the polypeptide of SEQ ID NO: 4.

55. The process of claim 7, wherein the polypeptide has at least 97% sequence identity to the polypeptide of SEQ ID NO: 4.

56. The process of claim 7, wherein the polypeptide has at least 98% sequence identity to the polypeptide of SEQ ID NO: 4.

57. The process of claim 7, wherein the polypeptide has at least 99% sequence identity to the polypeptide of SEQ ID NO: 4.

58. The process of claim 7, wherein the polypeptide comprises SEQ ID NO: 4.

* * * * *

SEQUENCE LISTING

```
<160> NUMBER OF SEQ ID NOS: 103

<210> SEQ ID NO 1
<211> LENGTH: 816
<212> TYPE: DNA
<213> ORGANISM: Chaetomium senegalense

<400> SEQUENCE: 1
gactgtgctg ctgctgcttc caacggcgag tggtcgattg ccaacggcgg cgtagccaac      60
tacaaggcct acattgacag gatccgccac cacctcgtcg cgtattcgga ccttcgtgtc     120
atcctggtca ttgagcccga ctctctcgcc aacatggtca ccaacatgaa cgttccgaag     180
tgccagggcg cagccagcac ctacagggag ctgaccattt acgccatgca gcggctcaac     240
ctgccgaacg ttgccatgta tctcgatgcc ggccacgcgg gctggctcgg ctggcctgcc     300
aacatccagc ccgctgccga cctgttcgcc aacctctaca aggacgccgg taggcctgcc     360
gctgtccgcg gactggtgac taacgtgtcc aattacaacg gctggaacct gacctcgcct     420
cccccctaca cgtcgcccaa ccccaactac gatgagcgcc gttacgtcga ggcctttgcc     480
cctctcctgc aagccaatgg atggaacgcc cgcttcatca ccgacaccgg ccggagcggc     540
aagcagccga ccggacagat cgagtggggc aactggtgca actcccgcgg aactggcttt     600
ggcatgcggc caacgagcaa cacgaaccac gaactgatgg atgcattcgt ttgggtgaag     660
```

```
cccggcggcg agagcgacgg cacatccgac acctcggccg ctcgctacga ccgcaactgc    720
gattcgaagg ccgccatgaa gcccgcccgt gaggccggcc agtggttccg ggcctacttc    780
gagatgctgt tgacgaatgc aaccctcct tttttaa                              816
```

<210> SEQ ID NO 2
<211> LENGTH: 271
<212> TYPE: PRT
<213> ORGANISM: Chaetomium senegalense

<400> SEQUENCE: 2

```
Asp Cys Ala Ala Ala Ser Asn Gly Glu Trp Ser Ile Ala Asn Gly
1               5                   10                  15

Gly Val Ala Asn Tyr Lys Ala Tyr Ile Asp Arg Ile Arg His His Leu
            20                  25                  30

Val Ala Tyr Ser Asp Leu Arg Val Ile Leu Val Ile Glu Pro Asp Ser
        35                  40                  45

Leu Ala Asn Met Val Thr Asn Met Asn Val Pro Lys Cys Gln Gly Ala
    50                  55                  60

Ala Ser Thr Tyr Arg Glu Leu Thr Ile Tyr Ala Met Gln Arg Leu Asn
65                  70                  75                  80

Leu Pro Asn Val Ala Met Tyr Leu Asp Ala Gly His Ala Gly Trp Leu
                85                  90                  95

Gly Trp Pro Ala Asn Ile Gln Pro Ala Ala Asp Leu Phe Ala Asn Leu
            100                 105                 110

Tyr Lys Asp Ala Gly Arg Pro Ala Ala Val Arg Gly Leu Val Thr Asn
        115                 120                 125

Val Ser Asn Tyr Asn Gly Trp Asn Leu Thr Ser Pro Pro Tyr Thr
    130                 135                 140

Ser Pro Asn Pro Asn Tyr Asp Glu Arg Arg Tyr Val Glu Ala Phe Ala
145                 150                 155                 160

Pro Leu Leu Gln Ala Asn Gly Trp Asn Ala Arg Phe Ile Thr Asp Thr
                165                 170                 175

Gly Arg Ser Gly Lys Gln Pro Thr Gly Gln Ile Glu Trp Gly Asn Trp
            180                 185                 190

Cys Asn Ser Arg Gly Thr Gly Phe Gly Met Arg Pro Thr Ser Asn Thr
        195                 200                 205

Asn His Glu Leu Met Asp Ala Phe Val Trp Val Lys Pro Gly Gly Glu
    210                 215                 220

Ser Asp Gly Thr Ser Asp Thr Ser Ala Ala Arg Tyr Asp Arg Asn Cys
225                 230                 235                 240

Asp Ser Lys Ala Ala Met Lys Pro Ala Arg Glu Ala Gly Gln Trp Phe
                245                 250                 255

Arg Ala Tyr Phe Glu Met Leu Leu Thr Asn Ala Asn Pro Pro Phe
            260                 265                 270
```

<210> SEQ ID NO 3
<211> LENGTH: 1404
<212> TYPE: DNA
<213> ORGANISM: Talaromyces leycettanus

<400> SEQUENCE: 3

```
atgcggtctc tcctggctct tgcccctacc ctgctcgcgc tgttgttca ggctcagcaa     60 accatgtggg gtcaatgcgg tggtcagggc tggaccggac ctaccatctg tgtagcaggc    120
gcgacatgca gcacacagaa cccttggtat gcgcagtgca ccccagcacc taccgcgccg    180
```

```
acgaccttgc aaacaacaac tacgacgagc tcgaaatcgt ccacgaccac gagctcgaag    240
tcgtccacga ccacaggtgg aagtggcggt ggaactacga cctcaacgtc agccaccatc    300
accgcggctc catctggtaa cccatactcc ggataccagc tctatgtgaa ccaggaatac    360
tcgtccgagg tgtacgcgtc tgctattcct tcccttaccg gcactctggt cgcgaaggca    420
agcgccgcgg cagaggtgcc atctttcctg tggctggaca ctgcctccaa ggtgccactg    480
atgggcactt acttgcagga tatccaggcg aagaacgctg ctggcgccaa ccccccatat    540
gccggtcaat tcgtggttta cgacttgccg gatcgtgatt gcgctgcatt ggccagcaat    600
ggagagtact ccattgctaa caatggtgtt gccaactaca aggcttacat cgactccatc    660
cgcgcgcttc ttgttcaata ctcgaacgtc catgtcatcc ttgtgatcga gcccgacagc    720
ttggccaacc ttgtcaccaa cctgaatgtt cagaagtgtg ctaatgctca gagtgcttac    780
ctggagtgca tcaactatgc cctcactcag ttgaacctca agaacgttgc tatgtacatc    840
gatgctggtc atgctggatg gctcggctgg cccgccaacc ttagcccggc cgctcaactc    900
tttgcttccg tataccagaa tgcaagctcc ccagctgccg ttcgcggcct ggcaaccaac    960
gtggccaact ataatgcctg gtcgatcgcc acttgcccat cttacaccca aggcgacccc    1020
aactgcgacg agcagaaata catcaacgct ctggctccat gcttcagca acagggatgg   1080 tcatcagttc actttatcac cgataccggt aagtctggcc gtaacggtgt ccagcctacc   1140
aagcagaatg cctggggtga ctggtgcaac gttatcggaa ccggcttcgg tgtccgtccc   1200
accaccaaca ctggcgatcc attggaggat gctttcgtct gggtcaagcc tggtggtgag   1260
agtgatggta cttccaactc cacttcgcct cgctacgacg cccactgcgg ttacagtgat   1320
gctcttcagc ctgctcctga ggctggtacc tggttcgagg cttactttga gcaactcctt   1380
accaacgcca acccctcttt ctaa                                           1404
```

<210> SEQ ID NO 4
<211> LENGTH: 467
<212> TYPE: PRT
<213> ORGANISM: Talaromyces leycettanus

<400> SEQUENCE: 4

Met Arg Ser Leu Leu Ala Leu Ala Pro Thr Leu Leu Ala Pro Val Val
1               5                   10                  15

Gln Ala Gln Gln Thr Met Trp Gly Gln Cys Gly Gly Gln Gly Trp Thr
            20                  25                  30

Gly Pro Thr Ile Cys Val Ala Gly Ala Thr Cys Ser Thr Gln Asn Pro
        35                  40                  45

Trp Tyr Ala Gln Cys Thr Pro Ala Pro Thr Ala Pro Thr Thr Leu Gln
    50                  55                  60

Thr Thr Thr Thr Thr Ser Ser Lys Ser Ser Thr Thr Ser Ser Lys
65                  70                  75                  80

Ser Ser Thr Thr Thr Gly Gly Ser Gly Gly Thr Thr Thr Ser Thr
                85                  90                  95

Ser Ala Thr Ile Thr Ala Ala Pro Ser Gly Asn Pro Tyr Ser Gly Tyr
            100                 105                 110

Gln Leu Tyr Val Asn Gln Glu Tyr Ser Ser Glu Val Tyr Ala Ser Ala
        115                 120                 125

Ile Pro Ser Leu Thr Gly Thr Leu Val Ala Lys Ala Ser Ala Ala Ala
    130                 135                 140

Glu Val Pro Ser Phe Leu Trp Leu Asp Thr Ala Ser Lys Val Pro Leu

Met Gly Thr Tyr Leu Gln Asp Ile Gln Ala Lys Asn Ala Ala Gly Ala
145                 150                 155                 160

Asn Pro Pro Tyr Ala Gly Gln Phe Val Val Tyr Asp Leu Pro Asp Arg
            165                 170                 175

Asp Cys Ala Ala Leu Ala Ser Asn Gly Glu Tyr Ser Ile Ala Asn Asn
        180                 185                 190

Gly Val Ala Asn Tyr Lys Ala Tyr Ile Asp Ser Ile Arg Ala Leu Leu
    195                 200                 205

Val Gln Tyr Ser Asn Val His Val Ile Leu Val Ile Glu Pro Asp Ser
210                 215                 220

Leu Ala Asn Leu Val Thr Asn Leu Asn Val Gln Lys Cys Ala Asn Ala
225                 230                 235                 240

Gln Ser Ala Tyr Leu Glu Cys Ile Asn Tyr Ala Leu Thr Gln Leu Asn
            245                 250                 255

Leu Lys Asn Val Ala Met Tyr Ile Asp Ala Gly His Ala Gly Trp Leu
        260                 265                 270

Gly Trp Pro Ala Asn Leu Ser Pro Ala Ala Gln Leu Phe Ala Ser Val
    275                 280                 285

Tyr Gln Asn Ala Ser Ser Pro Ala Ala Val Arg Gly Leu Ala Thr Asn
290                 295                 300

Val Ala Asn Tyr Asn Ala Trp Ser Ile Ala Thr Cys Pro Ser Tyr Thr
305                 310                 315                 320

Gln Gly Asp Pro Asn Cys Asp Glu Gln Lys Tyr Ile Asn Ala Leu Ala
            325                 330                 335

Pro Leu Leu Gln Gln Gln Gly Trp Ser Ser Val His Phe Ile Thr Asp
        340                 345                 350

Thr Gly Lys Ser Gly Arg Asn Gly Val Gln Pro Thr Lys Gln Asn Ala
    355                 360                 365

Trp Gly Asp Trp Cys Asn Val Ile Gly Thr Gly Phe Gly Val Arg Pro
370                 375                 380

Thr Thr Asn Thr Gly Asp Pro Leu Glu Asp Ala Phe Val Trp Val Lys
385                 390                 395                 400

Pro Gly Gly Glu Ser Asp Gly Thr Ser Asn Ser Thr Ser Pro Arg Tyr
            405                 410                 415

Asp Ala His Cys Gly Tyr Ser Asp Ala Leu Gln Pro Ala Pro Glu Ala
        420                 425                 430

Gly Thr Trp Phe Glu Ala Tyr Phe Glu Gln Leu Leu Thr Asn Ala Asn
    435                 440                 445

Pro Ser Phe
465

<210> SEQ ID NO 5
<211> LENGTH: 640
<212> TYPE: DNA
<213> ORGANISM: Talaromyces byssochlamydoides

<400> SEQUENCE: 5
cgatagggac tgcgctgcag cagccagcaa tggagaattc tccattgccg acaatggagt    60
cgccttgtac aagcagtaca tcgacaacat taccgagtgg ctggtgacgt attcggatgt   120
ccacaccatc ctgatcattg aacccgacag cctggccaac ttggtcacca acctgaacgt   180
cgagaaatgc gcgaacgcag agagcgcgta tttggagtgc atcaactatg cgataacgaa   240
gctcaacctg cccaatgtgg ccatgtatct tgacgcgggt cacgccggat ggttaggctg   300

```
gtcggcaaac ctccagcccg cagcaaacct cttcgcttcc gtgtacaaga acgcctcatc    360
gccggcttcc gtgcgcggtc tggccaccaa cgtcgctaac tacaacgcct ggaccgtcag    420
tccgtgcccg tcgtacacgc agggcgactc caactgcgat gaagaggact atgtgaatgc    480
cctgggacca ctggtcgcgg cgcagggctt taacgcgcac tttatcaccg acacagcccg    540
caacggtgtc caacccaccc agcaacaaca atggggtgac tggtgcaacg tgatcggcac    600
cggctttggc gtgcgtccga ctaccaacac gggcaactct                          640
```

<210> SEQ ID NO 6
<211> LENGTH: 213
<212> TYPE: PRT
<213> ORGANISM: Talaromyces byssochlamydoides

<400> SEQUENCE: 6

```
Asp Arg Asp Cys Ala Ala Ala Ser Asn Gly Glu Phe Ser Ile Ala
1               5                   10                  15

Asp Asn Gly Val Ala Leu Tyr Lys Gln Tyr Ile Asp Asn Ile Thr Glu
            20                  25                  30

Trp Leu Val Thr Tyr Ser Asp Val His Thr Ile Leu Ile Glu Pro
        35                  40                  45

Asp Ser Leu Ala Asn Leu Val Thr Asn Leu Asn Val Glu Lys Cys Ala
    50                  55                  60

Asn Ala Glu Ser Ala Tyr Leu Glu Cys Ile Asn Tyr Ala Ile Thr Lys
65                  70                  75                  80

Leu Asn Leu Pro Asn Val Ala Met Tyr Leu Asp Ala Gly His Ala Gly
                85                  90                  95

Trp Leu Gly Trp Ser Ala Asn Leu Gln Pro Ala Ala Asn Leu Phe Ala
            100                 105                 110

Ser Val Tyr Lys Asn Ala Ser Ser Pro Ala Ser Val Arg Gly Leu Ala
        115                 120                 125

Thr Asn Val Ala Asn Tyr Asn Ala Trp Thr Val Ser Pro Cys Pro Ser
    130                 135                 140

Tyr Thr Gln Gly Asp Ser Asn Cys Asp Glu Glu Asp Tyr Val Asn Ala
145                 150                 155                 160

Leu Gly Pro Leu Val Ala Ala Gln Gly Phe Asn Ala His Phe Ile Thr
                165                 170                 175

Asp Thr Ala Arg Asn Gly Val Gln Pro Thr Gln Gln Gln Trp Gly
            180                 185                 190

Asp Trp Cys Asn Val Ile Gly Thr Gly Phe Gly Val Arg Pro Thr Thr
        195                 200                 205

Asn Thr Gly Asn Ser
    210
```

<210> SEQ ID NO 7
<211> LENGTH: 819
<212> TYPE: DNA
<213> ORGANISM: Corynascus thermophilus

<400> SEQUENCE: 7

```
agggactgtg ccgcggccgc gtccaatggc gagtggtcga ttgcgaacgg cggcgcggcc     60
aactacaggg gctacatcga caggatccgc cagctcctca tccaattctc ggacatccgg    120
accatcctgg tcatcgagcc cgactcgatg gccaacatgg tgacaaacct gaacgttgcc    180
aaatgcagca acgcccgctc gacgtaccat gagttgaccg tgtacgccct caagcaactc    240
```

```
aacctgcccc atgtcgccat gtatctcgac gccggccacg ccggctggct cggttggccc      300
gccaacatcc aaccggccgc cgacctgttt gccggcctct acaaagacgc gggtagcccg      360
gctgccgtcc gcggccttgc cacaaatgtt gccaactaca acgcctggag cctctcctcg      420
gccccgtcgt acacgtcgcc gaaccccaac tacgacgaga agcactacat cgaggccttc      480
agcccgctcc tgaacgcggc cggcttcccg gcacgcttca tcgtcgacac cggccgcaac      540
ggcaagcaac ctaccggtca actggagtgg ggcgactggt gcaacgtgag ggacaccggc      600
tttggcgtcc gcccgacggc caacacaggc cacgagctgg tcgatgcctt cgtctggatc      660
aagcccggcg gcgagtcgga cggcacgagc gacaccagcg ccgctcgcta cgactaccac      720
tgcggcctga gcgatgccct gaagcctgcc cccgaggccg tcagtggttc caggcctac       780 ttcgagcagc tgctcatcaa cgccaacccg ccgttttaa                             819
```

<210> SEQ ID NO 8
<211> LENGTH: 273
<212> TYPE: PRT
<213> ORGANISM: Corynascus thermophilus

<400> SEQUENCE: 8

```
Arg Arg Asp Cys Ala Ala Ala Ala Ser Asn Gly Glu Trp Ser Ile Ala
1               5                   10                  15

Asn Gly Gly Ala Ala Asn Tyr Arg Gly Tyr Ile Asp Arg Ile Arg Gln
            20                  25                  30

Leu Leu Ile Gln Phe Ser Asp Ile Arg Thr Ile Leu Val Ile Glu Pro
        35                  40                  45

Asp Ser Met Ala Asn Met Val Thr Asn Leu Asn Val Ala Lys Cys Ser
    50                  55                  60

Asn Ala Arg Ser Thr Tyr His Glu Leu Thr Val Tyr Ala Leu Lys Gln
65                  70                  75                  80

Leu Asn Leu Pro His Val Ala Met Tyr Leu Asp Ala Gly His Ala Gly
                85                  90                  95

Trp Leu Gly Trp Pro Ala Asn Ile Gln Pro Ala Ala Asp Leu Phe Ala
            100                 105                 110

Gly Leu Tyr Lys Asp Ala Gly Ser Pro Ala Ala Val Arg Gly Leu Ala
        115                 120                 125

Thr Asn Val Ala Asn Tyr Asn Ala Trp Ser Leu Ser Ser Ala Pro Ser
    130                 135                 140

Tyr Thr Ser Pro Asn Pro Asn Tyr Asp Glu Lys His Tyr Ile Glu Ala
145                 150                 155                 160

Phe Ser Pro Leu Leu Asn Ala Ala Gly Phe Pro Ala Arg Phe Ile Val
                165                 170                 175

Asp Thr Gly Arg Asn Gly Lys Gln Pro Thr Gly Gln Leu Glu Trp Gly
            180                 185                 190

Asp Trp Cys Asn Val Arg Asp Thr Gly Phe Gly Val Arg Pro Thr Ala
        195                 200                 205

Asn Thr Gly His Glu Leu Val Asp Ala Phe Val Trp Ile Lys Pro Gly
    210                 215                 220

Gly Glu Ser Asp Gly Thr Ser Asp Thr Ser Ala Ala Arg Tyr Asp Tyr
225                 230                 235                 240

His Cys Gly Leu Ser Asp Ala Leu Lys Pro Ala Pro Glu Ala Gly Gln
                245                 250                 255

Trp Phe Gln Ala Tyr Phe Glu Gln Leu Leu Ile Asn Ala Asn Pro Pro
            260                 265                 270
```

Phe

<210> SEQ ID NO 9
<211> LENGTH: 1170
<212> TYPE: DNA
<213> ORGANISM: Scytalidium indonesiacum
<220> FEATURE:
<221> NAME/KEY: misc_feature
<222> LOCATION: (340)..(348)
<223> OTHER INFORMATION: n is a, c, g, or t

<400> SEQUENCE: 9

```
atggctaagc agctgctgct cactgccgct cttgcggcca cttcgctggc tgccctcta      60
cttgaggagc gccagagctg ctcctcggtc tggggtcaat gcggtggcat caactacaac    120
ggcccgactt gctgcccgtc cggcagtgtt tgcacatacc tgaatgactg gtacagccag    180
tgcattcccg gccaggctca gcccggcacg actagcacca cggcccggac caccagcacc    240
agcaccagca cttcgtccgt ccgcccgacc accacctcca ataccctgt gacgactgct     300
cctccggcga ccaccatccc gggcggcgcc tcgagcacgn nnnnnnncg cagggactgc     360
gctgccgcgg cttcgaacgg cgagtgggcg atcgccaaca acggcgccaa caactacaag    420
ggatacatca accggatccg cgagattctc atttccttct cggatgtccg cacgatcctg    480
gtcatcgagc ccgactcgct ggccaacatg gtcaccaaca tgaacgtcgc caagtgcagc    540
ggcgccgcct cgacctaccg cgagttgacc gtctatgccc tcaagcagct cgacctcccg    600
cacgtcgcca tgtacatgga cgccggccac gctggctggc ttggctggcc cgccaacatc    660
cagcccgctg ctgagctctt cgccaagatc tacgaggatg ccggcaagcc ccgcgccgtc    720
cgcggtcttg ccaccaacgt cgccaactac aacgcctgga cgtctcgag cccgccgccg     780
tacaccagcc ccaaccccaa ctacgacgag aagcactaca tcgaggcctt ccgccctctc    840
ctcgaggccc gcggcttccc cgcccagttc atcgtcgacc agggccgcag cggcaagcag    900
cccaccggcc agaaggaatg gggccactgg tgcaatgcca ttggcaccgg cttcggtatg    960
cgcccgaccg ccaacactgg ccaccagtac gtcgacgcct tcgtctgggt caagcccggc   1020
ggtgagtgcg acggcaccag cgacacgacc gctgcccgct acgactacca ctgcggtctc   1080
gaggatgccc tcaagcccgc ccctgaagct ggtcagtggt ttcaagctta ttttgttcag   1140
ctcttgcaaa acgccaatcc gccgttctaa                                    1170
```

<210> SEQ ID NO 10
<211> LENGTH: 389
<212> TYPE: PRT
<213> ORGANISM: Scytalidium indonesiacum
<220> FEATURE:
<221> NAME/KEY: misc_feature
<222> LOCATION: (114)..(116)
<223> OTHER INFORMATION: Xaa can be any naturally occurring amino acid

<400> SEQUENCE: 10

Met Ala Lys Gln Leu Leu Leu Thr Ala Ala Leu Ala Ala Thr Ser Leu
1               5                   10                  15

Ala Ala Pro Leu Leu Glu Glu Arg Gln Ser Cys Ser Ser Val Trp Gly
            20                  25                  30

Gln Cys Gly Gly Ile Asn Tyr Asn Gly Pro Thr Cys Cys Pro Ser Gly
        35                  40                  45

Ser Val Cys Thr Tyr Leu Asn Asp Trp Tyr Ser Gln Cys Ile Pro Gly
    50                  55                  60

Gln Ala Gln Pro Gly Thr Thr Ser Thr Thr Ala Arg Thr Thr Ser Thr

```
              65                  70                  75                  80
Ser Thr Ser Thr Ser Ser Val Arg Pro Thr Thr Ser Asn Thr Pro
                    85                  90                  95
Val Thr Thr Ala Pro Pro Ala Thr Thr Ile Pro Gly Gly Ala Ser Ser
                100                 105                 110
Thr Xaa Xaa Xaa Arg Arg Asp Cys Ala Ala Ala Ser Asn Gly Glu
            115                 120                 125
Trp Ala Ile Ala Asn Asn Gly Ala Asn Tyr Lys Gly Tyr Ile Asn
        130                 135                 140
Arg Ile Arg Glu Ile Leu Ile Ser Phe Ser Asp Val Arg Thr Ile Leu
145                 150                 155                 160
Val Ile Glu Pro Asp Ser Leu Ala Asn Met Val Thr Asn Met Asn Val
                165                 170                 175
Ala Lys Cys Ser Gly Ala Ala Ser Thr Tyr Arg Glu Leu Thr Val Tyr
                180                 185                 190
Ala Leu Lys Gln Leu Asp Leu Pro His Val Ala Met Tyr Met Asp Ala
            195                 200                 205
Gly His Ala Gly Trp Leu Gly Trp Pro Ala Asn Ile Gln Pro Ala Ala
        210                 215                 220
Glu Leu Phe Ala Lys Ile Tyr Glu Asp Ala Gly Lys Pro Arg Ala Val
225                 230                 235                 240
Arg Gly Leu Ala Thr Asn Val Ala Asn Tyr Asn Ala Trp Ser Val Ser
                245                 250                 255
Ser Pro Pro Pro Tyr Thr Ser Pro Asn Pro Asn Tyr Asp Glu Lys His
                260                 265                 270
Tyr Ile Glu Ala Phe Arg Pro Leu Leu Glu Ala Arg Gly Phe Pro Ala
            275                 280                 285
Gln Phe Ile Val Asp Gln Gly Arg Ser Gly Lys Gln Pro Thr Gly Gln
        290                 295                 300
Lys Glu Trp Gly His Trp Cys Asn Ala Ile Gly Thr Gly Phe Gly Met
305                 310                 315                 320
Arg Pro Thr Ala Asn Thr Gly His Gln Tyr Val Asp Ala Phe Val Trp
                325                 330                 335
Val Lys Pro Gly Gly Glu Cys Asp Gly Thr Ser Asp Thr Thr Ala Ala
                340                 345                 350
Arg Tyr Asp Tyr His Cys Gly Leu Glu Asp Ala Leu Lys Pro Ala Pro
            355                 360                 365
Glu Ala Gly Gln Trp Phe Gln Ala Tyr Phe Val Gln Leu Leu Gln Asn
        370                 375                 380
Ala Asn Pro Pro Phe
385

<210> SEQ ID NO 11
<211> LENGTH: 604
<212> TYPE: DNA
<213> ORGANISM: Corynascus thermophilus

<400> SEQUENCE: 11
cacggcgccc tctacttcgt gtccatggat gccgatggcg gcatgtccaa gtactcgggc      60
aacaaggcgg gcgccaagta cggtaccggc tactgtgacg ctcagtgccc ccgcgaccct     120
aagttcatca cggcgaggc caacgtggag ggctgggaga gctcgaccaa cgatgccaac     180
gccggcacgg gcaggtacgg cagctgctgc tccgaaatgg atgtcgggaa gaccaacaac     240
atggaccccg ccttcacgcc ccatccttgc acatcatcgg ccagtcgagc tgcgaggtgc     300
```

```
atagtgcggc gaacctacgg ctcggaccgc tacccccatg atgcccccg tttcggacca    360 tttctgtcat accgccatgc caccttgacc ttctactgga agggtttgac cgtcgacaca    420
accaggaaac tcacggacgt cacgcagcta ctccatgact cgtccgggca cctacgacag    480
atcatttgtc gattcggtcc ttgcgcgacg acaaagtttc taacttgaca cgttcttgtt    540
ggaagctagc ttcctgatcg agcccttgtg gaatgacgct cgatcaaaaa tctggttcca    600
cgag                                                                604
```

<210> SEQ ID NO 12
<211> LENGTH: 175
<212> TYPE: PRT
<213> ORGANISM: Corynascus thermophilus

<400> SEQUENCE: 12

```
His Gly Ala Leu Tyr Phe Val Ser Met Asp Ala Asp Gly Gly Met Ser
1               5                   10                  15

Lys Tyr Ser Gly Asn Lys Ala Gly Ala Lys Tyr Gly Thr Gly Tyr Cys
            20                  25                  30

Asp Ala Gln Cys Pro Arg Asp Leu Lys Phe Ile Asn Gly Glu Ala Asn
        35                  40                  45

Val Glu Gly Trp Glu Ser Ser Thr Asn Asp Ala Asn Ala Gly Thr Gly
    50                  55                  60

Arg Tyr Gly Ser Cys Cys Ser Glu Met Asp Val Gly Lys Thr Asn Asn
65                  70                  75                  80

Met Asp Pro Ala Phe Thr Pro His Pro Cys Thr Ser Ala Ser Arg
                85                  90                  95

Ala Ala Arg Cys Ile Val Arg Arg Thr Tyr Gly Ser Asp Arg Tyr Pro
            100                 105                 110

His Asp Ala Pro Arg Phe Gly Pro Phe Leu Ser Tyr Arg His Ala Thr
        115                 120                 125

Leu Thr Phe Tyr Trp Lys Gly Leu Thr Val Asp Thr Thr Arg Lys Leu
    130                 135                 140

Thr Asp Val Thr Gln Leu Leu His Asp Ser Ser Gly His Leu Arg Gln
145                 150                 155                 160

Ile Ile Cys Arg Phe Gly Pro Cys Ala Thr Thr Lys Phe Leu Thr
                165                 170                 175
```

<210> SEQ ID NO 13
<211> LENGTH: 299
<212> TYPE: DNA
<213> ORGANISM: Chaetomium senegalense

<400> SEQUENCE: 13

```
tgcggtgtca cggtgccctg tacttcgtgt ccatggatgc cgatggtggt gcgtccaagt     60
accccagcaa cagggctggt gccaagtacg gtaccggcta ctgcgattcg cagtgcccgc    120
gcgacatcaa gttcatcaat ggcgaggcca acgttgaggg ttggaatccg tccgagagcg    180
atcccaacgc cggctttggc cgctatggta cctgctgcgc cgaaatggat atttggaagc    240
gtccagaagc taatatggca cttgctgcgc tgagatggat atttgggaag cgtccatca     299
```

<210> SEQ ID NO 14
<211> LENGTH: 99
<212> TYPE: PRT
<213> ORGANISM: Chaetomium senegalense

<400> SEQUENCE: 14

```
Arg Cys His Gly Ala Leu Tyr Phe Val Ser Met Asp Ala Asp Gly Gly
1               5                   10                  15

Ala Ser Lys Tyr Pro Ser Asn Arg Ala Gly Ala Lys Tyr Gly Thr Gly
            20                  25                  30

Tyr Cys Asp Ser Gln Cys Pro Arg Asp Ile Lys Phe Ile Asn Gly Glu
                35                  40                  45

Ala Asn Val Glu Gly Trp Asn Pro Ser Glu Ser Asp Pro Asn Ala Gly
        50                  55                  60

Phe Gly Arg Tyr Gly Thr Cys Cys Ala Glu Met Asp Ile Trp Lys Arg
65                  70                  75                  80

Pro Glu Ala Asn Met Ala Leu Ala Ala Leu Arg Trp Ile Phe Gly Lys
                85                  90                  95

Arg Pro Ser
```

<210> SEQ ID NO 15
<211> LENGTH: 1614
<212> TYPE: DNA
<213> ORGANISM: Talaromyces leycettanus
<220> FEATURE:
<221> NAME/KEY: misc_feature
<222> LOCATION: (883)..(885)
<223> OTHER INFORMATION: n is a, c, g, or t

<400> SEQUENCE: 15

```
atggccagcc tcttctcttt caagatgtac aaggccgctc tggtcctctc ctctctcctt      60
gcggccaccc aggcccagca ggccggcacc ctgaccaccg aaacccatcc ttctctgacc     120
tggcagcaat gctctgccgg cggcagctgc accactcaga cggcaaggt  cgtcatcgac     180
gccaactggc gctgggttca cagcaccagc ggctcgaaca actgctacac tggcaacact     240
tgggatgcta ctctctgccc tgacgacgtg acttgcgctg ccaactgcgc cctggacggc     300
gctgactact cgggcaccta cggtgtcacc accagcggca actctctgcg cctgaacttc     360
gtcacccagg cgtcgcagaa gaacgtcggc tctcgtctct atctgatgga gaatgacaca     420
acctaccaga tcttcaagtt gctgaaccag gagttcacct ttgacgttga tgtctccaac     480
cttccctgcg gtctcaacgg tgctctctac ctggttgcca tggatgccga cggcggcatg     540
gccaagtacc caaccaacaa ggctggtgcg aagtacggaa ccggttactg cgactcccag     600
tgccctcgag acctgaaatt catcaacggt gaggccaatg ttgagggatg cagccttct      660
tccaatgacc ccaactctgg cattggcaac cacggctctt gctgtgctga atggacatc      720
tgggaggcca acagcatctc ccatgccgtc actcctcacc cttgcgacac cccgggacag     780
gtcatgtgca ccggcaacaa ctgtggtggc acttacagca ctactcgcta tgctggcact     840
tgcgatcctg atggctgcga tttgagtcca gactgtgata atnnntaccg cgtgggcgac     900
cactccttct acggccccaa acagatcgtc gacaccagct ccaagttcac tgttgttact     960
cagttcctca ccgatgatgg cacctccacc ggcaccctca gcgagatcag gcgcttctac    1020
gttcagaacg gccaggtcat ccccaactcc gtgtccacga tcagcggcgt ctccggcaac    1080
tccatcacca ccgagttctg cacggcccag aagcaggctt cggcgacac  tgatgacttc    1140
agcaagcacg gcggtctgtc tggcatgtcc gccgccctct cccagggtat ggttctcgtc    1200
atgagcttgt gggacgacca cgccgccaac atgctctggc ttgacagcac ctacccgacc    1260
aacgccacct cttccacccc cggtgccgcc cgtggtactt gcgacatctc ctccggtgtc    1320
cccgccgatg ttgagtccaa cgaccccaac gcctacgtcg tctactccaa catcaaggtc    1380
```

-continued

```
ggcccgatcg gctctacctt cagcagctct ggctctggct ctagctccag ctccagcacc    1440
accaccacca ccaccgcttc cccaaccacg accacctcca gcgcttccag caccggcact    1500
ggcgttgctc agcactgggg tcagtgcggt ggccagggat ggaccggtcc gaccacctgc    1560
gttagcccct acacctgcca ggagctgaac ccctactact accagtgcct gtaa          1614
```

```
<210> SEQ ID NO 16
<211> LENGTH: 539
<212> TYPE: PRT
<213> ORGANISM: Talaromyces leycettanus
<220> FEATURE:
<221> NAME/KEY: misc_feature
<222> LOCATION: (295)..(297)
<223> OTHER INFORMATION: Xaa can be any naturally occurring amino acid

<400> SEQUENCE: 16
```

Met Ala Ser Leu Phe Ser Phe Lys Met Tyr Lys Ala Ala Leu Val Leu
1               5                   10                  15

Ser Ser Leu Leu Ala Ala Thr Gln Ala Gln Gln Ala Gly Thr Leu Thr
            20                  25                  30

Thr Glu Thr His Pro Ser Leu Thr Trp Gln Gln Cys Ser Ala Gly Gly
        35                  40                  45

Ser Cys Thr Thr Gln Asn Gly Lys Val Val Ile Asp Ala Asn Trp Arg
    50                  55                  60

Trp Val His Ser Thr Ser Gly Ser Asn Asn Cys Tyr Thr Gly Asn Thr
65                  70                  75                  80

Trp Asp Ala Thr Leu Cys Pro Asp Asp Val Thr Cys Ala Ala Asn Cys
                85                  90                  95

Ala Leu Asp Gly Ala Asp Tyr Ser Gly Thr Tyr Gly Val Thr Thr Ser
            100                 105                 110

Gly Asn Ser Leu Arg Leu Asn Phe Val Thr Gln Ala Ser Gln Lys Asn
        115                 120                 125

Val Gly Ser Arg Leu Tyr Leu Met Glu Asn Asp Thr Thr Tyr Gln Ile
    130                 135                 140

Phe Lys Leu Leu Asn Gln Glu Phe Thr Phe Asp Val Asp Val Ser Asn
145                 150                 155                 160

Leu Pro Cys Gly Leu Asn Gly Ala Leu Tyr Leu Val Ala Met Asp Ala
                165                 170                 175

Asp Gly Gly Met Ala Lys Tyr Pro Thr Asn Lys Ala Gly Ala Lys Tyr
            180                 185                 190

Gly Thr Gly Tyr Cys Asp Ser Gln Cys Pro Arg Asp Leu Lys Phe Ile
        195                 200                 205

Asn Gly Glu Ala Asn Val Glu Gly Trp Gln Pro Ser Ser Asn Asp Pro
    210                 215                 220

Asn Ser Gly Ile Gly Asn His Gly Ser Cys Cys Ala Glu Met Asp Ile
225                 230                 235                 240

Trp Glu Ala Asn Ser Ile Ser His Ala Val Thr Pro His Pro Cys Asp
                245                 250                 255

Thr Pro Gly Gln Val Met Cys Thr Gly Asn Asn Cys Gly Gly Thr Tyr
            260                 265                 270

Ser Thr Thr Arg Tyr Ala Gly Thr Cys Asp Pro Asp Gly Cys Asp Leu
        275                 280                 285

Ser Pro Asp Cys Asp Asn Xaa Xaa Xaa Tyr Arg Val Gly Asp His Ser
    290                 295                 300

Phe Tyr Gly Pro Lys Gln Ile Val Asp Thr Ser Ser Lys Phe Thr Val
305                 310                 315                 320

Val Thr Gln Phe Leu Thr Asp Asp Gly Thr Ser Thr Gly Thr Leu Ser
            325                 330                 335

Glu Ile Arg Arg Phe Tyr Val Gln Asn Gly Gln Val Ile Pro Asn Ser
        340                 345                 350

Val Ser Thr Ile Ser Gly Val Ser Gly Asn Ser Ile Thr Thr Glu Phe
            355                 360                 365

Cys Thr Ala Gln Lys Gln Ala Phe Gly Asp Thr Asp Asp Phe Ser Lys
        370                 375                 380

His Gly Gly Leu Ser Gly Met Ser Ala Ala Leu Ser Gln Gly Met Val
385                 390                 395                 400

Leu Val Met Ser Leu Trp Asp Asp His Ala Ala Asn Met Leu Trp Leu
                405                 410                 415

Asp Ser Thr Tyr Pro Thr Asn Ala Thr Ser Ser Thr Pro Gly Ala Ala
            420                 425                 430

Arg Gly Thr Cys Asp Ile Ser Ser Gly Val Pro Ala Asp Val Glu Ser
        435                 440                 445

Asn Asp Pro Asn Ala Tyr Val Val Tyr Ser Asn Ile Lys Val Gly Pro
    450                 455                 460

Ile Gly Ser Thr Phe Ser Ser Ser Gly Ser Gly Ser Ser Ser Ser Ser
465                 470                 475                 480

Ser Thr Thr Thr Thr Thr Thr Ala Ser Pro Thr Thr Thr Thr Ser Ser
                485                 490                 495

Ala Ser Ser Thr Gly Thr Gly Val Ala Gln His Trp Gly Gln Cys Gly
            500                 505                 510

Gly Gln Gly Trp Thr Gly Pro Thr Thr Cys Val Ser Pro Tyr Thr Cys
        515                 520                 525

Gln Glu Leu Asn Pro Tyr Tyr Tyr Gln Cys Leu
    530                 535

<210> SEQ ID NO 17
<211> LENGTH: 505
<212> TYPE: DNA
<213> ORGANISM: Corynascus thermophilus

<400> SEQUENCE: 17
tgctactcgg gcaacaagtg ggatacttcg tactgcaacg atggtccttc ttgcgcctcc      60
aagtgctgcg tcgacggtgc cgagtacagc agcacctatg catcaccac gagcggcaac     120 tccctgagcc tcaagttcgt caccaagggc cagtactcga ccaacgtcgg ctcgcgtacc     180
tacctgatgg agaacgagtc caagtaccag gtgttcgagc tcctcggcaa cgagttcacc     240
ttcgacgtcg acgtctccaa cctcggctgc ggcctcaacg cgccctcta cttcgtgtcc     300 atggatgccg atgcggcat gtccaagtac tcgggcaaca aggcgggcgc caagtacggt     360
accggctact gtgacgctca gtgccccgc gacctcaagt tcatcaacgg cgaggccaac     420
gtggagggct gggagagctc gaccaacgat gccaacgccg gcacgggcag gtacggcagc     480
tgctgctccg agatggatat ttggg                                          505

<210> SEQ ID NO 18
<211> LENGTH: 168
<212> TYPE: PRT
<213> ORGANISM: Corynascus thermophilus

<400> SEQUENCE: 18

Cys Tyr Ser Gly Asn Lys Trp Asp Thr Ser Tyr Cys Asn Asp Gly Pro
1               5                   10                  15

Ser Cys Ala Ser Lys Cys Cys Val Asp Gly Ala Glu Tyr Ser Ser Thr
            20                  25                  30

Tyr Gly Ile Thr Thr Ser Gly Asn Ser Leu Ser Leu Lys Phe Val Thr
        35                  40                  45

Lys Gly Gln Tyr Ser Thr Asn Val Gly Ser Arg Thr Tyr Leu Met Glu
    50                  55                  60

Asn Glu Ser Lys Tyr Gln Val Phe Glu Leu Leu Gly Asn Glu Phe Thr
65                  70                  75                  80

Phe Asp Val Asp Val Ser Asn Leu Gly Cys Gly Leu Asn Gly Ala Leu
                85                  90                  95

Tyr Phe Val Ser Met Asp Ala Asp Gly Met Ser Lys Tyr Ser Gly
            100                 105                 110

Asn Lys Ala Gly Ala Lys Tyr Gly Thr Gly Tyr Cys Asp Ala Gln Cys
            115                 120                 125

Pro Arg Asp Leu Lys Phe Ile Asn Gly Glu Ala Asn Val Glu Gly Trp
        130                 135                 140

Glu Ser Ser Thr Asn Asp Ala Asn Ala Gly Thr Gly Arg Tyr Gly Ser
145                 150                 155                 160

Cys Cys Ser Glu Met Asp Ile Trp
                165

<210> SEQ ID NO 19
<211> LENGTH: 376
<212> TYPE: DNA
<213> ORGANISM: Remersonia thermophila

<400> SEQUENCE: 19
acgtttgatg tggatgtctc caacatcggc tgcggcctga acggcgccct gtacttcgtc      60
tcgatggacc tcgacggtgg cctgtcgcgc ttcccgggca acaaggccgg tgccaagtac     120
ggcacgggct actgcgacgc ccagtgcccg cgcgacatca gttcatcaa cggcgaggcc     180 aacgttgagg gctggagcgg ctcgaccaac gaccccaacg ccggcgccgg ccgctacggc     240
acttgctgct ccgagatgga catctgggag ccaacaaca tggccaccgc ctacaccccg     300 caccctttgca ccatcatcgg ccagagccgc tgcgagggcg actcgtgcgg cggcacctac     360
agcaacgacc gctacg                                                    376

<210> SEQ ID NO 20
<211> LENGTH: 125
<212> TYPE: PRT
<213> ORGANISM: Remersonia thermophila

<400> SEQUENCE: 20

Thr Phe Asp Val Asp Val Ser Asn Ile Gly Cys Gly Leu Asn Gly Ala
1               5                   10                  15

Leu Tyr Phe Val Ser Met Asp Leu Asp Gly Gly Leu Ser Arg Phe Pro
            20                  25                  30

Gly Asn Lys Ala Gly Ala Lys Tyr Gly Thr Gly Tyr Cys Asp Ala Gln
        35                  40                  45

Cys Pro Arg Asp Ile Lys Phe Ile Asn Gly Glu Ala Asn Val Glu Gly
    50                  55                  60

Trp Ser Gly Ser Thr Asn Asp Pro Asn Ala Gly Ala Gly Arg Tyr Gly
65                  70                  75                  80

Thr Cys Cys Ser Glu Met Asp Ile Trp Glu Ala Asn Asn Met Ala Thr
                85                  90                  95

```
Ala Tyr Thr Pro His Pro Cys Thr Ile Ile Gly Gln Ser Arg Cys Glu
            100                 105                 110
Gly Asp Ser Cys Gly Gly Thr Tyr Ser Asn Asp Arg Tyr
        115                 120                 125
```

<210> SEQ ID NO 21
<211> LENGTH: 1107
<212> TYPE: DNA
<213> ORGANISM: Scytalidium indonesiacum

<400> SEQUENCE: 21

```
cacggcgccc tgtacttcgt ctccatggac gccgatggtg gtctcagccg ctatcctggc      60
aacaaggctg gtgccaagta cggtaccggc tactgcgatg ctcagtgccc ccgtgacatc     120
aagttcatca acggcgaggc caacattgag ggctggaccg gctccaccaa cgaccccaac     180
gccggtgcgg gccgctatgg tacctgctgc tctgagatgg atatctggga ggccaacaac     240
atggctactg ccttcactcc tcacccttgc accatcattg gccagagccg ctgcgagggc     300
gactcgtgcg gtggcaccta cagcaacgag cgctatgccg gtgtctgcga ccccgatggc     360
tgcgacttca actcgtaccg ccagggcaac aagaccttct acggcaaggg catgaccgtc     420
gacaccacca agaagctcac cgtcgtcacc cagttcctca aggacgccaa cggcgatctc     480
ggcgagatca gcgcttcta cgtccaggat ggcaagatca tccccaactc cgagtccacc     540
atccccggcg tcgagggcaa ctccatcacc caggactggt gcgaccgcca agaggttgct     600
tttggcgaca ttgacgactt caaccgcaag ggcggcatga agcagatggg caaggccctc     660
gccgccccca tggtcctggt catgtccatc tgggatgacc acgcctccaa catgctctgg     720
ctcgactcga ccttccctgt cgatgccgct ggcaagcccg gtgccgagcg cggtgcctgc     780
ccgaccacct cgggtgtccc tgctgaggtt gaggccgagg cccccaacag caacgtcgtc     840
ttctccaaca tccgcttcgg ccccatcggc tcgaccgttg ctggtctccc cggcgccggc     900
aatgcggca caacggcgg caaccccccg cccgccacca ccaccacctc ctcggctccg      960
gccaccacca ccaccgccag cgctggcccc aaggctggcc gctggcagca gtgcggcggc    1020
atcggcttca ctggcccgac ccagtgcgag aagccctaca cttgcaccaa gctcaacgac    1080
tgtactctca gtgcctgtaa attctga                                        1107
```

<210> SEQ ID NO 22
<211> LENGTH: 368
<212> TYPE: PRT
<213> ORGANISM: Scytalidium indonesiacum

<400> SEQUENCE: 22

```
His Gly Ala Leu Tyr Phe Val Ser Met Asp Ala Asp Gly Gly Leu Ser
1               5                   10                  15
Arg Tyr Pro Gly Asn Lys Ala Gly Ala Lys Tyr Gly Thr Gly Tyr Cys
            20                  25                  30
Asp Ala Gln Cys Pro Arg Asp Ile Lys Phe Ile Asn Gly Glu Ala Asn
        35                  40                  45
Ile Glu Gly Trp Thr Gly Ser Thr Asn Asp Pro Asn Ala Gly Ala Gly
    50                  55                  60
Arg Tyr Gly Thr Cys Cys Ser Glu Met Asp Ile Trp Glu Ala Asn Asn
65                  70                  75                  80
Met Ala Thr Ala Phe Thr Pro His Pro Cys Thr Ile Ile Gly Gln Ser
                85                  90                  95
Arg Cys Glu Gly Asp Ser Cys Gly Gly Thr Tyr Ser Asn Glu Arg Tyr
```

|     |     |     |     |     |     |     |     |     |     |     |     |
| --- | --- | --- | --- | --- | --- | --- | --- | --- | --- | --- | --- |
|     |     |     | 100 |     |     | 105 |     |     |     | 110 |     |
| Ala | Gly | Val | Cys | Asp | Pro | Asp | Gly | Cys | Asp | Phe | Asn | Ser | Tyr | Arg | Gln |
|     |     |     | 115 |     |     |     |     | 120 |     |     |     | 125 |     |     |     |
| Gly | Asn | Lys | Thr | Phe | Tyr | Gly | Lys | Gly | Met | Thr | Val | Asp | Thr | Thr | Lys |
|     |     | 130 |     |     |     |     | 135 |     |     |     |     | 140 |     |     |     |
| Lys | Leu | Thr | Val | Val | Thr | Gln | Phe | Leu | Lys | Asp | Ala | Asn | Gly | Asp | Leu |
| 145 |     |     |     |     | 150 |     |     |     |     | 155 |     |     |     |     | 160 |
| Gly | Glu | Ile | Lys | Arg | Phe | Tyr | Val | Gln | Asp | Gly | Lys | Ile | Ile | Pro | Asn |
|     |     |     |     | 165 |     |     |     |     | 170 |     |     |     |     | 175 |     |
| Ser | Glu | Ser | Thr | Ile | Pro | Gly | Val | Glu | Gly | Asn | Ser | Ile | Thr | Gln | Asp |
|     |     |     | 180 |     |     |     |     | 185 |     |     |     |     | 190 |     |     |
| Trp | Cys | Asp | Arg | Gln | Lys | Val | Ala | Phe | Gly | Asp | Ile | Asp | Asp | Phe | Asn |
|     |     | 195 |     |     |     |     | 200 |     |     |     |     | 205 |     |     |     |
| Arg | Lys | Gly | Gly | Met | Lys | Gln | Met | Gly | Lys | Ala | Leu | Ala | Gly | Pro | Met |
|     | 210 |     |     |     |     | 215 |     |     |     |     | 220 |     |     |     |     |
| Val | Leu | Val | Met | Ser | Ile | Trp | Asp | Asp | His | Ala | Ser | Asn | Met | Leu | Trp |
| 225 |     |     |     |     | 230 |     |     |     |     | 235 |     |     |     |     | 240 |
| Leu | Asp | Ser | Thr | Phe | Pro | Val | Asp | Ala | Ala | Gly | Lys | Pro | Gly | Ala | Glu |
|     |     |     |     | 245 |     |     |     |     | 250 |     |     |     |     | 255 |     |
| Arg | Gly | Ala | Cys | Pro | Thr | Thr | Ser | Gly | Val | Pro | Ala | Glu | Val | Glu | Ala |
|     |     |     | 260 |     |     |     |     | 265 |     |     |     |     | 270 |     |     |
| Glu | Ala | Pro | Asn | Ser | Asn | Val | Val | Phe | Ser | Asn | Ile | Arg | Phe | Gly | Pro |
|     |     | 275 |     |     |     |     | 280 |     |     |     |     | 285 |     |     |     |
| Ile | Gly | Ser | Thr | Val | Ala | Gly | Leu | Pro | Gly | Ala | Gly | Asn | Gly | Gly | Asn |
|     | 290 |     |     |     |     | 295 |     |     |     |     | 300 |     |     |     |     |
| Asn | Gly | Gly | Asn | Pro | Pro | Pro | Ala | Thr | Thr | Thr | Thr | Ser | Ser | Ala | Pro |
| 305 |     |     |     |     | 310 |     |     |     |     | 315 |     |     |     |     | 320 |
| Ala | Thr | Thr | Thr | Thr | Ala | Ser | Ala | Gly | Pro | Lys | Ala | Gly | Arg | Trp | Gln |
|     |     |     |     | 325 |     |     |     |     | 330 |     |     |     |     | 335 |     |
| Gln | Cys | Gly | Gly | Ile | Gly | Phe | Thr | Gly | Pro | Thr | Gln | Cys | Glu | Lys | Pro |
|     |     |     | 340 |     |     |     |     | 345 |     |     |     |     | 350 |     |     |
| Tyr | Thr | Cys | Thr | Lys | Leu | Asn | Asp | Cys | Thr | Leu | Ser | Ala | Cys | Lys | Phe |
|     |     |     |     | 355 |     |     |     |     | 360 |     |     |     |     | 365 |     |

<210> SEQ ID NO 23
<211> LENGTH: 793
<212> TYPE: DNA
<213> ORGANISM: Talaromyces byssochlamydoides
<220> FEATURE:
<221> NAME/KEY: misc_feature
<222> LOCATION: (134)..(136)
<223> OTHER INFORMATION: n is a, c, g, or t

<400> SEQUENCE: 23

```
acttgagttt atcgatggcc aggccaacgt tgagggctgg cagccgtctt cgaacaacgc      60
caatacaggt attggcaacc atggctcctg ctgtgcggaa atggatattt gggaagcgtc     120
cagaaaaggg ctcnnncatg cggtgactcc gcacccatgc gacacaccgg ccagacaat      180
gtgcgagggg aacgactgtg gtggcacgta ttccaccaat cgctatgcag gcacctgcga     240
tcctgacggc tgcgacttca accctaccg catgggcaac cattctttct acggccctgg     300
ggagattgtc gatactaccc agcccttcac tgtcgtgaca cagttcctta ccgatgatgg     360
cacggatact ggcactctca gcagatcaa acgcttctac gtccaaaacg gaaagtcat     420
tcctcagccg aactccgaca ttgccggcgt gactggcaac tcgatcacca gcgagttttg     480
cgatgcccag aagacggctt tcggcgacat taacaacttt gatacacacg gcggtctggc     540
```

```
cagtatggga gctgcgctgc agcagggtat ggttctggtg atgagtctgt gggacgatta      600
cgcggcaaac atgctgtggt tggacagcat ttatccaaca aatgcatctg ctagcactcc      660
tggtgctgct cgtggaacct gttcgacgag ctccggtgtc ccatcgcaag tcgagtcgca      720
gagccccaac gcctacgtga cgtactccaa cattaaagtt ggaccaatca actcgacctt      780
caccacttcg taa                                                         793
```

<210> SEQ ID NO 24
<211> LENGTH: 263
<212> TYPE: PRT
<213> ORGANISM: Talaromyces byssochlamydoides
<220> FEATURE:
<221> NAME/KEY: misc_feature
<222> LOCATION: (45)..(45)
<223> OTHER INFORMATION: Xaa can be any naturally occurring amino acid

<400> SEQUENCE: 24

```
Leu Glu Phe Ile Asp Gly Gln Ala Asn Val Glu Gly Trp Gln Pro Ser
1               5                   10                  15

Ser Asn Asn Ala Asn Thr Gly Ile Gly Asn His Gly Ser Cys Cys Ala
            20                  25                  30

Glu Met Asp Ile Trp Glu Ala Ser Arg Lys Gly Leu Xaa His Ala Val
        35                  40                  45

Thr Pro His Pro Cys Asp Thr Pro Gly Gln Thr Met Cys Glu Gly Asn
    50                  55                  60

Asp Cys Gly Gly Thr Tyr Ser Thr Asn Arg Tyr Ala Gly Thr Cys Asp
65                  70                  75                  80

Pro Asp Gly Cys Asp Phe Asn Pro Tyr Arg Met Gly Asn His Ser Phe
                85                  90                  95

Tyr Gly Pro Gly Glu Ile Val Asp Thr Thr Gln Pro Phe Thr Val Val
            100                 105                 110

Thr Gln Phe Leu Thr Asp Asp Gly Thr Asp Thr Gly Thr Leu Ser Glu
        115                 120                 125

Ile Lys Arg Phe Tyr Val Gln Asn Gly Lys Val Ile Pro Gln Pro Asn
    130                 135                 140

Ser Asp Ile Ala Gly Val Thr Gly Asn Ser Ile Thr Ser Glu Phe Cys
145                 150                 155                 160

Asp Ala Gln Lys Thr Ala Phe Gly Asp Ile Asn Asn Phe Asp Thr His
                165                 170                 175

Gly Gly Leu Ala Ser Met Gly Ala Ala Leu Gln Gln Gly Met Val Leu
            180                 185                 190

Val Met Ser Leu Trp Asp Asp Tyr Ala Ala Asn Met Leu Trp Leu Asp
        195                 200                 205

Ser Ile Tyr Pro Thr Asn Ala Ser Ala Ser Thr Pro Gly Ala Ala Arg
    210                 215                 220

Gly Thr Cys Ser Thr Ser Ser Gly Val Pro Ser Gln Val Glu Ser Gln
225                 230                 235                 240

Ser Pro Asn Ala Tyr Val Thr Tyr Ser Asn Ile Lys Val Gly Pro Ile
                245                 250                 255

Asn Ser Thr Phe Thr Thr Ser
            260
```

<210> SEQ ID NO 25
<211> LENGTH: 726
<212> TYPE: DNA
<213> ORGANISM: Thermomucor indicae-seudaticae

<400> SEQUENCE: 25

```
atgaaaaata caggatttgt taaatgtgtt attgttgtat tctctaggta aagattatac    60
tggcgcgact tgctgtgtca gcggatacga atgcctcaag gccgatgtct ggtactctca   120
atgcttgccc aagtaccagg gttcatccgc ttcctcggtc aatccttcca gcgttactgc   180
agtgtccacc gtaccgacta cttcttcgcc tgcctcaaag actgccatta atatgaagac   240
gaccactacc acgaccacga ccacggcctc tgctaagccc accacaaggt ctgctactag   300
ttatgcgtcc aagaccataa cctcttcgtc gtcccaaacc tcgtctaact atactgtcat   360
tgctggcgga gcttcgggaa gtggcactac cactcgatac tgggattgct gcaaggcttc   420
ctgtagctgg cccggtaagg catctgtgac ctccccggtt gcctcctgcg ccaaggatgg   480
cgtcactctt gtcgatagcg acactcaggt acgtatgtca aaagaacaag cttacatgtg   540
caacgacaac caaccttggg ccgtttcgga tgatcttgcc tacggttttg ctgctgcctc   600
gatcagcggc ggaagtgaat cgacctggtg ttgcgcgtgt tatgagctta cctttacctc   660
cactgctatt gctggcaaga agatggttgt tcaagtaacc aacactggtg gtgacctggg   720
atcaaa                                                              726
```

<210> SEQ ID NO 26
<211> LENGTH: 241
<212> TYPE: PRT
<213> ORGANISM: Thermomucor indicae-seudaticae
<220> FEATURE:
<221> NAME/KEY: misc_feature
<222> LOCATION: (13)..(15)
<223> OTHER INFORMATION: Xaa can be any naturally occurring amino acid

<400> SEQUENCE: 26

```
Met Lys Asn Thr Gly Phe Val Lys Cys Val Ile Val Xaa Xaa Xaa Gly
 1               5                  10                  15

Lys Asp Tyr Thr Gly Ala Thr Cys Cys Val Ser Gly Tyr Glu Cys Leu
            20                  25                  30

Lys Ala Asp Val Trp Tyr Ser Gln Cys Leu Pro Lys Tyr Gln Gly Ser
        35                  40                  45

Ser Ala Ser Ser Val Asn Pro Ser Val Thr Ala Val Ser Thr Val
    50                  55                  60

Pro Thr Thr Ser Ser Pro Ala Ser Lys Thr Ala Ile Asn Met Lys Thr
65                  70                  75                  80

Thr Thr Thr Thr Thr Thr Thr Ala Ser Ala Lys Pro Thr Thr Arg
                85                  90                  95

Ser Ala Thr Ser Tyr Ala Ser Lys Thr Ile Thr Ser Ser Ser Ser Gln
            100                 105                 110

Thr Ser Ser Asn Tyr Thr Val Ile Ala Gly Gly Ala Ser Gly Ser Gly
        115                 120                 125

Thr Thr Thr Arg Tyr Trp Asp Cys Cys Lys Ala Ser Cys Ser Trp Pro
    130                 135                 140

Gly Lys Ala Ser Val Thr Ser Pro Val Ala Ser Cys Ala Lys Asp Gly
145                 150                 155                 160

Val Thr Leu Val Asp Ser Asp Thr Gln Val Arg Met Ser Lys Glu Gln
                165                 170                 175

Ala Tyr Met Cys Asn Asp Asn Gln Pro Trp Ala Val Ser Asp Asp Leu
            180                 185                 190

Ala Tyr Gly Phe Ala Ala Ala Ser Ile Ser Gly Gly Ser Glu Ser Thr
        195                 200                 205
```

```
Trp Cys Cys Ala Cys Tyr Glu Leu Thr Phe Thr Ser Thr Ala Ile Ala
    210                 215                 220

Gly Lys Lys Met Val Val Gln Val Thr Asn Thr Gly Gly Asp Leu Gly
225                 230                 235                 240

Ser

<210> SEQ ID NO 27
<211> LENGTH: 543
<212> TYPE: DNA
<213> ORGANISM: Malbranchea cinnamomea

<400> SEQUENCE: 27
tgtatctgcg cctggcctga aaaaggcccc gtcactgcac cagtaaccac ctgcgacata     60
aatgactctc ttctctcaga cccattggcg gtatctggct gtgaggagag cggatccgca    120
ttcatgtgtt cgagtcaatc gccatgggcc gttgacgaaa aacttgcgta cggattccca    180
cctgtcagga ttgctggcca aaccgaatcg gactggggtt gcgcctgcta tgagttgact    240
ttcaccagcg ggcctgcaca ggggaaaaag tggttggttc aggcgacaaa tacgggcggt    300
gatcttggaa gcaatcattt cgatatcgct atacctggcg gtggcgttgg cattttcaac    360
ggctgcaccc caaccggaac acgcccccca gatggctggg gtgaccgata tggcgggatc    420
cgggagaata cctgctatga gcttcctgca cctctccagc cgggatgcga atggcgcttc    480
gactggttcc aaaactcgga caaccaaact gtcgacttcg atccaagtgg aatgccctgc    540
tga                                                                  543

<210> SEQ ID NO 28
<211> LENGTH: 180
<212> TYPE: PRT
<213> ORGANISM: Malbranchea cinnamomea

<400> SEQUENCE: 28

Cys Ile Cys Ala Trp Pro Glu Lys Gly Pro Val Thr Ala Pro Val Thr
1               5                   10                  15

Thr Cys Asp Ile Asn Asp Ser Leu Leu Ser Asp Pro Leu Ala Val Ser
            20                  25                  30

Gly Cys Glu Glu Ser Gly Ser Ala Phe Met Cys Ser Ser Gln Ser Pro
        35                  40                  45

Trp Ala Val Asp Glu Lys Leu Ala Tyr Gly Phe Pro Pro Val Arg Ile
    50                  55                  60

Ala Gly Gln Thr Glu Ser Asp Trp Gly Cys Ala Cys Tyr Glu Leu Thr
65                  70                  75                  80

Phe Thr Ser Gly Pro Ala Gln Gly Lys Lys Trp Leu Val Gln Ala Thr
                85                  90                  95

Asn Thr Gly Gly Asp Leu Gly Ser Asn His Phe Asp Ile Ala Ile Pro
            100                 105                 110

Gly Gly Gly Val Gly Ile Phe Asn Gly Cys Thr Pro Thr Gly Thr Arg
        115                 120                 125

Pro Pro Asp Gly Trp Gly Asp Arg Tyr Gly Ile Arg Glu Asn Thr
    130                 135                 140

Cys Tyr Glu Leu Pro Ala Pro Leu Gln Pro Gly Cys Glu Trp Arg Phe
145                 150                 155                 160

Asp Trp Phe Gln Asn Ser Asp Asn Gln Thr Val Asp Phe Asp Pro Ser
                165                 170                 175

Gly Met Pro Cys
            180
```

<210> SEQ ID NO 29
<211> LENGTH: 153
<212> TYPE: DNA
<213> ORGANISM: Rhizomucor miehei

<400> SEQUENCE: 29
gtcgacggta gcagtgtatc ttctccagtc ggcacttgcg ccaaggacgg cgttactctc    60
attgatgcca acacacaggc aagttttcag agaaacaaat ttactatctc atttctggag   120
tggtcactaa aagaagaaaa ccttttcttt atg                                153

<210> SEQ ID NO 30
<211> LENGTH: 51
<212> TYPE: PRT
<213> ORGANISM: Rhizomucor miehei

<400> SEQUENCE: 30

Val Asp Gly Ser Ser Val Ser Ser Pro Val Gly Thr Cys Ala Lys Asp
1               5                   10                  15

Gly Val Thr Leu Ile Asp Ala Asn Thr Gln Ala Ser Phe Gln Arg Asn
            20                  25                  30

Lys Phe Thr Ile Ser Phe Leu Glu Trp Ser Leu Lys Glu Glu Asn Leu
        35                  40                  45

Phe Phe Met
        50

<210> SEQ ID NO 31
<211> LENGTH: 189
<212> TYPE: DNA
<213> ORGANISM: Thermoascus aurantiacus

<400> SEQUENCE: 31
gaccagcccg tctactcgtg cgacgccaac ttccagcgca tccacgactt cgatgccgtc    60
tcgggctgcg agggcggccc cgccttctcg tgcgccgacc acagccctg gccattaat    120 gacaacctct cgtacggctt cgcggcgact gcactcagcg ccagaccga ggagtcgtgg   180 tgctgcgct                                                           189

<210> SEQ ID NO 32
<211> LENGTH: 63
<212> TYPE: PRT
<213> ORGANISM: Thermoascus aurantiacus

<400> SEQUENCE: 32

Asp Gln Pro Val Tyr Ser Cys Asp Ala Asn Phe Gln Arg Ile His Asp
1               5                   10                  15

Phe Asp Ala Val Ser Gly Cys Glu Gly Gly Pro Ala Phe Ser Cys Ala
            20                  25                  30

Asp His Ser Pro Trp Ala Ile Asn Asp Asn Leu Ser Tyr Gly Phe Ala
        35                  40                  45

Ala Thr Ala Leu Ser Gly Gln Thr Glu Glu Ser Trp Cys Cys Ala
    50                  55                  60

<210> SEQ ID NO 33
<211> LENGTH: 573
<212> TYPE: DNA
<213> ORGANISM: Chaetomium senegalense

<400> SEQUENCE: 33

```
tctcgtaacc agcccgtcta tgcttgtgac gccaacttcc agcgtatcag cgaccccggg      60
actaagtctg gctgcgacgg cggttcagct tattcgtgcg ccgatcacag cccgtgggcg     120
gtgaatgaca gcttctccta cggattcgcg gctaccgctc tgtcaggagg cacggaagcc     180
tcttggtgct gcgcgtgcta tgcgctcacc ttcacttccg gccccgtagc gggaaagacc     240
atggtggtac aatccaccag taccggcggc gacctcggca gcaaccactt cgatctcaac     300
atacccggcg gcggcgtggg cctcttcgac ggctgcacgc ctcagttcgg cggtctgccg     360
ggcgcccgat acggaggcat ctcgtcgcgc agccagtgcg actcgttccc cgggccgctc     420
aaggccggct gctactgggg cttctactgg ttcaagaacg ccgaccaccc gaacttcacc     480
ttccagcagg tccggtgccc gaacgagctg gtggaacgga ccggatgccc ccgcgcctac     540
gaaggcccct ttcccgactt caccctccca tag                                  573
```

<210> SEQ ID NO 34
<211> LENGTH: 190
<212> TYPE: PRT
<213> ORGANISM: Chaetomium senegalense

<400> SEQUENCE: 34

```
Ser Arg Asn Gln Pro Val Tyr Ala Cys Asp Ala Asn Phe Gln Arg Ile
1               5                   10                  15

Ser Asp Pro Gly Thr Lys Ser Gly Cys Asp Gly Gly Ser Ala Tyr Ser
            20                  25                  30

Cys Ala Asp His Ser Pro Trp Ala Val Asn Asp Ser Phe Ser Tyr Gly
        35                  40                  45

Phe Ala Ala Thr Ala Leu Ser Gly Gly Thr Glu Ala Ser Trp Cys Cys
    50                  55                  60

Ala Cys Tyr Ala Leu Thr Phe Thr Ser Gly Pro Val Ala Gly Lys Thr
65                  70                  75                  80

Met Val Val Gln Ser Thr Ser Thr Gly Gly Asp Leu Gly Ser Asn His
                85                  90                  95

Phe Asp Leu Asn Ile Pro Gly Gly Gly Val Gly Leu Phe Asp Gly Cys
            100                 105                 110

Thr Pro Gln Phe Gly Gly Leu Pro Gly Ala Arg Tyr Gly Gly Ile Ser
        115                 120                 125

Ser Arg Ser Gln Cys Asp Ser Phe Pro Gly Pro Leu Lys Ala Gly Cys
    130                 135                 140

Tyr Trp Gly Phe Tyr Trp Phe Lys Asn Ala Asp His Pro Asn Phe Thr
145                 150                 155                 160

Phe Gln Gln Val Arg Cys Pro Asn Glu Leu Val Glu Arg Thr Gly Cys
                165                 170                 175

Pro Arg Ala Tyr Glu Gly Pro Phe Pro Asp Phe Thr Leu Pro
            180                 185                 190
```

<210> SEQ ID NO 35
<211> LENGTH: 783
<212> TYPE: DNA
<213> ORGANISM: Remersonia thermophila

<400> SEQUENCE: 35

```
ctccgtcacc agcccgtcta cgcctgcaac gccagttcc agcgcatcag cgaccccatg       60
gccaagtctg gctgcgatgg tggccccgcc tactcgtgcg ccgaccatac cccgtgggcc     120
gtgaacgacg agttctcgta cggctttgcc gccacttcga ttgccggcgg ctctgagtcg     180
```

```
tcgtggtgct gcgcctgcta cgagctcacc ttcacctcgg gtcctgtggc cggcaagaag      240
atggtcgtcc agtcgaccag caccggcggc gatcttggca gcaaccactt cgacctcaac      300
atccccggtg gcggtgttgg cctcttcgac ggctgcacgc ctcagtttgg cggcttgccc      360
ggtcagcgct acggcggcat ctcgtcccgc gccgagtgcg agaggttccc ggaggctctc      420
aagcccggct gctactggcg cttcgactgg ttcaagaacg ccgacaaccc gagctttagc      480
ttccgccagg tccagtgccc ggcggagctg gtcgcccgta ccggctgccg ccgcaacgac      540
gacggcaact ccccgtcgt ttctcctccc tcgagccagc ccagcaccac cagcacgtcc       600
tcctcctcct cctcctccac cacttcctcc tccatccagc agccgaccca gcccacctcg      660
cctggaggct gcgtttccca gaagtggggg cagtgcggcg gtaacggctg gagcggctgc      720
acctcttgcg aggctggctc gacctgcacg aaggtgaatg agtggtactc ccagtgcatg      780
tag                                                                    783
```

<210> SEQ ID NO 36
<211> LENGTH: 260
<212> TYPE: PRT
<213> ORGANISM: Remersonia thermophila

<400> SEQUENCE: 36

```
Leu Arg His Gln Pro Val Tyr Ala Cys Asn Ala Gln Phe Gln Arg Ile
1               5                   10                  15

Ser Asp Pro Met Ala Lys Ser Gly Cys Asp Gly Gly Pro Ala Tyr Ser
            20                  25                  30

Cys Ala Asp His Thr Pro Trp Ala Val Asn Asp Glu Phe Ser Tyr Gly
        35                  40                  45

Phe Ala Ala Thr Ser Ile Ala Gly Gly Ser Glu Ser Ser Trp Cys Cys
    50                  55                  60

Ala Cys Tyr Glu Leu Thr Phe Thr Ser Gly Pro Val Ala Gly Lys Lys
65                  70                  75                  80

Met Val Val Gln Ser Thr Ser Thr Gly Gly Asp Leu Gly Ser Asn His
                85                  90                  95

Phe Asp Leu Asn Ile Pro Gly Gly Gly Val Gly Leu Phe Asp Gly Cys
            100                 105                 110

Thr Pro Gln Phe Gly Gly Leu Pro Gly Gln Arg Tyr Gly Gly Ile Ser
        115                 120                 125

Ser Arg Ala Glu Cys Glu Arg Phe Pro Glu Ala Leu Lys Pro Gly Cys
    130                 135                 140

Tyr Trp Arg Phe Asp Trp Phe Lys Asn Ala Asp Asn Pro Ser Phe Ser
145                 150                 155                 160

Phe Arg Gln Val Gln Cys Pro Ala Glu Leu Val Ala Arg Thr Gly Cys
                165                 170                 175

Arg Arg Asn Asp Asp Gly Asn Phe Pro Val Val Ser Pro Ser Ser
            180                 185                 190

Gln Pro Ser Thr Thr Ser Thr Ser Ser Ser Ser Ser Thr Thr
        195                 200                 205

Ser Ser Ser Ile Gln Gln Pro Thr Gln Pro Thr Ser Pro Gly Gly Cys
    210                 215                 220

Val Ser Gln Lys Trp Gly Gln Cys Gly Gly Asn Gly Trp Ser Gly Cys
225                 230                 235                 240

Thr Ser Cys Glu Ala Gly Ser Thr Cys Thr Lys Val Asn Glu Trp Tyr
                245                 250                 255

Ser Gln Cys Met
```

<210> SEQ ID NO 37
<211> LENGTH: 162
<212> TYPE: DNA
<213> ORGANISM: Rhizomucor miehei

<400> SEQUENCE: 37

```
cacttccagc gtatctgcga ccccgatgct aagtctggct gcgacggcgg ctcagcttac      60
tcttgcgccg accacagccc gtgggccgtg aatgacaact tctcctacgg attcgctgct     120
accaccattg ccggaggcac tgatgcttct tggtgctgcg cc                        162
```

<210> SEQ ID NO 38
<211> LENGTH: 54
<212> TYPE: PRT
<213> ORGANISM: Rhizomucor miehei

<400> SEQUENCE: 38

```
His Phe Gln Arg Ile Cys Asp Pro Asp Ala Lys Ser Gly Cys Asp Gly
 1               5                  10                  15
Gly Ser Ala Tyr Ser Cys Ala Asp His Ser Pro Trp Ala Val Asn Asp
            20                  25                  30
Asn Phe Ser Tyr Gly Phe Ala Ala Thr Thr Ile Ala Gly Gly Thr Asp
        35                  40                  45
Ala Ser Trp Cys Cys Ala
    50
```

<210> SEQ ID NO 39
<211> LENGTH: 318
<212> TYPE: DNA
<213> ORGANISM: Remersonia thermophila

<400> SEQUENCE: 39

```
gccgatgaag tcaaggccat cctccagaag gccggttcca acgcccgcgt ccgcggcttc      60
gcgtccaacg tgtccaacta caaccCctac caggacagca accCgccgtc gtacaccaac     120
ggctcgccct cggccgacga gtcccgctac gccaactcgc tcggcgaggc gctgcgccag     180
cgcggcctgc cctcgcagtt catcatcgac cagggccgcg tcgcccttcc cggcgcccgc     240
cgcgagtggg gcgagtggtg caacgtgtcg cccgccggct tcggccagcc cttcacgacc     300
aacaccaaca accccaac                                                    318
```

<210> SEQ ID NO 40
<211> LENGTH: 106
<212> TYPE: PRT
<213> ORGANISM: Remersonia thermophila

<400> SEQUENCE: 40

```
Ala Asp Glu Val Lys Ala Ile Leu Gln Lys Ala Gly Ser Asn Ala Arg
 1               5                  10                  15
Val Arg Gly Phe Ala Ser Asn Val Ser Asn Tyr Asn Pro Tyr Gln Asp
            20                  25                  30
Ser Asn Pro Pro Ser Tyr Thr Asn Gly Ser Pro Ser Ala Asp Glu Ser
        35                  40                  45
Arg Tyr Ala Asn Ser Leu Gly Glu Ala Leu Arg Gln Arg Gly Leu Pro
    50                  55                  60
Ser Gln Phe Ile Ile Asp Gln Gly Arg Val Ala Leu Pro Gly Ala Arg
65                  70                  75                  80
```

```
Arg Glu Trp Gly Glu Trp Cys Asn Val Ser Pro Ala Gly Phe Gly Gln
                85                  90                  95

Pro Phe Thr Thr Asn Thr Asn Asn Pro Asn
            100                 105

<210> SEQ ID NO 41
<211> LENGTH: 204
<212> TYPE: DNA
<213> ORGANISM: Corynascus thermophilus

<400> SEQUENCE: 41
gggacgtcga cgccggtgca gacgtgcgac cgcaacgaca acccgctcta cgacggcggg      60
tcgacgcggt ccggctgcga cgccggcggc ggcgcctaca tgtgctcgtc gcacagcccg     120
tgggccgtca cgacagcct ctcgtacggc tgggcggccg tccgcatcgc cggccagtcc      180
gagcagcagt ggtgttgcgc ctgc                                            204

<210> SEQ ID NO 42
<211> LENGTH: 68
<212> TYPE: PRT
<213> ORGANISM: Corynascus thermophilus

<400> SEQUENCE: 42

Gly Thr Ser Thr Pro Val Gln Thr Cys Asp Arg Asn Asp Asn Pro Leu
1               5                   10                  15

Tyr Asp Gly Gly Ser Thr Arg Ser Gly Cys Asp Ala Gly Gly Gly Ala
            20                  25                  30

Tyr Met Cys Ser Ser His Ser Pro Trp Ala Val Ser Asp Ser Leu Ser
        35                  40                  45

Tyr Gly Trp Ala Ala Val Arg Ile Ala Gly Gln Ser Glu Gln Gln Trp
    50                  55                  60

Cys Cys Ala Cys
65

<210> SEQ ID NO 43
<211> LENGTH: 411
<212> TYPE: DNA
<213> ORGANISM: Chaetomium thermophilum

<400> SEQUENCE: 43
ccttggctct ccagcggtga atatcatcaa tctctcctca ttcacgtctg tagaagtctg      60
agcacacacc agacaagctt caaaatgcgt tcgacccctg ttctccgtac cgcccttgtg     120
gctgccctcc cctttactgt cctggctgcc gacggcaagt ccaccaggta ctgggattgc     180
tgcaagccat cctgctcgtg gcccggcaag gctgccgtga ccagcccgt cttcgcctgc      240 gatcgcaact tcaaccgcat ctatgacttc aatgctaagt ctggctgcga cggcggctcg     300
gcttactctt gcgccgacca gactccgtgg gccgtcaacg accagttctc gtacggcttc     360
gctgccacca acattgccgg gggtaatgag gcttcgtggt gttgcgcctg c              411

<210> SEQ ID NO 44
<211> LENGTH: 109
<212> TYPE: PRT
<213> ORGANISM: Chaetomium thermophilum

<400> SEQUENCE: 44

Met Arg Ser Thr Pro Val Leu Arg Thr Ala Leu Val Ala Ala Leu Pro
1               5                   10                  15

Phe Thr Val Leu Ala Ala Asp Gly Lys Ser Thr Arg Tyr Trp Asp Cys
```

```
                 20                  25                  30

Cys Lys Pro Ser Cys Ser Trp Pro Gly Lys Ala Ala Val Ser Gln Pro
             35                  40                  45

Val Phe Ala Cys Asp Arg Asn Phe Asn Arg Ile Tyr Asp Phe Asn Ala
         50                  55                  60

Lys Ser Gly Cys Asp Gly Ser Ala Tyr Ser Cys Ala Asp Gln Thr
 65                  70                  75                  80

Pro Trp Ala Val Asn Asp Gln Phe Ser Tyr Gly Phe Ala Ala Thr Asn
                 85                  90                  95

Ile Ala Gly Gly Asn Glu Ala Ser Trp Cys Cys Ala Cys
                100                 105

<210> SEQ ID NO 45
<211> LENGTH: 834
<212> TYPE: DNA
<213> ORGANISM: Scytalidium indonesiacum

<400> SEQUENCE: 45
atgcgctcct ctcccctcct ccgctccgcc gttgtggccg ccctgccagt gttggccctt      60
gccgctgatg gcaagtccac ccgctactgg gactgctgca agccttcgtg cggttgggcc     120
aaaaaggctc ccgtgaacca acccgtcttt tcctgcaatg ccaacttcca gcgtctctat     180
gactttgacg ccaagtccgg ctgcgagccg ggcggtgtcg cctactcttg cgccgaccag     240
accccatggg ctgtgaacga cgacttcgcg ttcggttttg ctgccacctc tattgccggc     300
agcaatgagg cgggctggtg ctgcgcctgc tacgagctca ccttcacatc cggccctgtt     360
gctggcaaga gatggtcgt ccagtccacc agcactggcg gtgatcttgg cagcaaccac     420
ttcgacctca acatcccggg cggcggcgtc ggcatcttcg acggctgcac tccccagttc     480
ggcggcctgc ccggccagcg ctacgccggc atctcgtccc gcaacgagtg cgagaggttc     540
cccgacgccc tgaagcctgg ctgctactgg cgcttcgact ggttcaagaa tgccgacaac     600
ccgaacttca gcttccgtca ggtccagtgc ccggccgagc tcgtcgcccg caccggatgc     660
cgccgcaacg acgacggcaa cttccctgcc gtccagatcc cctccagcag caccagctcg     720
ccccgtatac agaacctcgg ctccacgaga atgttgtcga gatcgagacg acgacgaccg     780
gccggcgggt ctcaactcgc agcggctggg ggggtgagag gggggctcc atag            834

<210> SEQ ID NO 46
<211> LENGTH: 277
<212> TYPE: PRT
<213> ORGANISM: Scytalidium indonesiacum

<400> SEQUENCE: 46

Met Arg Ser Ser Pro Leu Leu Arg Ser Ala Val Val Ala Ala Leu Pro
  1               5                  10                  15

Val Leu Ala Leu Ala Ala Asp Gly Lys Ser Thr Arg Tyr Trp Asp Cys
             20                  25                  30

Cys Lys Pro Ser Cys Gly Trp Ala Lys Lys Ala Pro Val Asn Gln Pro
             35                  40                  45

Val Phe Ser Cys Asn Ala Asn Phe Gln Arg Leu Tyr Asp Phe Asp Ala
         50                  55                  60

Lys Ser Gly Cys Glu Pro Gly Gly Val Ala Tyr Ser Cys Ala Asp Gln
 65                  70                  75                  80

Thr Pro Trp Ala Val Asn Asp Asp Phe Ala Phe Gly Phe Ala Ala Thr
                 85                  90                  95
```

```
Ser Ile Ala Gly Ser Asn Glu Ala Gly Trp Cys Cys Ala Cys Tyr Glu
                100                 105                 110
Leu Thr Phe Thr Ser Gly Pro Val Ala Gly Lys Lys Met Val Val Gln
            115                 120                 125
Ser Thr Ser Thr Gly Gly Asp Leu Gly Ser Asn His Phe Asp Leu Asn
        130                 135                 140
Ile Pro Gly Gly Val Gly Ile Phe Asp Gly Cys Thr Pro Gln Phe
145                 150                 155                 160
Gly Gly Leu Pro Gly Gln Arg Tyr Gly Ile Ser Ser Arg Asn Glu
                165                 170                 175
Cys Glu Arg Phe Pro Asp Ala Leu Lys Pro Gly Cys Tyr Trp Arg Phe
            180                 185                 190
Asp Trp Phe Lys Asn Ala Asp Asn Pro Asn Phe Ser Phe Arg Gln Val
        195                 200                 205
Gln Cys Pro Ala Glu Leu Val Ala Arg Thr Gly Cys Arg Arg Asn Asp
    210                 215                 220
Asp Gly Asn Phe Pro Ala Val Gln Ile Pro Ser Ser Thr Ser Ser
225                 230                 235                 240
Pro Arg Ile Gln Asn Leu Gly Ser Thr Arg Met Leu Ser Arg Ser Arg
                245                 250                 255
Arg Arg Arg Pro Ala Gly Gly Ser Gln Leu Ala Ala Ala Gly Gly Val
            260                 265                 270
Arg Gly Gly Ala Pro
        275

<210> SEQ ID NO 47
<211> LENGTH: 1005
<212> TYPE: DNA
<213> ORGANISM: Malbranchea cinnamomea

<400> SEQUENCE: 47
atgtcaccct ccttcaagtc cactgccatc ctcggagccg ttgctctggc cgcccgcgtg      60
cgcgcccacg gctacgtgtc tggaatcgtc gttgacggtg cttaccatgg cggttacatc     120
gtcgacaagt accgctacat gcccaaccca cccgatgtgg tcggctggtc gactacggcc     180
acggacctgg gcttcgtcgc ccctgacgcc tttggcgacc cggacatcat ctgccaccgg     240
gacggtgccc ccggtgccat ccacgccaaa gtcaacgccg tgccaccat cgagctgcag      300
tggaacacct ggcccgaaag ccaccacggg cccgtcatcg actacctggc taactgcaac     360
ggtgactgct cgtccgtcga caagacctcg ctcaagttct tcaagatcag cgaggccggc     420
ctaaacgacg gctccaacgc ccccggccag tgggcgtccg acgatctcat tgccaacaac     480
aacagctgga ctgtgaccat ccccaagtcg atcgccccgg gcaactacgt gctgcgccac     540
gagatcatcg ccctgcacag cgccggcaac cagaatggcg cgcagaacta cccccagtgc     600
ttcaacctcg agatcaccag caacggcagc gacaacccgg agggcgtgct gggaaccgag     660
ctgtacaagg ccgacgaccc gggcattctg ttcaacatct accagcccat ggactcgtac     720
ccgattcccg ccctgctct ctacaccggc ggctcttctc cctcccctaa tccgcccacc      780
tctacccagt cgcctgtgcc ccagcccacc cagtctcccc catcgggcag caaccccggc     840
aacggcaacg gcgacgacga caacgacaac ggcaacgaga ccccatcccc gtctctcccc     900
gtcgagatcc ctgacgacct gacctcgcgc gagctactcc ttgtggccca ggagatcatt     960
gcccgtctgc ttgagctgca gaatcagctg gtcgtctcga actaa                    1005
```

```
<210> SEQ ID NO 48
<211> LENGTH: 334
<212> TYPE: PRT
<213> ORGANISM: Malbranchea cinnamomea

<400> SEQUENCE: 48
```

Met Ser Pro Ser Phe Lys Ser Thr Ala Ile Leu Gly Ala Val Ala Leu
1               5                   10                  15

Ala Ala Arg Val Arg Ala His Gly Tyr Val Ser Gly Ile Val Val Asp
            20                  25                  30

Gly Ala Tyr His Gly Gly Tyr Ile Val Asp Lys Tyr Pro Tyr Met Pro
        35                  40                  45

Asn Pro Pro Asp Val Val Gly Trp Ser Thr Thr Ala Thr Asp Leu Gly
    50                  55                  60

Phe Val Ala Pro Asp Ala Phe Gly Asp Pro Asp Ile Ile Cys His Arg
65                  70                  75                  80

Asp Gly Ala Pro Gly Ala Ile His Ala Lys Val Asn Ala Gly Ala Thr
                85                  90                  95

Ile Glu Leu Gln Trp Asn Thr Trp Pro Glu Ser His His Gly Pro Val
            100                 105                 110

Ile Asp Tyr Leu Ala Asn Cys Asn Gly Asp Cys Ser Ser Val Asp Lys
        115                 120                 125

Thr Ser Leu Lys Phe Phe Lys Ile Ser Glu Ala Gly Leu Asn Asp Gly
130                 135                 140

Ser Asn Ala Pro Gly Gln Trp Ala Ser Asp Asp Leu Ile Ala Asn Asn
145                 150                 155                 160

Asn Ser Trp Thr Val Thr Ile Pro Lys Ser Ile Ala Pro Gly Asn Tyr
                165                 170                 175

Val Leu Arg His Glu Ile Ile Ala Leu His Ser Ala Gly Asn Gln Asn
            180                 185                 190

Gly Ala Gln Asn Tyr Pro Gln Cys Phe Asn Leu Glu Ile Thr Ser Asn
        195                 200                 205

Gly Ser Asp Asn Pro Glu Gly Val Leu Gly Thr Glu Leu Tyr Lys Ala
210                 215                 220

Asp Asp Pro Gly Ile Leu Phe Asn Ile Tyr Gln Pro Met Asp Ser Tyr
225                 230                 235                 240

Pro Ile Pro Gly Pro Ala Leu Tyr Thr Gly Gly Ser Ser Pro Ser Pro
                245                 250                 255

Asn Pro Pro Thr Ser Thr Gln Ser Pro Val Pro Gln Pro Thr Gln Ser
            260                 265                 270

Pro Pro Ser Gly Ser Asn Pro Gly Asn Gly Asn Gly Asp Asp Asn
        275                 280                 285

Asp Asn Gly Asn Glu Thr Pro Ser Pro Ser Leu Pro Val Glu Ile Pro
290                 295                 300

Asp Asp Leu Thr Ser Arg Glu Leu Leu Leu Val Ala Gln Glu Ile Ile
305                 310                 315                 320

Ala Arg Leu Leu Glu Leu Gln Asn Gln Leu Val Val Ser Asn
                325                 330

```
<210> SEQ ID NO 49
<211> LENGTH: 1091
<212> TYPE: DNA
<213> ORGANISM: Chaetomium thermophilum
<220> FEATURE:
<221> NAME/KEY: misc_feature
<222> LOCATION: (522)..(524)
<223> OTHER INFORMATION: n is a, c, g, or t
```

<400> SEQUENCE: 49

```
atgccttcct tcgcttcgaa gactctcatt tctgccctcg ccggcgctgc cagcgtcgcc        60
gctcacggcc acgtcaagaa cttcgtcatc aacggtctgt cgtaccaggc ctacgacccg       120
accgtcttcc cgtacatgca gaaccctccc atcgtcgccg gctggacggc ctccaacact       180
gacaacggct tcgtgggccc cgagtcctac tcgagccccg atatcatctg ccacaagtcg       240
gccacgaacg ccaagggcca tgccgtcatc aaggccggtg actctgtcta catccagtgg       300
gacacctggc ccgagtcgca ccacggcccg gtcatcgact acctcgccag ctgcggcagc       360
gccggctgcg agacggtcga caagacccag ctcgagttct tcaagatcgc cgaggccggt       420
ctgattgacg gctcccaggc tcccggaaag tgggctgccg atcagctcat cgcccagaac       480
aactcgtggc tggtcaccat ccccgagaat atcaagccgc tnnnggctcc tacgtcctcc       540
gccacgagat catcgccctg cacagcgctg ccagaccaa cggtgcccag aactaccccg        600
tctgcatcaa cctcgaggtc actggtggcg gcagcgacgt tccctcgggt gtcaagggta       660
ctgagctcta caagcccacc gaccccggca tcctcatcaa catctaccag tcgctctcga       720
actacaccat ccctggccct gctctgatgc ccggcgccaa gccagtcacc cagcacacct       780
cagccatcat cggcagcacc accgccatca ctggcaccgc caccgctgct ccggccgcgc       840
cgacctcgac cgccgctgcc atcaccacca gctctgctaa tgccaacccc gccccgacca       900
ccacccgcgg caacgccaac cccgtcccga ctaccaccct ccgcacgagc accatcgctc       960
ctcagcccac tgctgccccc atccagaccc cgacctccag cgtcggccgg ccccgcgcc      1020
cgacccgctg ccctggtctg acaacttca agcgcgctcg tcgccacgct cgtgaccttg      1080
ctgcccacta a                                                          1091
```

<210> SEQ ID NO 50
<211> LENGTH: 364
<212> TYPE: PRT
<213> ORGANISM: Chaetomium thermophilum
<220> FEATURE:
<221> NAME/KEY: misc_feature
<222> LOCATION: (174)..(176)
<223> OTHER INFORMATION: Xaa can be any naturally occurring amino acid

<400> SEQUENCE: 50

```
Met Pro Ser Phe Ala Ser Lys Thr Leu Ile Ser Ala Leu Ala Gly Ala
1               5                   10                  15

Ala Ser Val Ala Ala His Gly His Val Lys Asn Phe Val Ile Asn Gly
            20                  25                  30

Leu Ser Tyr Gln Ala Tyr Asp Pro Thr Val Phe Pro Tyr Met Gln Asn
        35                  40                  45

Pro Pro Ile Val Ala Gly Trp Thr Ala Ser Asn Thr Asp Asn Gly Phe
    50                  55                  60

Val Gly Pro Glu Ser Tyr Ser Ser Pro Asp Ile Ile Cys His Lys Ser
65                  70                  75                  80

Ala Thr Asn Ala Lys Gly His Ala Val Ile Lys Ala Gly Asp Ser Val
                85                  90                  95

Tyr Ile Gln Trp Asp Thr Trp Pro Glu Ser His Gly Pro Val Ile
            100                 105                 110

Asp Tyr Leu Ala Ser Cys Gly Ser Ala Gly Cys Glu Thr Val Asp Lys
        115                 120                 125

Thr Gln Leu Glu Phe Phe Lys Ile Ala Glu Ala Gly Leu Ile Asp Gly
    130                 135                 140
```

Ser Gln Ala Pro Gly Lys Trp Ala Ala Asp Gln Leu Ile Ala Gln Asn
145                 150                 155                 160

Asn Ser Trp Leu Val Thr Ile Pro Glu Asn Ile Lys Pro Xaa Xaa Xaa
                165                 170                 175

Gly Ser Tyr Val Leu Arg His Glu Ile Ile Ala Leu His Ser Ala Gly
            180                 185                 190

Gln Thr Asn Gly Ala Gln Asn Tyr Pro Val Cys Ile Asn Leu Glu Val
        195                 200                 205

Thr Gly Gly Gly Ser Asp Val Pro Ser Gly Val Lys Gly Thr Glu Leu
    210                 215                 220

Tyr Lys Pro Thr Asp Pro Gly Ile Leu Ile Asn Ile Tyr Gln Ser Leu
225                 230                 235                 240

Ser Asn Tyr Thr Ile Pro Gly Pro Ala Leu Met Pro Gly Ala Lys Pro
                245                 250                 255

Val Thr Gln His Thr Ser Ala Ile Ile Gly Ser Thr Thr Ala Ile Thr
            260                 265                 270

Gly Thr Ala Thr Ala Ala Pro Ala Ala Pro Thr Ser Thr Ala Ala Ala
        275                 280                 285

Ile Thr Thr Ser Ser Ala Asn Ala Asn Pro Ala Pro Thr Thr Thr Arg
    290                 295                 300

Gly Asn Ala Asn Pro Val Pro Thr Thr Thr Leu Arg Thr Ser Thr Ile
305                 310                 315                 320

Ala Pro Gln Pro Thr Ala Ala Pro Ile Gln Thr Pro Thr Ser Ser Val
                325                 330                 335

Gly Arg Pro Pro Arg Pro Thr Arg Cys Pro Gly Leu Asp Asn Phe Lys
            340                 345                 350

Arg Ala Arg Arg His Ala Arg Asp Leu Ala Ala His
        355                 360

<210> SEQ ID NO 51
<211> LENGTH: 315
<212> TYPE: DNA
<213> ORGANISM: Remersonia thermophila

<400> SEQUENCE: 51
gacattattt gtcaacagtc ggccaccaac gccggcgggt acgccgtggt ggcggccggc      60
gacaaggtct acatccagtg ggaccagtgg cccgagagcc accacggccc cgtcatcgac     120
tacctcgcca gctgcggcag cacgggctgc gacgccgtca acaaggccga cctcgagttg     180
ttcaagatcg gcgaggtcgg cctgatcgac ggccgccagg ccccggcttc ctggggctcc     240
gaccagctca tcgccaacaa cgccggctgg ctcgtccaga tcccctccga cctcgcgtcg     300
atcatctctc gagct                                                     315

<210> SEQ ID NO 52
<211> LENGTH: 99
<212> TYPE: PRT
<213> ORGANISM: Remersonia thermophila

<400> SEQUENCE: 52

Asp Ile Ile Cys Gln Gln Ser Thr Asn Ala Gly Gly Tyr Ala Val
1               5                   10                  15

Val Ala Ala Gly Asp Lys Val Tyr Ile Gln Trp Asp Gln Trp Pro Glu
            20                  25                  30

Ser His His Gly Pro Val Ile Asp Tyr Leu Ala Ser Cys Gly Ser Thr
        35                  40                  45

```
Gly Cys Asp Ala Val Asn Lys Ala Asp Leu Glu Leu Phe Lys Ile Gly
            50                  55                  60

Glu Val Gly Leu Ile Asp Gly Arg Gln Ala Pro Gly Phe Trp Gly Ser
 65                  70                  75                  80

Asp Gln Leu Ile Ala Asn Asn Ala Gly Trp Leu Val Gln Ile Pro Ser
                85                  90                  95

Asp Leu Ala

<210> SEQ ID NO 53
<211> LENGTH: 339
<212> TYPE: DNA
<213> ORGANISM: Chaetomium senegalense

<400> SEQUENCE: 53
ctggagtttt tcaagatcga cgaggtcggc ctggtcgacg gcgccaacgc gcccggtttc      60
tggggctcgg accagctgat cgccaacaac gccgcgtgga tggtccagat ccccgaggac     120
atcgctcccg gcttctacgt ggtccgccac gagatcatcg ccctccacag cgccggcgac     180
cggatggcgc cataactcc ctcttgcttc aacctccaga tcacgggctc cggcaccgcc      240 cgccctcgg gtgttctcgg taccgagctc tacaagcccg acaacgaggg cattcgcttc      300
aacatctacc gctccatgga cagctacccg atccccggt                            339

<210> SEQ ID NO 54
<211> LENGTH: 113
<212> TYPE: PRT
<213> ORGANISM: Chaetomium senegalense

<400> SEQUENCE: 54

Leu Glu Phe Phe Lys Ile Asp Glu Val Gly Leu Val Asp Gly Ala Asn
  1               5                  10                  15

Ala Pro Gly Phe Trp Gly Ser Asp Gln Leu Ile Ala Asn Asn Ala Ala
                 20                  25                  30

Trp Met Val Gln Ile Pro Glu Asp Ile Ala Pro Gly Phe Tyr Val Val
             35                  40                  45

Arg His Glu Ile Ile Ala Leu His Ser Ala Gly Asp Arg Met Ala Pro
         50                  55                  60

Ile Thr Pro Ser Cys Phe Asn Leu Gln Ile Thr Gly Ser Gly Thr Ala
 65                  70                  75                  80

Arg Pro Ser Gly Val Leu Gly Thr Glu Leu Tyr Lys Pro Asp Asn Glu
                 85                  90                  95

Gly Ile Arg Phe Asn Ile Tyr Arg Ser Met Asp Ser Tyr Pro Ile Pro
            100                 105                 110

Gly

<210> SEQ ID NO 55
<211> LENGTH: 1101
<212> TYPE: DNA
<213> ORGANISM: Talaromyces leycettanus

<400> SEQUENCE: 55
atgcatcaac acttccgata cactgcgctc ctgacagcgt tgctgtcagc atcaacccga      60
gtcgcatccc acggccatgt cagcaacatt gtcattaatg gcgttcccta tcaaggatgg     120
gatatcgatt ccatgcccta cgagtcagac ccaccagtgg ttgtcgcctg ggagacacct     180
aacacgtcaa acggtttcat taccccggat cagtacggta cgagtgatat tatctgccat     240
```

-continued

```
ctgaacgcaa ccaacgcaaa gggccatgcc gtcgttgctg ccggagacaa gatcagcatt       300
caatggactg cctggcccag ctcccaccac ggccctgtca tcagctacct ggccaactgt       360
ggcgccagct gtgagacagt cgacaaaacg acgttgcaat tctttaagat cgacaacatc       420
ggtttcatag atgactcttc ccccccaggc atctgggcag ccgatcaatt ggaagcaaac       480
aacaacacct ggctcgtgga gatccccccg accatcgctc caggatacta cgtcctgcgc       540
aacgagatca tcgccctaca cggtgcagag aatcaggatg gcgcccagaa ctatccgcag       600
tgcttcaatc tgcaggtcac cggctcgggt accgataaac ccgccggcgt tcttggaact       660
cagctctatt ctcccactga cccgggcatt ctcgtgaaca tttacacgag cctttcgacc       720
tacatcgtcc ccggtccaac cccgtacagt ggttgggtgt ccgtcgtgca gtctagctct       780
gctatcaccg cttctggaac cccggtgacg ggcactggcg gagttagccc aaccacggct       840
gctactacga cttcttcttc tcactccacg acttctacta ctaccgggcc cactgtaacc       900
tcgactagcc acactactac cactactact cctactaccc tcagaaccac gactacaact       960
gcagctggtg gtggtgcgac acagaccgtc tacggccaat gcggcggtag tggttggact      1020
ggcgcaactg cctgcgcagc cggagctact tgcagcactc tgaatcccta ctatgcccaa      1080
tgccttccta ctggtgcttg a                                                1101
```

<210> SEQ ID NO 56
<211> LENGTH: 366
<212> TYPE: PRT
<213> ORGANISM: Talaromyces leycettanus

<400> SEQUENCE: 56

```
Met His Gln His Phe Arg Tyr Thr Ala Leu Leu Thr Ala Leu Leu Ser
1               5                   10                  15

Ala Ser Thr Arg Val Ala Ser His Gly His Val Ser Asn Ile Val Ile
                20                  25                  30

Asn Gly Val Pro Tyr Gln Gly Trp Asp Ile Asp Ser Met Pro Tyr Glu
            35                  40                  45

Ser Asp Pro Pro Val Val Ala Trp Glu Thr Pro Asn Thr Ser Asn
        50                  55                  60

Gly Phe Ile Thr Pro Asp Gln Tyr Gly Thr Ser Asp Ile Ile Cys His
65                  70                  75                  80

Leu Asn Ala Thr Asn Ala Lys Gly His Ala Val Val Ala Ala Gly Asp
                85                  90                  95

Lys Ile Ser Ile Gln Trp Thr Ala Trp Pro Ser Ser His His Gly Pro
            100                 105                 110

Val Ile Ser Tyr Leu Ala Asn Cys Gly Ala Ser Cys Glu Thr Val Asp
        115                 120                 125

Lys Thr Thr Leu Gln Phe Phe Lys Ile Asp Asn Ile Gly Phe Ile Asp
    130                 135                 140

Asp Ser Ser Pro Pro Gly Ile Trp Ala Ala Asp Gln Leu Glu Ala Asn
145                 150                 155                 160

Asn Asn Thr Trp Leu Val Glu Ile Pro Pro Thr Ile Ala Pro Gly Tyr
                165                 170                 175

Tyr Val Leu Arg Asn Glu Ile Ile Ala Leu His Gly Ala Glu Asn Gln
            180                 185                 190

Asp Gly Ala Gln Asn Tyr Pro Gln Cys Phe Asn Leu Gln Val Thr Gly
        195                 200                 205

Ser Gly Thr Asp Lys Pro Ala Gly Val Leu Gly Thr Gln Leu Tyr Ser
    210                 215                 220
```

Pro Thr Asp Pro Gly Ile Leu Val Asn Ile Tyr Thr Ser Leu Ser Thr
225                 230                 235                 240

Tyr Ile Val Pro Gly Pro Thr Pro Tyr Ser Gly Trp Val Ser Val Val
                245                 250                 255

Gln Ser Ser Ser Ala Ile Thr Ala Ser Gly Thr Pro Val Thr Gly Thr
            260                 265                 270

Gly Gly Val Ser Pro Thr Thr Ala Ala Thr Thr Ser Ser Ser His
            275                 280                 285

Ser Thr Thr Ser Thr Thr Thr Gly Pro Thr Val Thr Ser Thr Ser His
    290                 295                 300

Thr Thr Thr Thr Thr Thr Pro Thr Thr Leu Arg Thr Thr Thr Thr Thr
305                 310                 315                 320

Ala Ala Gly Gly Gly Ala Thr Gln Thr Val Tyr Gly Gln Cys Gly Gly
                325                 330                 335

Ser Gly Trp Thr Gly Ala Thr Ala Cys Ala Ala Gly Ala Thr Cys Ser
            340                 345                 350

Thr Leu Asn Pro Tyr Tyr Ala Gln Cys Leu Pro Thr Gly Ala
    355                 360                 365

<210> SEQ ID NO 57
<211> LENGTH: 293
<212> TYPE: DNA
<213> ORGANISM: Scytalidium indonesiacum

<400> SEQUENCE: 57
ttgtcataac caggccacca acgcgggcgg ccacgccgtg gtcgcggccg gcgacaagat    60
ctggatccag tgggaccaat ggcccgagag ccaccacggc cccgtcctcg actacctcgc   120
ctcctgcggc agctcgggct gcgagtcggt caacaagctc gacctcaagt tcttcaagat   180
cggcgaaaag ggcctgatcg acggctcctc cgcgccgggc cggtgggcgt cggacgagct   240
gatcgctaac aacgctggct ggctggtcca gatccccgcc gacatcgcgc tc           293

<210> SEQ ID NO 58
<211> LENGTH: 97
<212> TYPE: PRT
<213> ORGANISM: Scytalidium indonesiacum

<400> SEQUENCE: 58

Cys His Asn Gln Ala Thr Asn Ala Gly Gly His Ala Val Val Ala Ala
1               5                   10                  15

Gly Asp Lys Ile Trp Ile Gln Trp Asp Gln Trp Pro Glu Ser His His
            20                  25                  30

Gly Pro Val Leu Asp Tyr Leu Ala Ser Cys Gly Ser Ser Gly Cys Glu
        35                  40                  45

Ser Val Asn Lys Leu Asp Leu Lys Phe Phe Lys Ile Gly Glu Lys Gly
    50                  55                  60

Leu Ile Asp Gly Ser Ser Ala Pro Gly Arg Trp Ala Ser Asp Glu Leu
65                  70                  75                  80

Ile Ala Asn Asn Ala Gly Trp Leu Val Gln Ile Pro Ala Asp Ile Ala
                85                  90                  95

Pro

<210> SEQ ID NO 59
<211> LENGTH: 624
<212> TYPE: DNA
<213> ORGANISM: Scytalidium thermophilum

<400> SEQUENCE: 59

```
gacctggagt ttttcaagat cgatgccgct ggcttcgagg acggcaagtg ggcttctgac       60
aagctcatcg ccaacaacaa cacctggacc gtgaccgtcc ccgacagcat tgcccctggt      120
caatacgtcc tccgtcacga gatcatgctc ctccactccg ctggccagga aacggggcc       180
cagaagtacc ccaagtgcat caacatcgag gttaccggct ccggtaccgc taccccaag       240
ggtactccgg ccaacaagct ctacactgcc accgacccg gtatcaaggt caacgtctac       300
ggcggtgaca tgtccagcta cgagatgccc ggtcccgctc tgttcgacgg tgccagctcc      360
ggctccggct ctggcaacgc ttctgcgccc aagccttctg cctctgctcc tgcctcttct      420
gcctctgctg cccctgctgc caccagctcg gccgctgttg ccgctgtctc tactcccgct      480
gcctctgctt ccgccccgc ccagacaggc agcgccagcc tcgacaagga gttcaccctc      540
gacaccttca tctcctggct cgaggagaag gctggctctt ccagccagaa ggtccgccgc     600
caccccgcg ctttccgcgt ctaa                                             624
```

<210> SEQ ID NO 60
<211> LENGTH: 207
<212> TYPE: PRT
<213> ORGANISM: Scytalidium thermophilum

<400> SEQUENCE: 60

Asp Leu Glu Phe Phe Lys Ile Asp Ala Ala Gly Phe Glu Asp Gly Lys
1               5                   10                  15
Trp Ala Ser Asp Lys Leu Ile Ala Asn Asn Asn Thr Trp Thr Val Thr
            20                  25                  30
Val Pro Asp Ser Ile Ala Pro Gly Gln Tyr Val Leu Arg His Glu Ile
        35                  40                  45
Met Leu Leu His Ser Ala Gly Gln Glu Asn Gly Ala Gln Lys Tyr Pro
    50                  55                  60
Lys Cys Ile Asn Ile Glu Val Thr Gly Ser Gly Thr Ala Thr Pro Lys
65                  70                  75                  80
Gly Thr Pro Ala Asn Lys Leu Tyr Thr Ala Thr Asp Pro Gly Ile Lys
                85                  90                  95
Val Asn Val Tyr Gly Gly Asp Met Ser Ser Tyr Glu Met Pro Gly Pro
            100                 105                 110
Ala Leu Phe Asp Gly Ala Ser Ser Gly Ser Gly Ser Gly Asn Ala Ser
        115                 120                 125
Ala Pro Lys Pro Ser Ala Ser Ala Pro Ala Ser Ser Ala Ser Ala Ala
    130                 135                 140
Pro Ala Ala Thr Ser Ser Ala Ala Val Ala Ala Val Ser Thr Pro Ala
145                 150                 155                 160
Ala Ser Ala Ser Ala Pro Ala Gln Thr Gly Ser Ala Ser Leu Asp Lys
                165                 170                 175
Glu Phe Thr Leu Asp Thr Phe Ile Ser Trp Leu Glu Glu Lys Ala Gly
            180                 185                 190
Ser Ser Ser Gln Lys Val Arg Arg His Pro Arg Ala Phe Arg Val
        195                 200                 205

<210> SEQ ID NO 61
<211> LENGTH: 290
<212> TYPE: DNA
<213> ORGANISM: Talaromyces thermophilus

<400> SEQUENCE: 61

```
gacattattt gtcacaagaa tgccaaacct gctcccaaca aggcccaaat tcaagcgggc     60
gacaaggtgc ggctcgagtg gtctccatgg cccgggcctc ctgaccacca ggggcctatc    120
atcaactacc tagcgagctg caacggaccc tgctcaagtg tgcagaagga gagtcttaag    180
tgggcaaaga ttgacgagac tgggctcttt ccgaacggaa cgtgggcaac ggacgtgctc    240
cgctccaatg gaaacacatg ggatgtgaag atcccatcag acctgctcct               290
```

<210> SEQ ID NO 62
<211> LENGTH: 97
<212> TYPE: PRT
<213> ORGANISM: Talaromyces thermophilus

<400> SEQUENCE: 62

```
Asp Asp Ile Ile Cys His Lys Asn Ala Lys Pro Ala Pro Asn Lys Ala
1               5                   10                  15

Gln Ile Gln Ala Gly Asp Lys Val Arg Leu Glu Trp Ser Pro Trp Pro
            20                  25                  30

Gly Pro Pro Asp His Gln Gly Pro Ile Ile Asn Tyr Leu Ala Ser Cys
        35                  40                  45

Asn Gly Pro Cys Ser Ser Val Gln Lys Glu Ser Leu Lys Trp Ala Lys
    50                  55                  60

Ile Asp Glu Thr Gly Leu Phe Pro Asn Gly Thr Trp Ala Thr Asp Val
65                  70                  75                  80

Leu Arg Ser Asn Gly Asn Thr Trp Asp Val Lys Ile Pro Ser Asp Leu
                85                  90                  95

Leu
```

<210> SEQ ID NO 63
<211> LENGTH: 852
<212> TYPE: DNA
<213> ORGANISM: Talaromyces byssochlamydoides

<400> SEQUENCE: 63

```
atcaactacc tggccaactg tggcgacagc tgcgagacgg tcgacaagac caccctcaag     60
ttcttcaaga tcgacggcgt cggtcttgtg gacgacacca ctgtgccggg cacctggggc    120
gccgaccagc tgatcagcaa caacaacagc tggctggtcg agatcccccc gaccctttgcg   180 ccggggaact acgtcctgcg ccacgagatc atcgccctcc acagcgccgg ctcggaaaac    240
ggcgctcaga actacccgca atgcttcaac ctccaggtga ccggcacggg cacggagtcg    300
cccaccggcg ttgtcggcac ggagctctac agcgagaccg acgcgggcat cctcgtcaac    360
atctaccagt cgctctctac gtacgagatt cccggtccga ccctgatcag cggcgccgtc    420
tccatcagcc agtccacctc tgcgatcact gcttccggaa gcgctgtcac tggctctgcc    480
accgctatcg ctgcgcctat cgctgcctca actacttccg ctgccgctgc tgtttctttc    540
tctgctgcgg cttcttctgc tgccactgcg tccgtcccag ctgcgggatc gtctcaggtc    600
accaccggcg ctgtttcgtt atcgactgtg gtcgctcgac cggccactac gttgacgact    660
gtcacctcac ctgcggtcat caccagcgct cctgctacta tttctgcggc ttccggttct    720
gatggctccg tccagtccct ctacgggcag tgcggtggca tcaactggac cggtccgacc    780
gcctgcgcca gcggctccag ctgcacctcc tggaacccct actactacca gtgtgtggct    840
actgcagcct aa                                                         852
```

<210> SEQ ID NO 64

<211> LENGTH: 283
<212> TYPE: PRT
<213> ORGANISM: Talaromyces byssochlamydoides

<400> SEQUENCE: 64

```
Ile Asn Tyr Leu Ala Asn Cys Gly Asp Ser Cys Glu Thr Val Asp Lys
1               5                   10                  15

Thr Thr Leu Lys Phe Phe Lys Ile Asp Gly Val Gly Leu Val Asp Asp
            20                  25                  30

Thr Thr Val Pro Gly Thr Trp Gly Ala Asp Gln Leu Ile Ser Asn Asn
        35                  40                  45

Asn Ser Trp Leu Val Glu Ile Pro Pro Thr Leu Ala Pro Gly Asn Tyr
50                  55                  60

Val Leu Arg His Glu Ile Ile Ala Leu His Ser Ala Gly Ser Glu Asn
65                  70                  75                  80

Gly Ala Gln Asn Tyr Pro Gln Cys Phe Asn Leu Gln Val Thr Gly Thr
                85                  90                  95

Gly Thr Glu Ser Pro Thr Gly Val Val Gly Thr Glu Leu Tyr Ser Glu
            100                 105                 110

Thr Asp Ala Gly Ile Leu Val Asn Ile Tyr Gln Ser Leu Ser Thr Tyr
        115                 120                 125

Glu Ile Pro Gly Pro Thr Leu Ile Ser Gly Ala Val Ser Ile Ser Gln
    130                 135                 140

Ser Thr Ser Ala Ile Thr Ala Ser Gly Ser Ala Val Thr Gly Ser Ala
145                 150                 155                 160

Thr Ala Ile Ala Ala Pro Ile Ala Ala Ser Thr Thr Ser Ala Ala Ala
                165                 170                 175

Ala Val Ser Phe Ser Ala Ala Ala Ser Ser Ala Ala Thr Ala Ser Val
            180                 185                 190

Pro Ala Ala Gly Ser Ser Gln Val Thr Thr Gly Ala Val Ser Leu Ser
        195                 200                 205

Thr Val Val Ala Arg Pro Ala Thr Thr Leu Thr Thr Val Thr Ser Pro
    210                 215                 220

Ala Val Ile Thr Ser Ala Pro Ala Thr Ile Ser Ala Ala Ser Gly Ser
225                 230                 235                 240

Asp Gly Ser Val Gln Ser Leu Tyr Gly Gln Cys Gly Gly Ile Asn Trp
                245                 250                 255

Thr Gly Pro Thr Ala Cys Ala Ser Gly Ser Ser Cys Thr Ser Trp Asn
            260                 265                 270

Pro Tyr Tyr Tyr Gln Cys Val Ala Thr Ala Ala
        275                 280
```

<210> SEQ ID NO 65
<211> LENGTH: 597
<212> TYPE: DNA
<213> ORGANISM: Thermomyces lanuginosus

<400> SEQUENCE: 65

| | | | | | |
|---|---|---|---|---|---|
| gacattatct | gtcacaagga | agccacacca | gcccgcggtc | atgtctccgt | gaaggccggt | 60 |
| gacaagatct | acatccaatg | gcagccgaat | ccatggccgg | attccccacca | cggtcccgtc | 120 |
| ctggactatc | tggccccttg | caacgggccc | tgtgagtccg | tcgacaagac | cagcttgcgc | 180 |
| ttcttcaaga | tcgacggagt | gggtcttatc | gacggctctt | ctcctccggg | caagtgggcc | 240 |
| gacgacgaac | tcattgcgaa | cggcaacggg | tggctggttc | agatccccga | ggacatcaag | 300 |
| ccgggtaact | acgtcctgcg | acacgagatc | atcgccttgc | acagcgccgg | gaacccggac | 360 |

```
ggcgcccagc tgtacccgca gtgcttcaac cttgagatta cgggatccgg caccgtcgag      420
ccggagggcg tgccagccac cgagttctac tcgcccgatg acccgggcat cctggtcaac      480
atctacgagc ccctgtccac gtatgaggtg ccgggtccct cgctcatccc gcaggcggtt      540
cagatcgagc agtcttcgtc tgcgattacg gcgacgggca cgccgacgcc ggcatga         597
```

<210> SEQ ID NO 66
<211> LENGTH: 198
<212> TYPE: PRT
<213> ORGANISM: Thermomyces lanuginosus

<400> SEQUENCE: 66

```
Asp Ile Ile Cys His Lys Glu Ala Thr Pro Ala Arg Gly His Val Ser
1               5                   10                  15

Val Lys Ala Gly Asp Lys Ile Tyr Ile Gln Trp Gln Pro Asn Pro Trp
            20                  25                  30

Pro Asp Ser His His Gly Pro Val Leu Asp Tyr Leu Ala Pro Cys Asn
        35                  40                  45

Gly Pro Cys Glu Ser Val Asp Lys Thr Ser Leu Arg Phe Phe Lys Ile
    50                  55                  60

Asp Gly Val Gly Leu Ile Asp Gly Ser Ser Pro Gly Lys Trp Ala
65                  70                  75                  80

Asp Asp Glu Leu Ile Ala Asn Gly Asn Gly Trp Leu Val Gln Ile Pro
                85                  90                  95

Glu Asp Ile Lys Pro Gly Asn Tyr Val Leu Arg His Glu Ile Ile Ala
            100                 105                 110

Leu His Ser Ala Gly Asn Pro Asp Gly Ala Gln Leu Tyr Pro Gln Cys
        115                 120                 125

Phe Asn Leu Glu Ile Thr Gly Ser Gly Thr Val Glu Pro Glu Gly Val
    130                 135                 140

Pro Ala Thr Glu Phe Tyr Ser Pro Asp Asp Pro Gly Ile Leu Val Asn
145                 150                 155                 160

Ile Tyr Glu Pro Leu Ser Thr Tyr Glu Val Pro Gly Pro Ser Leu Ile
                165                 170                 175

Pro Gln Ala Val Gln Ile Glu Gln Ser Ser Ser Ala Ile Thr Ala Thr
            180                 185                 190

Gly Thr Pro Thr Pro Ala
        195
```

<210> SEQ ID NO 67
<211> LENGTH: 399
<212> TYPE: DNA
<213> ORGANISM: Talaromyces emersonii

<400> SEQUENCE: 67

```
atcacgtacc tggccaactg caacggcaac tgctcgaccg ttgacaagac gcagctggag      60
ttcttcaaga tcgaccagtc gggcctgatc aacgacactg accgccgggg cacctgggcg      120
tccgacaacc tcatcgccaa caacagc tggaccgtga ccatcccag caccctcgag         180 ccgggcaact acgtgctgcg ccacgagatc atcgccctgc actcggcggg caacaaagac      240
ggcgcccaga ctaccccca gtgcatcaac atcgaggtca cgggcggcgg ctcggtcgag       300
ccgacgggca cgctgggcga ggatctctac cacgacacgg acccgggcat tctgatcgac      360
atttacgagc cgattgcgac gtataccatt ccaggaccg                             399
```

```
<210> SEQ ID NO 68
<211> LENGTH: 133
<212> TYPE: PRT
<213> ORGANISM: Talaromyces emersonii

<400> SEQUENCE: 68

Ile Thr Tyr Leu Ala Asn Cys Asn Gly Asn Cys Ser Thr Val Asp Lys
1               5                   10                  15

Thr Gln Leu Glu Phe Phe Lys Ile Asp Gln Ser Gly Leu Ile Asn Asp
            20                  25                  30

Thr Asp Pro Pro Gly Thr Trp Ala Ser Asp Asn Leu Ile Ala Asn Asn
        35                  40                  45

Asn Ser Trp Thr Val Thr Ile Pro Ser Thr Leu Glu Pro Gly Asn Tyr
    50                  55                  60

Val Leu Arg His Glu Ile Ile Ala Leu His Ser Ala Gly Asn Lys Asp
65                  70                  75                  80

Gly Ala Gln Asn Tyr Pro Gln Cys Ile Asn Ile Glu Val Thr Gly Gly
                85                  90                  95

Gly Ser Val Glu Pro Thr Gly Thr Leu Gly Glu Asp Leu Tyr His Asp
            100                 105                 110

Thr Asp Pro Gly Ile Leu Ile Asp Ile Tyr Glu Pro Ile Ala Thr Tyr
        115                 120                 125

Thr Ile Pro Gly Pro
    130

<210> SEQ ID NO 69
<211> LENGTH: 295
<212> TYPE: DNA
<213> ORGANISM: Corynascus thermophilus

<400> SEQUENCE: 69
catttgtcac aagtcggcca ccaacgccgg cggtcatgcc gttgttgccg ccggcgacaa      60
gatttccatc cagtgggaca cctggcccga gtcgcaccac ggtccggtca tcgactacct     120
cgccgactgc ggcgacgcgg gctgcgagaa ggtcgacaag accacgctcg agttcttcaa     180
gatcagcgag aagggcctga tcgacggcag cagcgcgccc ggcaggtggg cgtccgacga     240
gctgatcgcc aacaacaact cgtggctggt ccagatcccg cccgacatcg ccccc          295

<210> SEQ ID NO 70
<211> LENGTH: 98
<212> TYPE: PRT
<213> ORGANISM: Corynascus thermophilus

<400> SEQUENCE: 70

Ile Cys His Lys Ser Ala Thr Asn Ala Gly Gly His Ala Val Val Ala
1               5                   10                  15

Ala Gly Asp Lys Ile Ser Ile Gln Trp Asp Thr Trp Pro Glu Ser His
            20                  25                  30

His Gly Pro Val Ile Asp Tyr Leu Ala Asp Cys Gly Asp Ala Gly Cys
        35                  40                  45

Glu Lys Val Asp Lys Thr Thr Leu Glu Phe Phe Lys Ile Ser Glu Lys
    50                  55                  60

Gly Leu Ile Asp Gly Ser Ser Ala Pro Gly Arg Trp Ala Ser Asp Glu
65                  70                  75                  80

Leu Ile Ala Asn Asn Asn Ser Trp Leu Val Gln Ile Pro Pro Asp Ile
                85                  90                  95

Ala Pro
```

<210> SEQ ID NO 71
<211> LENGTH: 321
<212> TYPE: DNA
<213> ORGANISM: Melanocarpus albomyces

<400> SEQUENCE: 71

```
tatttgtcac aagagcgcga ccccgggcgg cggccacgcc acggtcgctg ccggcgacaa      60
gatcagcctg gtctggaccc cgagtggcc cgagagccac attggcccg tcatcgacta     120
catggcggcg tgcaacggcg actgcgagac ggtcaacaag gagtcgctgc ggtggttcaa     180
gatcgacggc gccggctacg acagcagcaa gggccagtgg gccgccgacg cgctgcgtga     240
gaacggcaac agctggctgg tgcagatccc ctcggacctc gccccggca actacgtgct     300
ccggcacgag atcatgctgc a                                               321
```

<210> SEQ ID NO 72
<211> LENGTH: 106
<212> TYPE: PRT
<213> ORGANISM: Melanocarpus albomyces

<400> SEQUENCE: 72

```
Ile Cys His Lys Ser Ala Thr Pro Gly Gly His Ala Thr Val Ala
1               5                   10                  15

Ala Gly Asp Lys Ile Ser Leu Val Trp Thr Pro Glu Trp Pro Glu Ser
            20                  25                  30

His Ile Gly Pro Val Ile Asp Tyr Met Ala Ala Cys Asn Gly Asp Cys
        35                  40                  45

Glu Thr Val Asn Lys Glu Ser Leu Arg Trp Phe Lys Ile Asp Gly Ala
    50                  55                  60

Gly Tyr Asp Ser Ser Lys Gly Gln Trp Ala Ala Asp Ala Leu Arg Glu
65                  70                  75                  80

Asn Gly Asn Ser Trp Leu Val Gln Ile Pro Ser Asp Leu Ala Pro Gly
                85                  90                  95

Asn Tyr Val Leu Arg His Glu Ile Met Leu
                100                 105
```

<210> SEQ ID NO 73
<211> LENGTH: 452
<212> TYPE: DNA
<213> ORGANISM: Melanocarpus albomyces

<400> SEQUENCE: 73

```
gcccggaaag gaggtgctac gcgccgagcc tgttctacca ggtgctcggc gaggagtaca      60
tcaagctcgc gttccgcgtc gcggccgagg cggacccggc cgccaagctg tactacaacg     120
actacggcat ctagcggccc gactccccca agacggcggg cgtccggctc ctggtgcgca     180
tgctgaagcg cgccggcgtg ctcatcgacg gcgtcagcat gcaggcggac ctgcacgccg     240
acaaccaccc gtccgcggcc gagctggtgg ccacgatgcg cggctacgcc ccggtcgtcg     300
acgaggtcac gttcagcgag ctcgacgtgc gcatcaacct gcccgtcgac gcccacaacc     360
tggcctgccg gcgcgagtgc tacaagaagg tggtcaccgc ctgcggcgcc gtcaaaaagt     420
gcgtcggcat gaccgtctgg gggtccaggg gg                                   452
```

<210> SEQ ID NO 74
<211> LENGTH: 149
<212> TYPE: PRT
<213> ORGANISM: Melanocarpus albomyces

<400> SEQUENCE: 74

```
Pro Glu Arg Arg Cys Tyr Ala Pro Ser Leu Phe Tyr Gln Val Leu Gly
 1               5                  10                  15

Glu Glu Tyr Ile Lys Leu Ala Phe Arg Val Ala Ala Glu Ala Asp Pro
            20                  25                  30

Ala Ala Lys Leu Tyr Tyr Asn Asp Tyr Gly Ile Arg Pro Asp Ser Pro
        35                  40                  45

Lys Thr Ala Gly Val Arg Leu Val Arg Met Leu Lys Arg Ala Gly
    50                  55                  60

Val Leu Ile Asp Gly Val Ser Met Gln Ala Asp Leu His Ala Asp Asn
 65                  70                  75                  80

His Pro Ser Ala Ala Glu Leu Val Ala Thr Met Arg Gly Tyr Ala Pro
                85                  90                  95

Val Val Asp Glu Val Thr Phe Ser Glu Leu Asp Val Arg Ile Asn Leu
            100                 105                 110

Pro Val Asp Ala His Asn Leu Ala Cys Arg Arg Glu Cys Tyr Lys Lys
        115                 120                 125

Val Val Thr Ala Cys Gly Ala Val Lys Lys Cys Val Gly Met Thr Val
    130                 135                 140

Trp Gly Ser Arg Gly
145
```

<210> SEQ ID NO 75
<211> LENGTH: 426
<212> TYPE: DNA
<213> ORGANISM: Chaetomium thermophilum

<400> SEQUENCE: 75

```
tggcgcgact ccgtcttcta ccgcaccttc ggcaccgact acttcgccat cgccttccgt      60
gccgcccgcg ccgctgaccc cagcgccaag ctctattata cgactacaa ccttgagtac     120
aacggtgcca agaccgagaa ggctctcgag ctggtgcgca tcatcaagaa cgctggcgct     180
cccatcgatg gtgtcggctt ccaaggtcac ttgattgttg gcagcacccc cagccgcagc     240
agcctggcta ctgttctccg ccgcttcact gccctcggtg tcgaggttgc ttacaccgag     300
attgatatcc gccactcgag cctgcctgcc tcgagctcgg ccctcgtcac ccagggcaac     360
gactacgcca cgtcgtcgg ctcttgcctc gacgtcgagg gctgcgtggg catcaccgtc     420
tggggg                                                                426
```

<210> SEQ ID NO 76
<211> LENGTH: 142
<212> TYPE: PRT
<213> ORGANISM: Chaetomium thermophilum

<400> SEQUENCE: 76

```
Trp Arg Asp Ser Val Phe Tyr Arg Thr Phe Gly Thr Asp Tyr Phe Ala
 1               5                  10                  15

Ile Ala Phe Arg Ala Ala Arg Ala Ala Asp Pro Ser Ala Lys Leu Tyr
            20                  25                  30

Tyr Asn Asp Tyr Asn Leu Glu Tyr Asn Gly Ala Lys Thr Glu Lys Ala
        35                  40                  45

Leu Glu Leu Val Arg Ile Ile Lys Asn Ala Gly Ala Pro Ile Asp Gly
    50                  55                  60

Val Gly Phe Gln Gly His Leu Ile Val Gly Ser Thr Pro Ser Arg Ser
 65                  70                  75                  80
```

```
Ser Leu Ala Thr Val Leu Arg Arg Phe Thr Ala Leu Gly Val Glu Val
            85                  90                  95

Ala Tyr Thr Glu Ile Asp Ile Arg His Ser Ser Leu Pro Ala Ser Ser
        100                 105                 110

Ser Ala Leu Val Thr Gln Gly Asn Asp Tyr Ala Asn Val Val Gly Ser
    115                 120                 125

Cys Leu Asp Val Glu Gly Cys Val Gly Ile Thr Val Trp Gly
    130                 135                 140

<210> SEQ ID NO 77
<211> LENGTH: 405
<212> TYPE: DNA
<213> ORGANISM: Chaetomium senegalense

<400> SEQUENCE: 77
agcctgcgcg acagcgtctt cagccgcgtg ctgggcgagg actttgtcgg catcgccttc      60
cgcgcggccc gcgccgccga cccgggcgcc aagttgtaca tcaacgacta caacctcgac     120
atcgccaact acgccaaggt cacccgcggc atggtcgaga aggtcaacaa atggctcgcc     180
cagggcatcc ccatcgacgg catcggctcg cagtgccacc tcgccgcccc gggggggttgg    240 aatcccgcgt ccggcgtccc ggccgcgctg cgggcgctcg cggcgtcgaa cgtgagggag     300
attgccgtga ccgagctgga cattgccggc gccgcggcca acgactatct caccgtcatg     360
aacgcgtgcc tgcagatcga aagtgtgtt ggcatcaccg tctgg                      405

<210> SEQ ID NO 78
<211> LENGTH: 135
<212> TYPE: PRT
<213> ORGANISM: Chaetomium senegalense

<400> SEQUENCE: 78

Ser Leu Arg Asp Ser Val Phe Ser Arg Val Leu Gly Glu Asp Phe Val
1               5                   10                  15

Gly Ile Ala Phe Arg Ala Ala Arg Ala Ala Asp Pro Gly Ala Lys Leu
            20                  25                  30

Tyr Ile Asn Asp Tyr Asn Leu Asp Ile Ala Asn Tyr Ala Lys Val Thr
        35                  40                  45

Arg Gly Met Val Glu Lys Val Asn Lys Trp Leu Ala Gln Gly Ile Pro
    50                  55                  60

Ile Asp Gly Ile Gly Ser Gln Cys His Leu Ala Ala Pro Gly Gly Trp
65                  70                  75                  80

Asn Pro Ala Ser Gly Val Pro Ala Ala Leu Arg Ala Leu Ala Ala Ser
            85                  90                  95

Asn Val Arg Glu Ile Ala Val Thr Glu Leu Asp Ile Ala Gly Ala Ala
        100                 105                 110

Ala Asn Asp Tyr Leu Thr Val Met Asn Ala Cys Leu Gln Ile Glu Lys
    115                 120                 125

Cys Val Gly Ile Thr Val Trp
    130                 135

<210> SEQ ID NO 79
<211> LENGTH: 361
<212> TYPE: PRT
<213> ORGANISM: Chaetomium thermophilum

<400> SEQUENCE: 79

Met Pro Ser Phe Ala Ser Lys Thr Leu Ile Ser Ala Leu Ala Gly Ala
```

```
  1               5                   10                  15
Ala Ser Val Ala Ala His Gly His Val Lys Asn Phe Val Ile Asn Gly
          20                  25                  30
Leu Ser Tyr Gln Ala Tyr Asp Pro Thr Val Phe Pro Tyr Met Gln Asn
          35                  40                  45
Pro Pro Ile Val Ala Gly Trp Thr Ala Ser Asn Thr Asp Asn Gly Phe
 50                  55                  60
Val Gly Pro Glu Ser Tyr Ser Ser Pro Asp Ile Ile Cys His Lys Ser
 65                  70                  75                  80
Ala Thr Asn Ala Lys Gly His Ala Val Ile Lys Ala Gly Asp Ser Val
                  85                  90                  95
Tyr Ile Gln Trp Asp Thr Trp Pro Glu Ser His His Gly Pro Val Ile
                 100                 105                 110
Asp Tyr Leu Ala Ser Cys Gly Ser Ala Gly Cys Glu Thr Val Asp Lys
                 115                 120                 125
Thr Gln Leu Glu Phe Phe Lys Ile Ala Glu Ala Gly Leu Ile Asp Gly
                 130                 135                 140
Ser Gln Ala Pro Gly Lys Trp Ala Ala Asp Gln Leu Ile Ala Gln Asn
145                 150                 155                 160
Asn Ser Trp Leu Val Thr Ile Pro Glu Asn Ile Lys Pro Gly Ser Tyr
                 165                 170                 175
Val Leu Arg His Glu Ile Ile Ala Leu His Ser Ala Gly Gln Thr Asn
                 180                 185                 190
Gly Ala Gln Asn Tyr Pro Val Cys Ile Asn Leu Glu Val Thr Gly Gly
                 195                 200                 205
Gly Ser Asp Val Pro Ser Gly Val Lys Gly Thr Glu Leu Tyr Lys Pro
                 210                 215                 220
Thr Asp Pro Gly Ile Leu Ile Asn Ile Tyr Gln Ser Leu Ser Asn Tyr
225                 230                 235                 240
Thr Ile Pro Gly Pro Ala Leu Met Pro Gly Ala Lys Pro Val Thr Gln
                 245                 250                 255
His Thr Ser Ala Ile Ile Gly Ser Thr Thr Ala Ile Thr Gly Thr Ala
                 260                 265                 270
Thr Ala Ala Pro Ala Ala Pro Thr Ser Thr Ala Ala Ile Thr Thr
                 275                 280                 285
Ser Ser Ala Asn Ala Asn Pro Ala Pro Thr Thr Thr Arg Gly Asn Ala
                 290                 295                 300
Asn Pro Val Pro Thr Thr Thr Leu Arg Thr Ser Thr Ile Ala Pro Gln
305                 310                 315                 320
Pro Thr Ala Ala Pro Ile Gln Thr Pro Thr Ser Ser Val Gly Arg Pro
                 325                 330                 335
Pro Arg Pro Thr Arg Cys Pro Gly Leu Asp Asn Phe Lys Arg Ala Arg
                 340                 345                 350
Arg His Ala Arg Asp Leu Ala Ala His
                 355                 360
```

<210> SEQ ID NO 80
<211> LENGTH: 23
<212> TYPE: DNA
<213> ORGANISM: Artificial
<220> FEATURE:
<223> OTHER INFORMATION: PCR primer

<400> SEQUENCE: 80
ctggacgaya thathtgyca yaa        23

<210> SEQ ID NO 81
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 81
ctggactgna gngcdatdat ytc                                         23

<210> SEQ ID NO 82
<211> LENGTH: 20
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 82
ctggaccayc ayggnccngt                                             20

<210> SEQ ID NO 83
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 83
ctggacggrt arttytgngc ncc                                         23

<210> SEQ ID NO 84
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (9)..(9)
<223> OTHER INFORMATION: n is a, c, g, or t

<400> SEQUENCE: 84
ctggacctng arttyttyaa rat                                         23

<210> SEQ ID NO 85

```
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (18)..(18)
<223> OTHER INFORMATION: n is inosine

<400> SEQUENCE: 85
caggtcctnc cngaymgnga ytg                                              23

<210> SEQ ID NO 86
<211> LENGTH: 22
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (18)..(18)
<223> OTHER INFORMATION: n is inosine

<400> SEQUENCE: 86
caggtcggnt ggctnggntg gc                                               22

<210> SEQ ID NO 87
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (18)..(18)
<223> OTHER INFORMATION: n is a, c, g, or t

<400> SEQUENCE: 87
caggtcggnc tngcnacnaa ygt                                              23

<210> SEQ ID NO 88
<211> LENGTH: 23
<212> TYPE: DNA
<213> ORGANISM: Artificial
```

```
<220> FEATURE:
<223> OTHER INFORMATION: PCR primer
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (18)..(18)
<223> OTHER INFORMATION: n is inosine
<220> FEATURE:
<221> NAME/KEY: misc_feature
<222> LOCATION: (21)..(21)
<223> OTHER INFORMATION: n is inosine

<400> SEQUENCE: 88
caggtcccng cytcnggngc ngg                                       23

<210> SEQ ID NO 89
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (12)..(12)
<223> OTHER INFORMATION: n is inosine

<400> SEQUENCE: 89
caggtcaart angcytgraa cca                                       23

<210> SEQ ID NO 90
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (21)..(21)
<223> OTHER INFORMATION: n is inosine

<400> SEQUENCE: 90
ctggacgtng tntaygayct ncc                                       23

<210> SEQ ID NO 91
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
```

<221> NAME/KEY: misc_feature
<222> LOCATION: (18)..(18)
<223> OTHER INFORMATION: n is inosine

<400> SEQUENCE: 91
ctggacccnc cnggyttnac cca                                              23

<210> SEQ ID NO 92
<211> LENGTH: 24
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (21)..(21)
<223> OTHER INFORMATION: n is inosine

<400> SEQUENCE: 92
ctggacgayg cnaaytggmg ntgg                                             24

<210> SEQ ID NO 93
<211> LENGTH: 26
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (24)..(24)
<223> OTHER INFORMATION: n is inosine

<400> SEQUENCE: 93
ctggacgart tyacnttyga ygtnga                                           26

<210> SEQ ID NO 94
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (15)..(15)
<223> OTHER INFORMATION: n is inosine

<400> SEQUENCE: 94
ctggacggna cnggntaytg yga                                              23

<210> SEQ ID NO 95
<211> LENGTH: 26
<212> TYPE: DNA
<213> ORGANISM: Artificial
<220> FEATURE:
<223> OTHER INFORMATION: PCR primer

<400> SEQUENCE: 95
ctggacgcyt cccadatrtc catytc                                          26

<210> SEQ ID NO 96
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (18)..(18)
<223> OTHER INFORMATION: n is inosine

<400> SEQUENCE: 96
ctggacttra artcrcancc rtc                                             23

<210> SEQ ID NO 97
<211> LENGTH: 20
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (18)..(18)
<223> OTHER INFORMATION: n is inosine

<400> SEQUENCE: 97
ctggacaayt gngtnacnac                                                 20

<210> SEQ ID NO 98
<211> LENGTH: 23
<212> TYPE: DNA
<213> ORGANISM: Artificial
<220> FEATURE:
<223> OTHER INFORMATION: PCR primer

<400> SEQUENCE: 98
caggtctayt gggaytgytg yaa                                             23

<210> SEQ ID NO 99
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (18)..(18)

<223> OTHER INFORMATION: n is inosine
<220> FEATURE:
<221> NAME/KEY: misc_feature
<222> LOCATION: (21)..(21)
<223> OTHER INFORMATION: n is inosine

<400> SEQUENCE: 99
caggtcccna cnccnccncc ngg                                              23

<210> SEQ ID NO 100
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (18)..(18)
<223> OTHER INFORMATION: n is inosine

<400> SEQUENCE: 100
caggtcaacc arttrtanck cca                                              23

<210> SEQ ID NO 101
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (18)..(18)
<223> OTHER INFORMATION: n is inosine

<400> SEQUENCE: 101
ctggactggt gytgygcntg yta                                              23

<210> SEQ ID NO 102
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (12)..(12)
<223> OTHER INFORMATION: n is inosine

<400> SEQUENCE: 102
ctggactarc angcrcarca cca                                              23

<210> SEQ ID NO 103
<211> LENGTH: 23
<212> TYPE: DNA
<213> ORGANISM: Artificial
<220> FEATURE:
<223> OTHER INFORMATION: PCR primer

<400> SEQUENCE: 103
ctggactggg aytgytgyaa rcc                                              23